United States Patent
Horton, IV et al.

(10) Patent No.: US 10,821,006 B2
(45) Date of Patent: Nov. 3, 2020

(54) BONE CLEANER THAT REMOVES SOFT TISSUE BY PRESSING BONE STOCK AGAINST A CLEANING ELEMENT AND CLEARING THE BONE STOCK FROM THE CLEANING ELEMENT

(71) Applicant: Stryker Corporation, Kalamazoo, MI (US)

(72) Inventors: John Coleman Horton, IV, Austin, TX (US); John Bernero, Round Rock, TX (US); Steven Brown, Austin, TX (US); Eric Diehl, San Francisco, CA (US); Shammodip Roy, Mahwah, NJ (US); Robin Babaris, Portage, MI (US); Robert Lynch, Portage, MI (US); Adam Thelen, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 304 days.

(21) Appl. No.: 15/748,079

(22) PCT Filed: Jul. 28, 2016

(86) PCT No.: PCT/US2016/044386
§ 371 (c)(1),
(2) Date: Jan. 26, 2018

(87) PCT Pub. No.: WO2017/019827
PCT Pub. Date: Feb. 2, 2017

(65) Prior Publication Data
US 2019/0029846 A1    Jan. 31, 2019

Related U.S. Application Data

(60) Provisional application No. 62/197,780, filed on Jul. 28, 2015.

(51) Int. Cl.
*A61F 2/46* (2006.01)
*A61F 2/28* (2006.01)

(52) U.S. Cl.
CPC .... *A61F 2/4644* (2013.01); *A61F 2002/2835* (2013.01); *A61F 2002/4645* (2013.01);
(Continued)

(58) Field of Classification Search
CPC . A47J 42/56; A47J 43/075; A61F 2002/4646; A61F 2/4644; A61F 2002/4645
See application file for complete search history.

(56) References Cited

U.S. PATENT DOCUMENTS 4,629,131 A * 12/1986 Podell ................... A47J 43/046
241/199.12
4,741,482 A * 5/1988 Coggiola .............. A47J 43/046
241/282.1
(Continued)

FOREIGN PATENT DOCUMENTS

JP    2004509631 A    4/2004
JP    2008534191 A    8/2008
(Continued)

OTHER PUBLICATIONS

International Search Report for Application No. PCT/US2010/055646 dated Feb. 28, 2011, 4 pages.
(Continued)

*Primary Examiner* — David W Bates
(74) *Attorney, Agent, or Firm* — Howard & Howard Attorneys PLLC

(57) ABSTRACT

A bone cleaning assembly (102, 602) with cleaning elements (690, 724, 1230, 1264) that remove soft tissue bone stock. The module also includes a clearing element (778) that is
(Continued)

periodically urged against the cleaning elements to remove bone stock trapped by the cleaning elements from the cleaning elements.

23 Claims, 56 Drawing Sheets

(52) U.S. Cl.
CPC .............. *A61F 2002/4646* (2013.01); *A61F 2310/00359* (2013.01)

(56) References Cited

U.S. PATENT DOCUMENTS

| | | | |
|---|---|---|---|
| 5,977,432 A * | 11/1999 | Wolfinbarger, Jr. | ........................ A61F 2/4644 128/898 |
| 6,017,354 A | 1/2000 | Culp et al. | |
| 6,217,614 B1 | 4/2001 | Fages et al. | |
| 6,287,312 B1 | 9/2001 | Clokie et al. | |
| 6,755,365 B1 | 6/2004 | Meredith | |
| 6,824,087 B2 | 11/2004 | McPherson et al. | |
| 7,028,930 B2 * | 4/2006 | Carnevale | ........... A47J 43/0777 241/278.1 |
| 7,029,387 B2 | 4/2006 | van den Nieuwelaar et al. | |
| 7,063,283 B2 * | 6/2006 | Wanat | ................. A47J 43/0716 241/282.1 |
| 7,131,605 B2 | 11/2006 | McPherson et al. | |
| 7,422,582 B2 | 9/2008 | Malackowski et al. | |
| 7,520,453 B2 * | 4/2009 | Clapp | ................. A47J 43/0772 241/282.1 |
| 7,588,202 B2 | 9/2009 | Rasekhi | |
| 8,002,774 B2 * | 8/2011 | Burmeister, III | ....... B02C 18/16 606/79 |
| 8,512,342 B2 * | 8/2013 | Meredith | ................. A61F 2/46 606/84 |
| 8,622,953 B2 | 1/2014 | Hynes et al. | |
| 8,672,942 B2 | 3/2014 | Chamberlin et al. | |
| 8,740,114 B2 | 6/2014 | Koltz et al. | |
| 9,370,436 B2 | 6/2016 | Stratton | |
| 10,045,863 B2 | 8/2018 | Stratton et al. | |
| 10,258,201 B1 | 4/2019 | Rasekhi | |
| 2002/0176320 A1 * | 11/2002 | Wulf | ..................... A47J 43/085 366/205 |
| 2006/0138260 A1 | 6/2006 | Hay et al. | |
| 2006/0261685 A1 * | 11/2006 | Schindler | .................. B25F 5/00 310/50 |
| 2007/0164137 A1 | 7/2007 | Rasekhi | |
| 2008/0274682 A1 | 11/2008 | Iversen | |
| 2009/0118713 A1 * | 5/2009 | Munson | ................ A61F 2/4644 606/1 |
| 2009/0118735 A1 | 5/2009 | Burmeister, III et al. | |
| 2010/0291506 A1 | 11/2010 | Olsson et al. | |
| 2010/0308142 A1 * | 12/2010 | Krasznai | ............. A47J 43/0772 241/36 |
| 2011/0166503 A1 * | 7/2011 | Koltz | .................... A61F 2/4644 604/22 |
| 2011/0248108 A1 * | 10/2011 | Carriere | .............. A47J 43/0772 241/33 |
| 2012/0310243 A1 * | 12/2012 | Stratton | ................ A61F 2/4644 606/79 |
| 2013/0001340 A1 * | 1/2013 | Garcia | ................. A47J 43/0777 241/36 |
| 2014/0263778 A1 | 9/2014 | Koltz et al. | |
| 2014/0303623 A1 * | 10/2014 | Diehl | .................. A61B 17/1635 606/79 |
| 2014/0322411 A1 * | 10/2014 | Segurola | .................. A47J 43/24 426/443 |
| 2016/0278942 A1 | 9/2016 | Stratton et al. | |
| 2016/0309960 A1 * | 10/2016 | Kolar | ................... A47J 43/0761 |
| 2018/0020875 A1 * | 1/2018 | Kolar | .................... B01F 13/047 366/279 |
| 2018/0078094 A1 * | 3/2018 | Haney | .................... A47J 43/075 |
| 2019/0000275 A1 * | 1/2019 | Sapire | ...................... A47J 36/10 |

FOREIGN PATENT DOCUMENTS

| | | |
|---|---|---|
| WO | 03082159 A1 | 10/2003 |
| WO | 2009061728 A1 | 5/2009 |

OTHER PUBLICATIONS

English language abstract for JP 2004-509631 extracted from espacenet.com database on Nov. 15, 2017, 2 pages.

English language abstract and machine-assisted English translation for JP 2008-534191 extracted from espacenet.com database on Nov. 15, 2017, 24 pages.

International Search Report for Application No. PCT/US2016/044386 dated Jan. 20, 2017, 4 pages.

\* cited by examiner

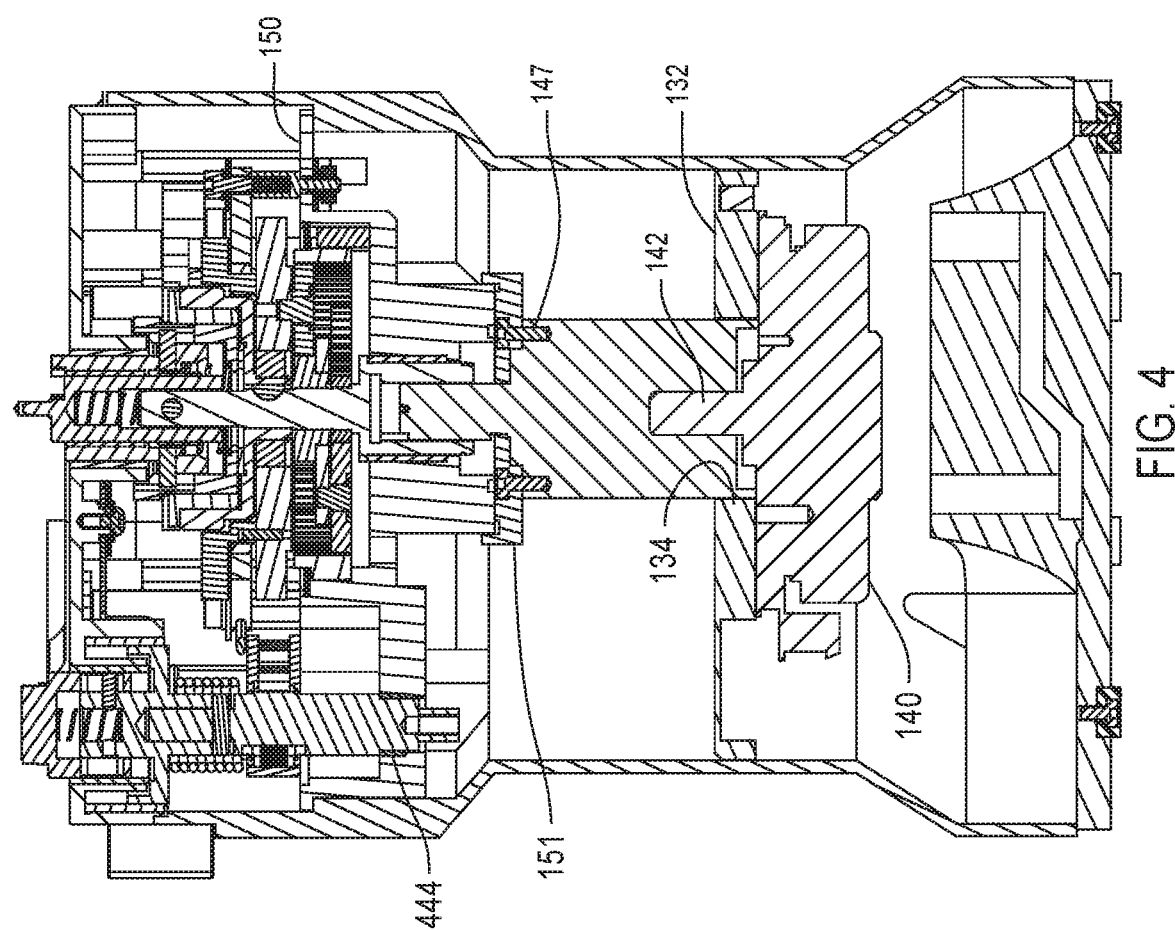

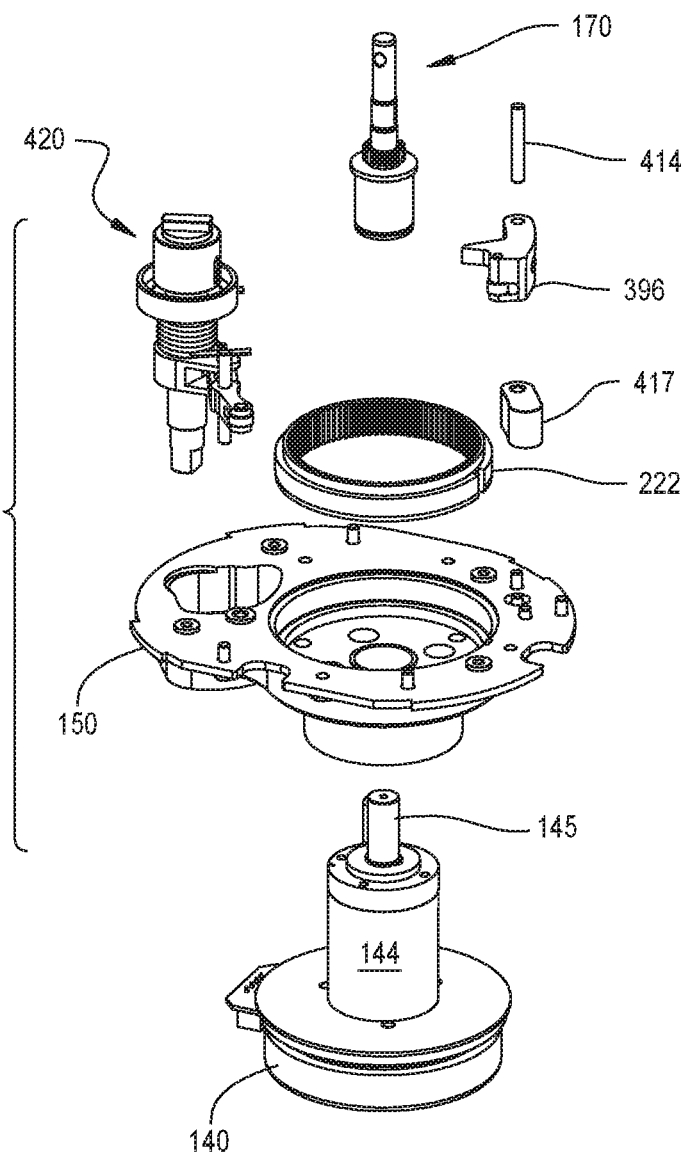

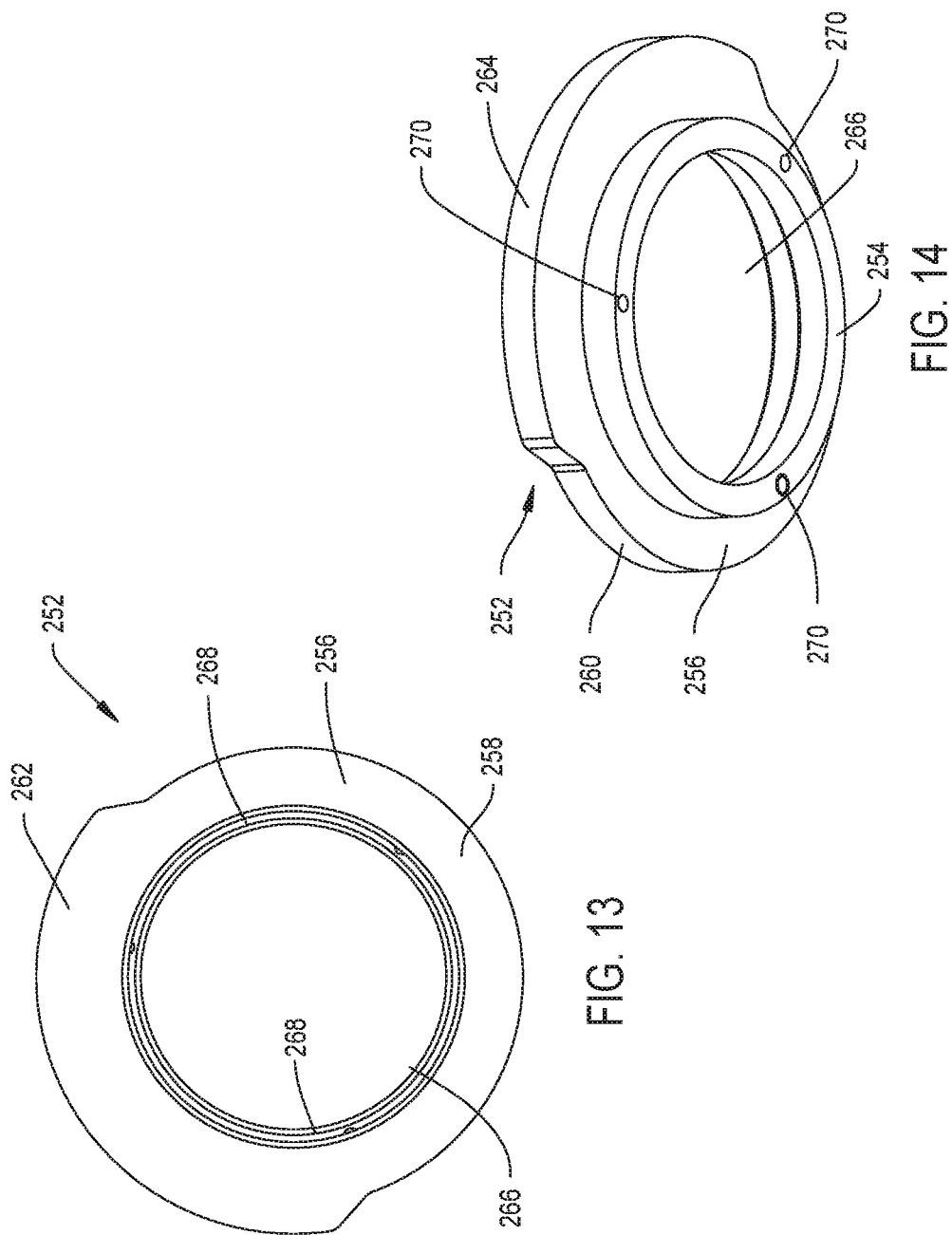

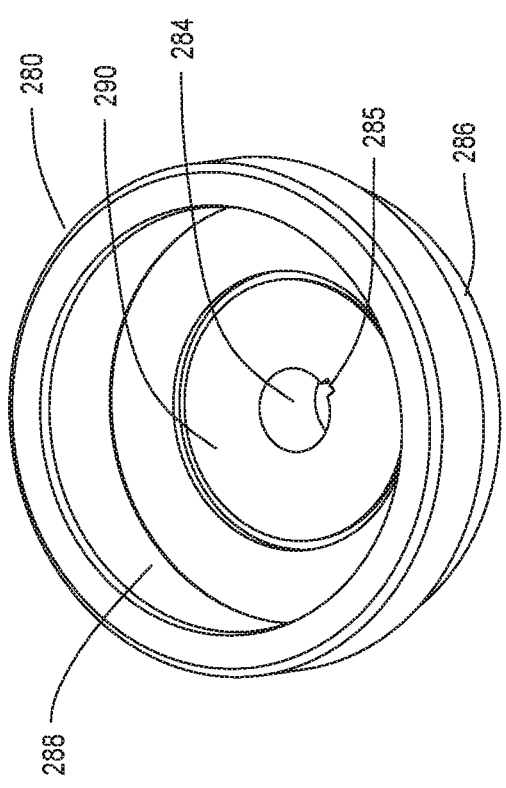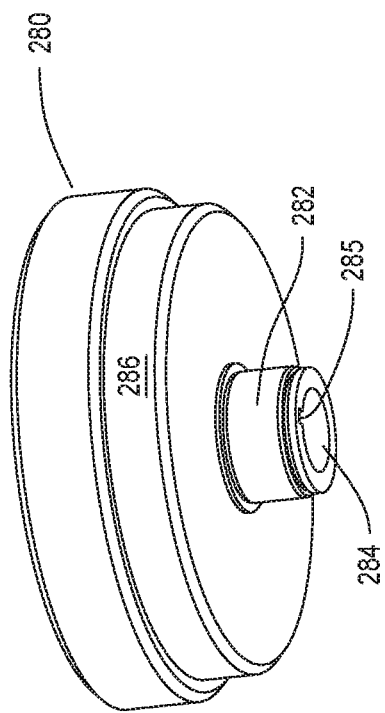

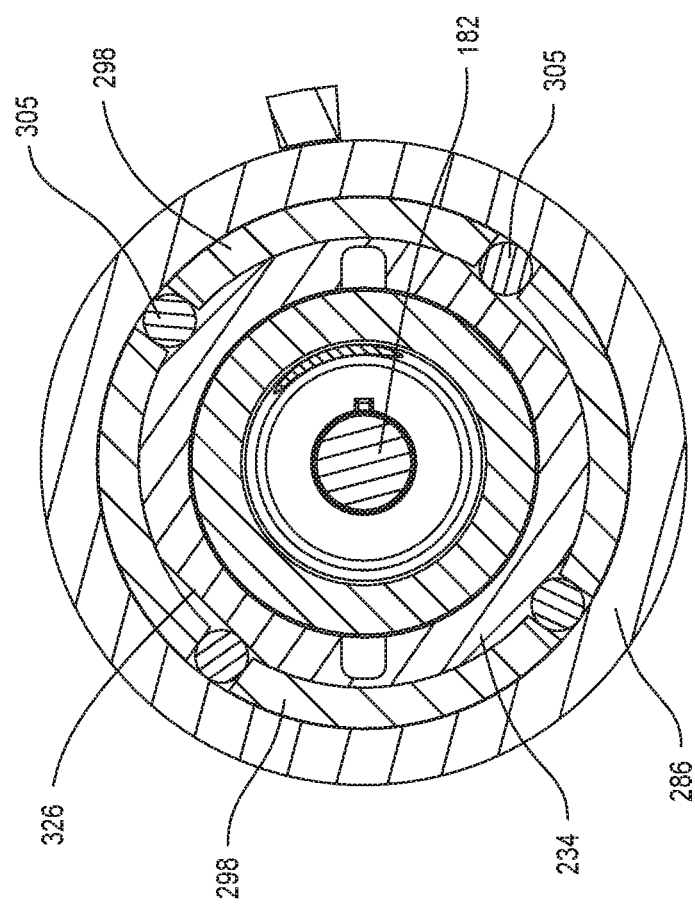

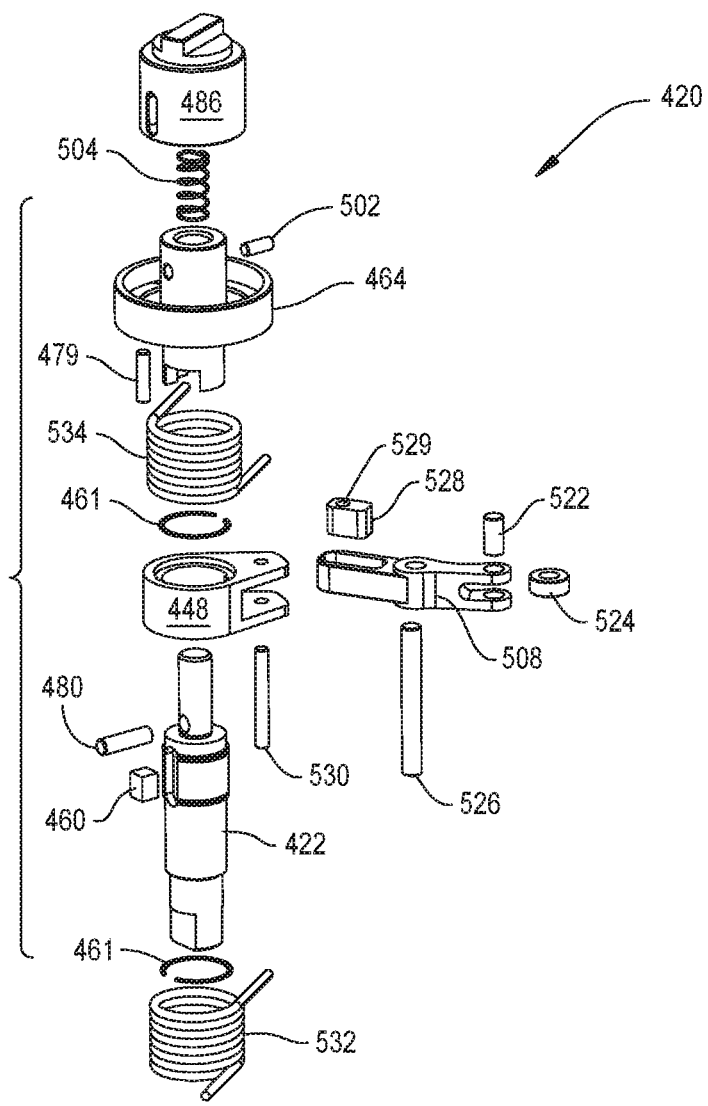

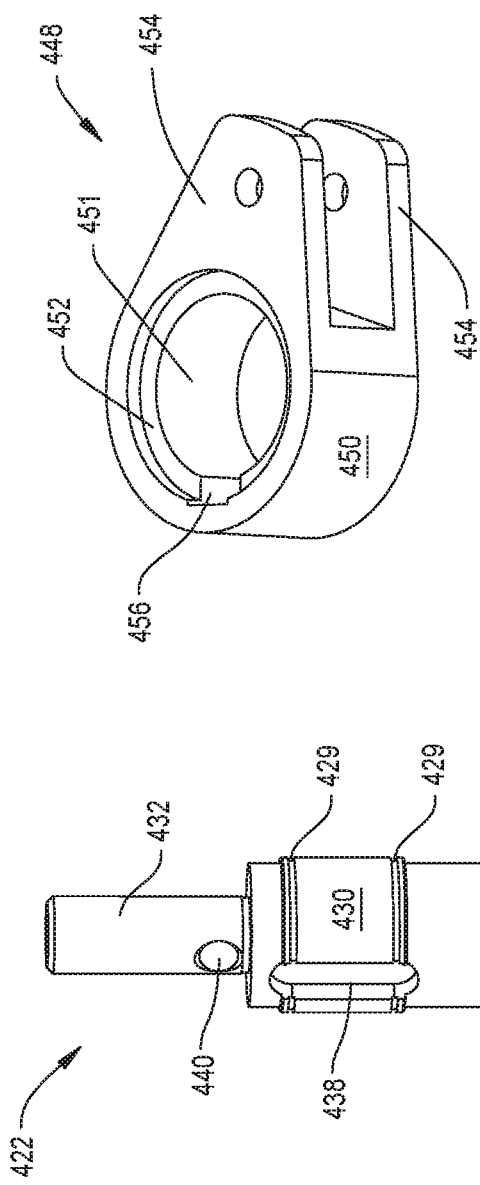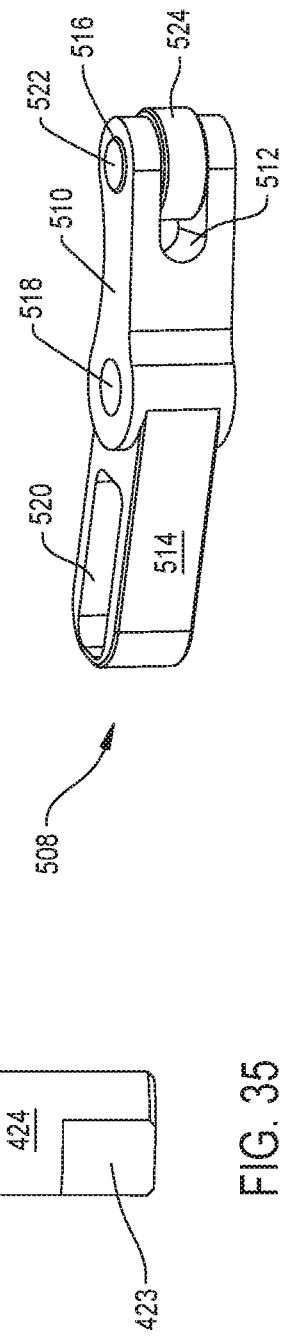

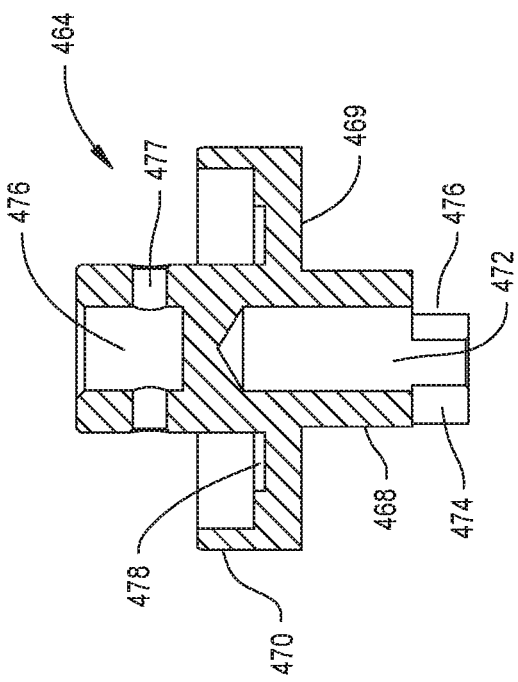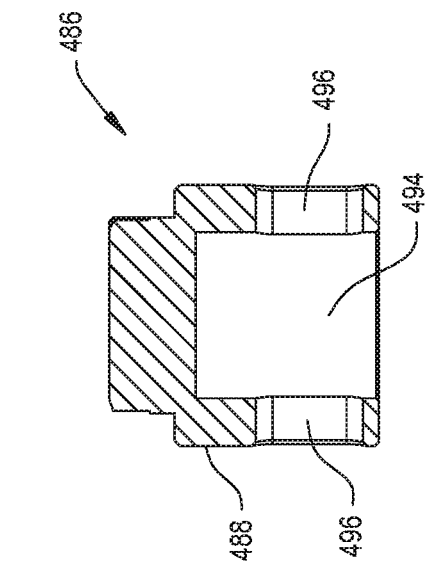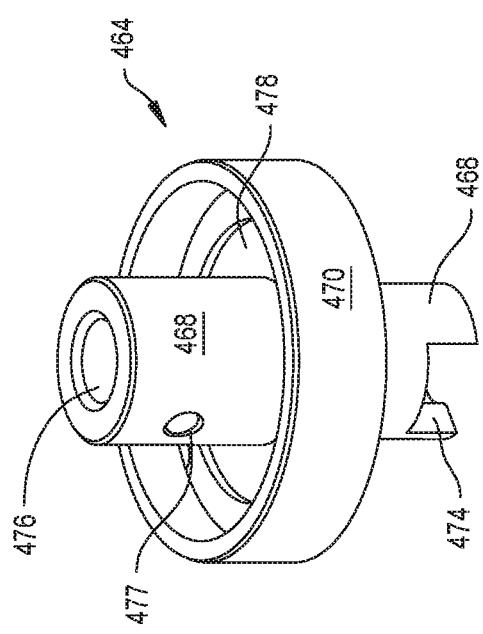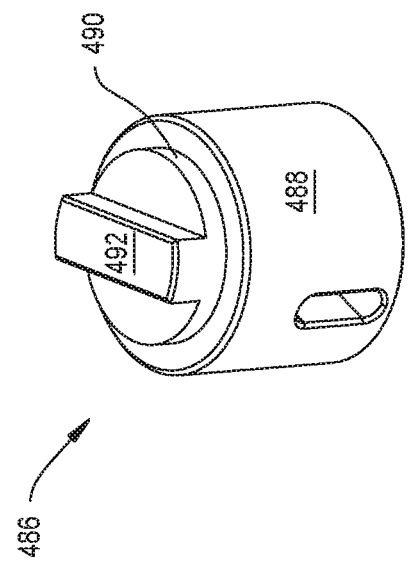

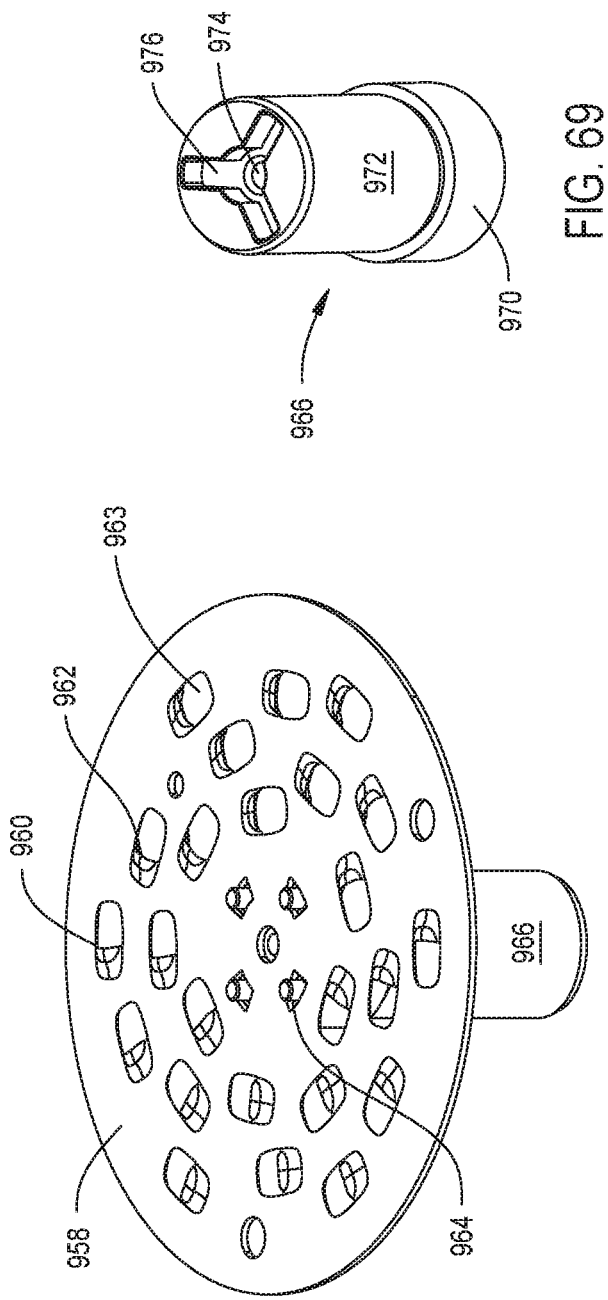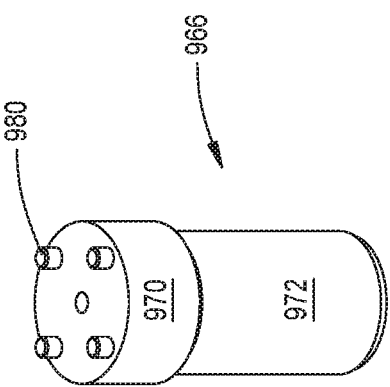

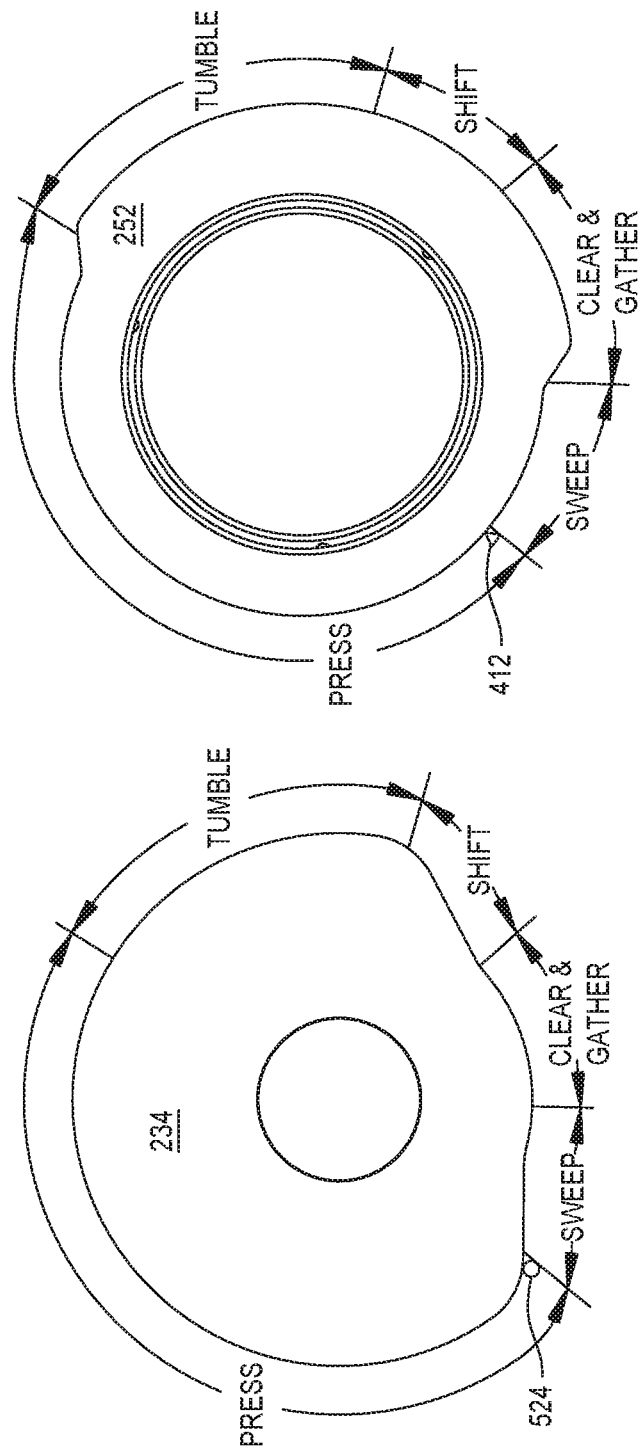

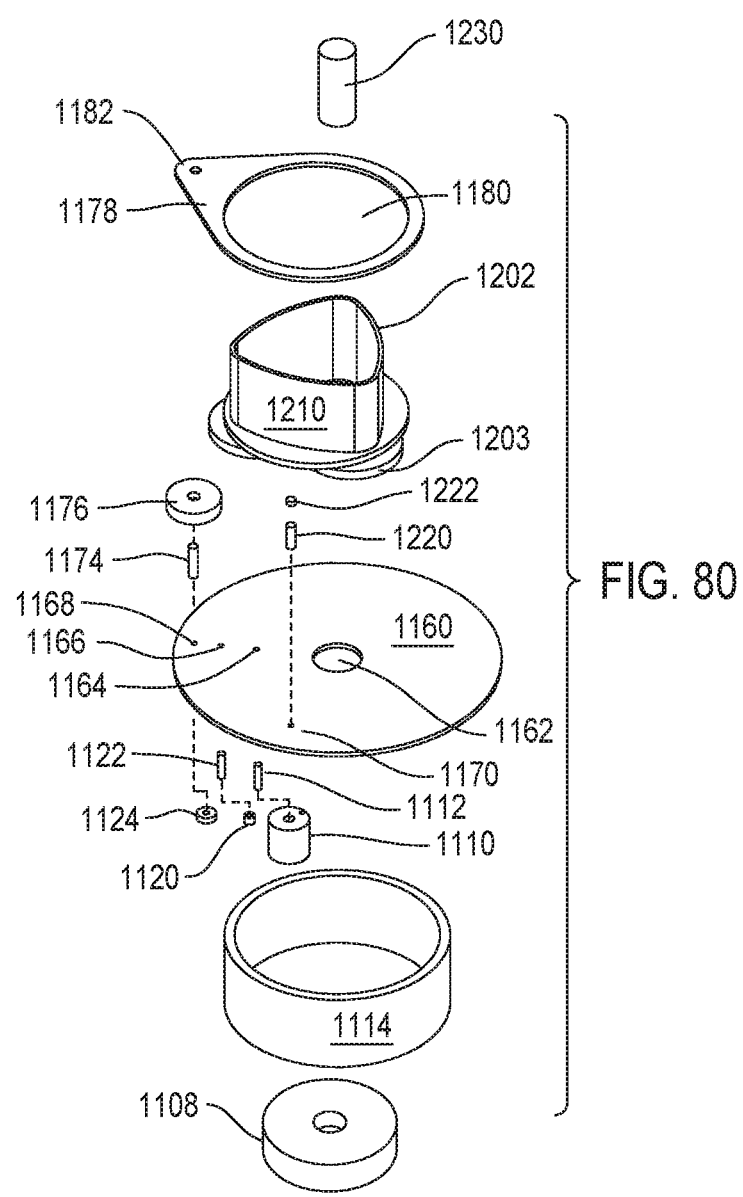

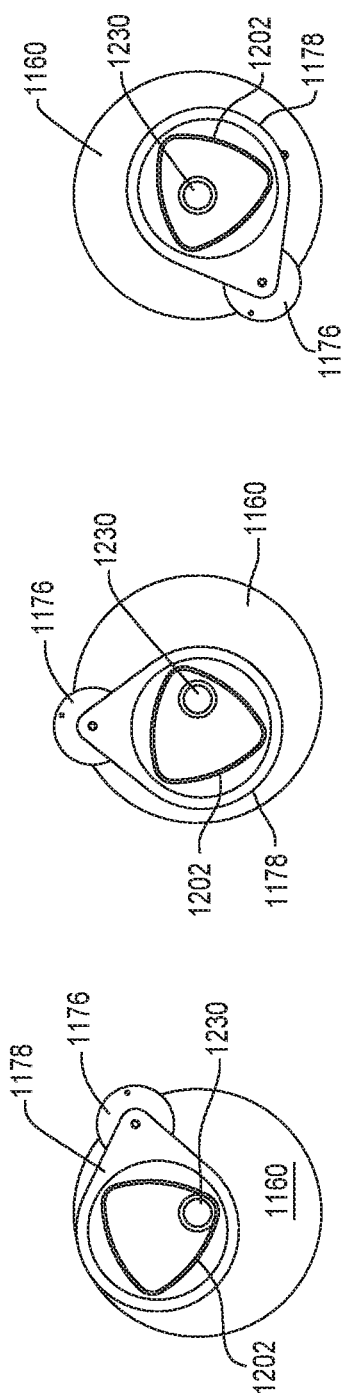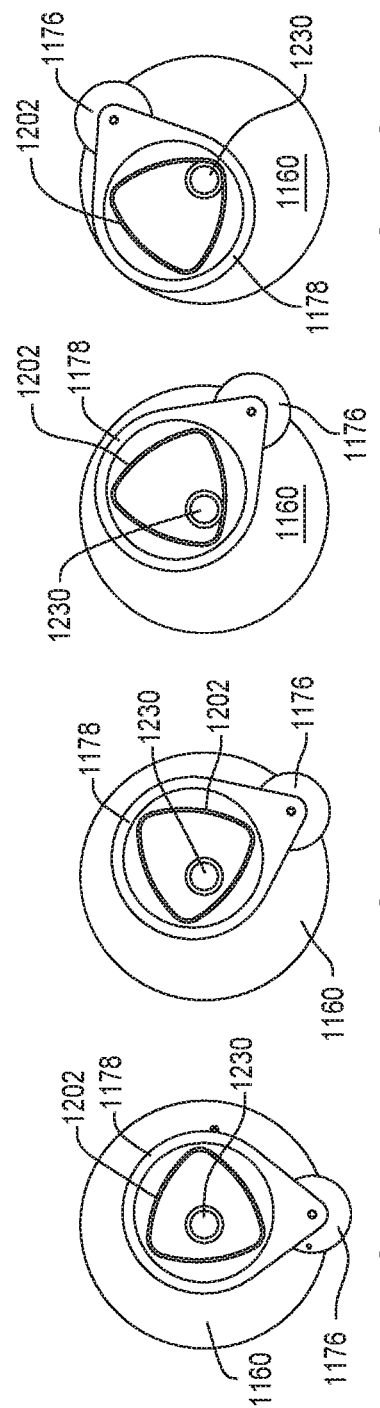

BONE CLEANER THAT REMOVES SOFT TISSUE BY PRESSING BONE STOCK AGAINST A CLEANING ELEMENT AND CLEARING THE BONE STOCK FROM THE CLEANING ELEMENT

CROSS-REFERENCE TO RELATED APPLICATIONS

This application is the National Stage of International Patent Application No. PCT/US2016/044386, filed on Jul. 28, 2016, which claims priority to Provisional Patent Application No. 62/197,780, filed on Jul. 28, 2015, the contents of which are incorporated herein by reference.

FIELD OF THE INVENTION

This invention is generally related to an assembly capable of cleaning bone by removing the soft tissue that surrounds the bone.

BACKGROUND OF THE INVENTION

In some surgical procedures, chip-sized bone is used as filler adjacent intact bone. For example, in a spinal fusion procedure, it is known to place a compound formed out of milled bone chips around implanted rods. The rods hold adjacent vertebrae in alignment. The compound serves as a lattice upon which tissues forming the vertebrae grow to form a foundation of bone around the rods. This foundation distributes the load imposed on the rods. Bone chips are also placed in the intervertebral disc space or into a cage positioned in the intervertebral disc space.

Milled bone is used as a filler/growth formation lattice in these procedures because the material, the proteins from which the bone is formed, serve as make-up material from which the blast cells of the adjacent living bone cells can form new bone. Accordingly, in a surgical procedure in which it is desirable to foster the growth of new bone, milled bone, to which supplemental material is sometimes added, is employed as filler in the spaces in which bone growth is desired. The individual pieces of milled bone are often referred to as bone chips.

The ideal source of bone stock for bone chips is the patient into whom the bone chips are to be packed. This is because the patient's own bone is less likely than donor bone to be rejected by the patient's immune system. Accordingly, in a procedure in which bone chips are required, bone stock is often harvested from one of the patient's bones that can afford to lose a small section of bone, typically between 0.25 and 3 cubic centimeters. Bone that is removed from the patient for transplant into another part of the patient is referred to as autograft bone. Often the autograph bone is harvested from the spinous process, vertebral facets, lamina or hip.

Converting autograft bone stock into bone chips is a two part process. In the first part of the process, the harvested bone stock is cleaned to remove the ligaments, muscle and other soft tissue that is not suitable for forming bone chips. The cleaned bone is then milled into bone chips. The Applicant's Assignee's U.S. Pat. Pub. No. US 2009/0118735/PCT Pub. No. WO 2009/061728, the contents of which are hereby incorporated by reference, discloses an electrically operated bone mill capable of converting bone stock into bone chips.

In a typical bone cleaning process, prior to milling the bone, surgical personnel manually clean the bone. Presently, surgical personnel perform this manual process using manual tools such as scalpels, curettes and/or rongeurs. It may take 15 minutes or more for surgical personnel to perform this task.

Moreover, to perform the cleaning process, the surgical personnel may need to firmly grasp the bone. Exerting such force on the bone may cause tearing of the gloves worn by the surgical personnel. Furthermore, the sharp cutting tools being used by the surgical personnel could cut or tear through the gloves. Such cutting or tearing through the gloves could result in the possibility that skin of the surgical personnel may come into direct contact with the bone. This contact can result in contamination of the bone.

The Applicant's US Pat. Pub. No. US 2012/0310243/PCT Pub. No. WO 2011/057088, explicitly incorporated herein by reference, discloses a number of different assemblies for cleaning bone. One of the assemblies disclosed in this document is a module that defines a chamber in which there is a fluted screw. This fluted screw is able to rotate in or adjacent the chamber. The screw is shaped so the flutes define cutting edges. The fluted screw is encased in a shaving tube. The shaving tube has a window through which the screw flutes are exposed. The portion of the shaving tube that defines the window is shaped to have its own cutting edges against the crew flutes. Bone is cleaned using the module of this assembly by pressing the bone against the fluted screw while rotating the screw. The soft tissue adhering to the bone is pressed against the flutes. The flute cutting edges and adjacent shaving tube cutting edges function as the cooperating scissor blades. These cutting edges cooperate to shear, cut, the soft tissue away from the bone.

The Applicant's US Pat. Pub. No. 2014/0303623/PCT Pub. No. WO 2013/102134, which is also explicitly incorporated herein by reference, discloses improvements to the above-described assembly for removing soft tissue from bone. One feature of the assembly disclosed in this document is that a pivoting arm surrounds the fluted screw and shaving tube assembly. A second feature of the assembly disclosed in this document is that the shaving tube, not just the fluted screw, rotate. When this bone cleaning assembly is actuated: the fluted screw continuously rotates; the shaving tube periodically rotates; and the arm pivots back and forth around the fluted screw and shaving tube. The periodic rotation of the shaving tube causes the tube to, at least momentarily, push the bone away from where the bone may be lodged between the fluted screw and the shaving tube. The pivoting motion of the arm tumbles the individual fragments of bone stock. Collectively these actions increase the extent to which soft tissue is removed from the individual fragments of bone stock.

The above described cleaning assemblies remove tissue that surrounds freshly harvested bone stock. However, it has been observed that a tail of the soft tissue can thread between the fluted screw and shaving tube. This tissue wraps around the inner surface of the shaving tube. If this event occurs, the bone stock is essentially considered caught between the fluted screw and shaving tube. This means that, even when the arm pivots back and forth, the arm is unable to dislodge the bone stock. The trapped bone stock prevents other tissue from moving against the interface between the rotating flutes and the adjacent shaving tube. Thus, should a piece of bone stock become so trapped, in order to complete the cleaning process it may be necessary to stop the cleaning module and remove the trapped bone stock. Once the trapped bone stock is cleared from the fluted screw, the module is reactivated.

However, having to interrupt the cleaning process to perform these processes reduces the utility of the cleaning module.

Furthermore owing to the nature of biological tissue, bone stock, especially freshly harvested bone stock, this material is very moist. This moisture is from the fluid such as blood, muscle and cartilage in the soft tissue harvested with the bone stock as well as the fluid contained in the bone itself. When the arm of the US Pat. Pub. No. US 2012/0310243/PCT Pub. No. WO 2011/057088 publications presses these bone fragments against the fluted screw and shaving tube, the liquid entrained in the bone and adjacent tissue can act like an adhesive. The material, collectively both the bone stock and soft tissue, can compress. A consequence of these materials having these properties is the bone, prior to cleaning, is known to adhere to the surfaces of arm. Once this event occurs, despite the pivotal motion of the arm, the bone stock may no longer tumble within the assembly. This tumbling is necessary to maximize the likelihood that the individual surfaces of the bone stock fragments are pressed against the fluted screw and shaving tube assembly.

It should also be understood that bone cleaning is only one process in the sequence of processes that need to be performed in order to place the bone in a state in which can be used as a fill material. As disclosed in the incorporated by reference U.S. Pat. Pub. No. US 2009/0118735, it is anticipated that after the bone stock is cleaned, the bone stock will be transferred into a bone mill. One could perform this transfer with a pair of forceps or tweezers transferring each fragment individually. Having to perform this one at a time transfer process can be time consuming. This would be in opposition to an objective of against the goal of modern objective is to perform a surgical procedure as quickly as possible. This to both minimize the time the internal tissue of the patient is exposed to the ambient environment and to minimize the time the patient is held under anesthesia. Furthermore, during the process of one at a time transfer of bone fragments with tweezers or forceps even the most careful individual can drop a fragment. Should this event occur, most likely the dropped fragment will no longer be a state in which the fragment would be contaminate free and therefore suitable for being reintroduced into the patient as bone chips.

Therefore, a better means to transfer the plural bone stock fragments is to pour the fragments directly from the bone cleaning module into the milling module. During the process of handling and tipping the cleaning module of the US Pat. Pub. No. 2014/0303623 publication to perform this pour, gravity can cause the position of the arm to shift. Sometimes, as a result of this shift, the cleaned bone stock fragments may simply become trapped against the arm. This requires the person responsible for cleaning and milling the bone to use tweezers or forceps to complete the bone transfer process. A more serious effect of the arm shifting position is that arm forces fragments to pop out of the bone cleaning module. If the fragments land on a surface that is not considered sufficiently sterile, the fragments will most likely be considered contaminated to the level at which they will no longer be suitable for use.

SUMMARY OF THE INVENTION

This invention is directed to a new and useful assembly for cleaning bone and milling the cleaned bone to produce bone chips. The assembly of this invention includes a bone cleaning module that, with little manual intervention, removes soft tissue from bone stock. The bone cleaning module of this invention is further designed to facilitate the efficient pour of the cleaned bone stock into the complementary milling module also part of the assembly of this invention. The assembly of this invention also includes a base unit. Both the cleaning module and milling module are removably attached to the base. Internal to the base unit is a motor. The motor powers the moving components internal to the bone cleaning module and the bone milling module. The base has few electrically actuated components that must withstand the rigors of a medical sterilization process.

In some versions of the invention, the bone cleaning module is configured to subject the bone stock being cleaned to plural cleaning cycles. Each cleaning cycle consists of plural distinct phases. At a minimum, the bone stock is subjected to a press phase and a clear phase that are interleaved with each other. In the press phase the bone stock is pressed against the cleaning elements. The cleaning elements are the components of the cleaning module that remove the soft tissue from the bone. During the press phase, some of the bone stock may be trapped by the cleaning elements. This is why the clear phase is executed. In the clear phase a component is urged against the cleaning elements to clear away, cut away the trapped bone stock. In some versions of the invention, the same component is urged against the bone stock during each of the press phase and the clear phase. More particularly, in many versions of the invention wherein the same component is urged toward the cleaning element in both the press phase and the clear phase, a first feature of the component is urged towards the cleaning element in the press phase and a second feature of the component is urged against the component in the clear phase.

In many versions of the invention, a single cleaning cycle consists of more than a press phase followed by a clear phase. In some versions of the invention, there is a tumble phase. In the tumble phase, the bone stock is tumbled. This tumbling is performed to ensure that during a cleaning processes the individual surfaces of the bone stock are each, in at least one press phase, urged against the cleaning elements. There may also be a sweep phase. During the sweep phase a component of the bone cleaner sweeps the bone stock to location adjacent the component that, during the subsequent press phase, urges the bone stock against the cleaning elements. In some versions of the invention a single cleaning cycle consists of a press phase, followed by tumble phase followed by a clear phase and that concludes with a sweep phase. In one construction of this invention of the invention, the components forming the bone cleaning module undergo a shift phase to transition from the tumble phase to the clear phase.

In some versions of the invention, simultaneously with the bone stock being cleared from the cleaning elements the bone stock is gathered as a precursor to the sweep phase.

In some versions of the invention, the cleaning elements internal to the bone cleaning element consist of a fluted screw and a shaving tube. The shaving tube defines at least one cutting edge that is located adjacent the cutting flutes of the fluted screw.

This invention is also directed to a bone cleaning module that includes separate void spaces. The bone stock to be cleaned is placed in first void space. This void space includes the cleaning elements that remove the soft tissue. Adjacent to and in communication with this first void space there is a second void space. A transfer assembly transfers the excised soft tissue away from the cleaning elements into the second void space. In some versions of the invention, one or more of the cleaning elements function as part of the transfer assembly. Thus, these elements both remove the soft tissue from the bone and transfer the removed soft tissue into the second void space.

BRIEF DESCRIPTION OF THE DRAWINGS

The invention is pointed out with particularity in the claims. The above and further features and benefits of this invention are understood from the following Detailed Description taken in conjunction with the accompanying drawings in which:

FIG. 4 is a cross sectional view of the interior of the assembly base;

FIG. 5 is an assembly diagram depicting how FIGS. 5A and 5B are arranged together to form an exploded view of components internal to the base of this invention;

FIG. 13 is a plan view of the top of the tube cam internal to the base;

FIG. 14 is a perspective view of the underside of the tube cam;

FIG. 19 is a perspective view of the top of the clutch input ring;

FIG. 20 is a perspective view of the underside of the clutch input ring;

FIG. 25 is a cross sectional view through the clutch taken along line 25-25 of FIG. 18;

FIG. 34 is an exploded view of the arm coupler and the assembly that pivots the arm coupler;

FIG. 35 is a perspective view of the shaft of the pivot assembly of FIG. 31;

FIG. 36 is a perspective view of the hat of the pivot assembly of FIG. 30;

FIG. 37 is a cross sectional view of the hat;

FIG. 38 is a perspective view of the arm coupler;

FIG. 39 is a cross sectional view of the arm coupler;

FIG. 40 is a perspective view of the crank arm of the pivot assembly;

FIG. 41 is a perspective view of the rocker arm of the pivot assembly

FIG. 67 is perspective view of the milling disk and attached coupling spindle of the milling module;

FIG. 68 is a perspective view of the top of the coupling spindle of the milling module;

FIG. 69 is a perspective view of the underside of the coupling spindle of the milling module;

FIG. 75 represents how, as a result of the rotation of the arm cam against the rocker arm, the rocker arm transitions through the sequential phases of a cleaning cycle.

FIG. 76 represents how, as a result of the rotation of the clutch cam against the pawl, the pawl transitions through the sequential phases of a cleaning cycle;

FIG. 80 is an exploded view of the assembly of FIG. 79;

FIGS. 85A through 85G are a sequence of plan views that illustrate how the cage engages in both rotation relative to the fluted screw and shaving tube and rotation around the longitudinal axis through the cage;

DETAILED DESCRIPTION

I. Overview

Figure 1:
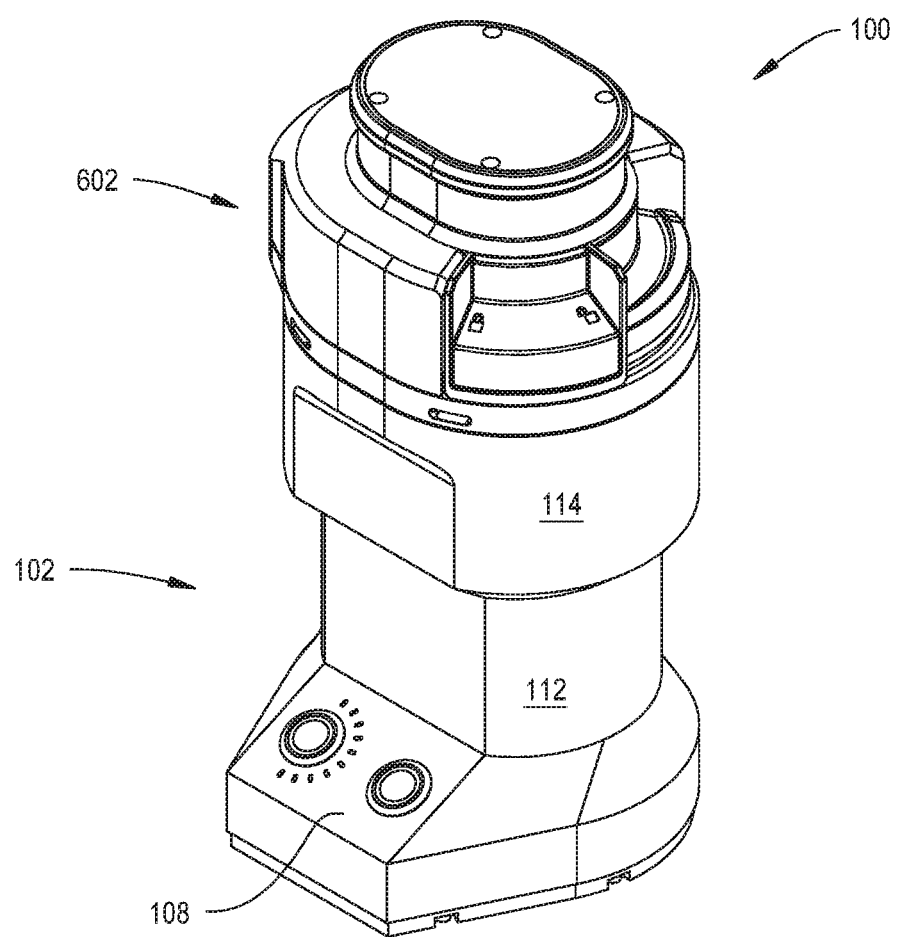
FIG. 1 is a perspective view of the base and cleaning module of the bone cleaning and milling assembly of this invention.
Figure 2:
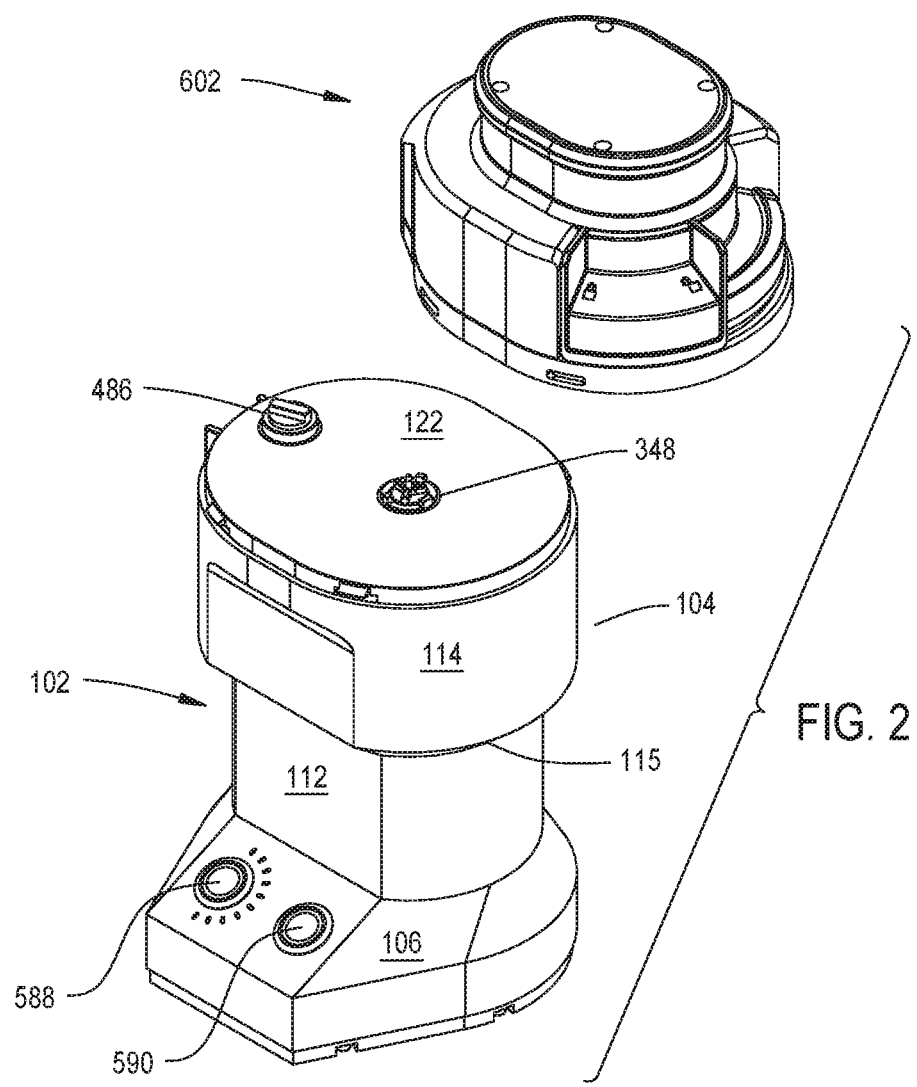
FIG. 2 is a perspective view of how the cleaning module is removably attached to the base.
Figure 3:
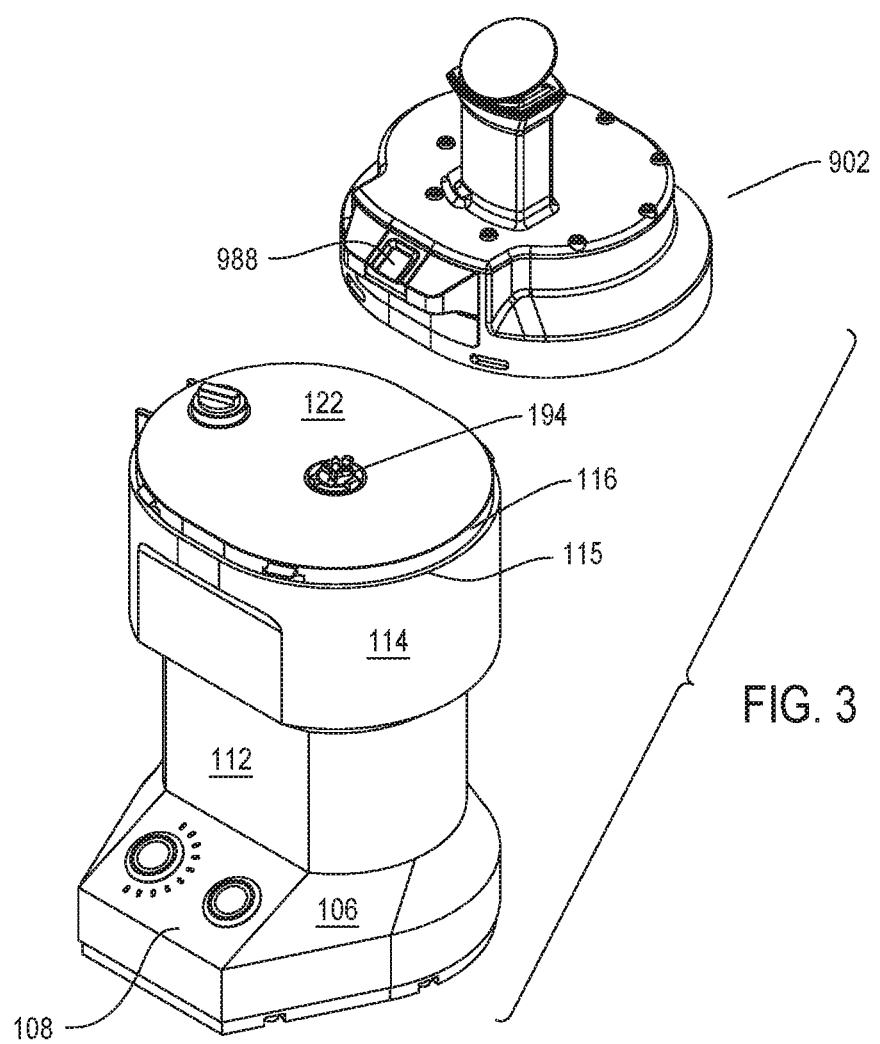
FIG. 3 is a perspective view of how a milling module of this invention is removably attached to the base.

FIGS. 1-3 illustrate the basic components of a bone cleaning and milling system 100 of this invention. System 100 includes a base 102 to which a bone cleaning module 602 is removably attached. Bone cleaning module 602 receives harvested bone stock. Upon actuation of the base 102, when the cleaning module 602 is attached, the components internal to the cleaning module 602 cooperate to remove soft tissue attached to the bone stock. As seen in FIG. 3, a second module, also part of system 100 and that is removably attached to the base 102, is a milling module 902. After the bone stock is cleaned, cleaning module 602 is removed from the base 102 and milling module 902 is attached to the base. The cleaned bone stock is transferred from the cleaning module 602 to the milling module 902. The assembly base 102 is again actuated. This results in the components internal to the milling module 902 converting the cleaned bone stock into smaller sized bone chips. The bone chips are available for use as fill in surgical procedure.

Internal to the base 102 is a motor 140 (FIG. 4). When a module 602 or 902 is connected to the base 102, a number of the moving components internal to the module are connected to the motor 140. By depressing a switch 588 or 590 on the base 102, the motor 140 is actuated. The actuation of the motor 140 results in the like actuation of the components internal to the module 602 or 902, that, respectively, cleans or mills the bone.

II. Assembly Base

The assembly base 102, as seen by reference to FIGS. 2 and 3, includes a shell 104 that is the outer body of the base. Shell 104 is formed have a pedestal 106 that, in terms of a gravity reference plane, is the bottommost portion of the shell. A neck 112 extends upwardly from pedestal 106. In cross sectional planes parallel to the gravity reference plane, neck 112 is smaller in area than the pedestal 106. The perimeter of the neck 112 is located inward of the outer perimeter of the pedestal. Shell 104 is further formed to so that pedestal 106 has a face panel 108 that tapers inwardly from the widest portion of the pedestal to is shaped to have a face panel 108 to neck 112.

Above the neck 112, shell 104 is shaped to have a head 114. The shell 104 is shaped so that the head 114 projects outwardly from the neck 112. In the depicted version of the invention, both the neck 112 and head 114 appear in cross section to be in the shape of a truncated oval. (The curved side sections of the neck and head each subtend an arc of less than 180°. A top plate 122 is the topmost structure panel of the head 114 and, by extension, of shell 104. Top plate 122 is recessed inwardly approximately 5 mm from the adjacent outer perimeter of the head 114. The top plate 122 has a rim 116 that extends circumferentially around and downwardly from the planar top surface of plate 122. A step 115 that extends inwardly from the outer surface of the head 114 to the to the rim functions as the transition surface between the outer perimeter of the head 114 and the top plate rim 115.

Figure 6:
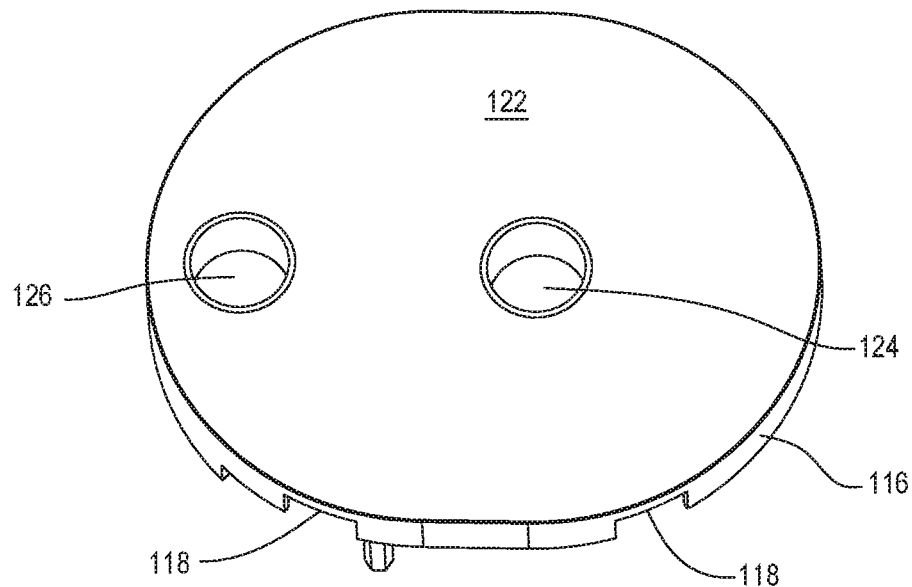
FIG. 6 is a perspective view of the top surface of the top plate of the shell of the base.
Figure 7:
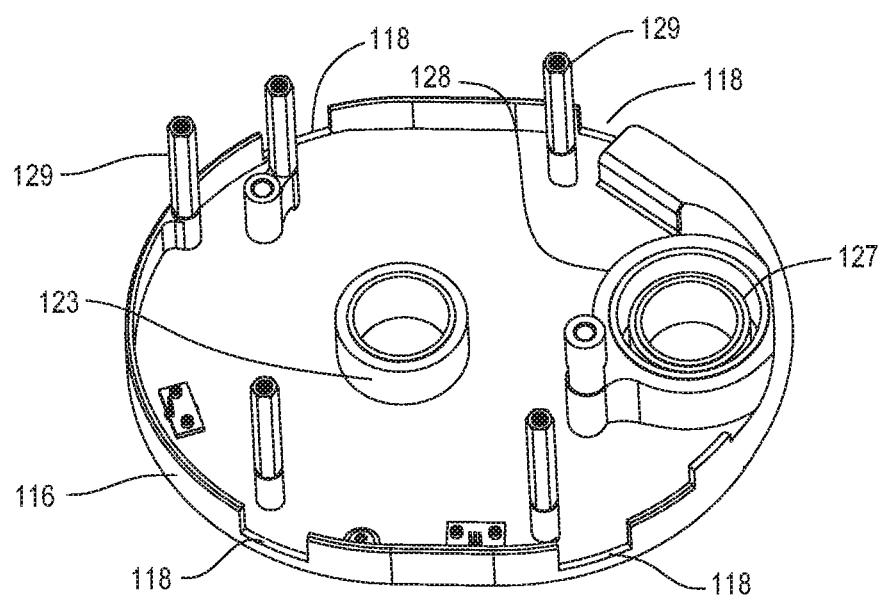
FIG. 7 is a perspective view of the under surface of the top plate of the shell.

The top plate 122 is further formed so there are four rectangular openings 118 in rim 116, openings identified in FIGS. 6 and 7. Openings 118 are located in the sections of the rim 116 adjacent the front and back edges of the top plate 122. The front edge of the top plate is understood to be the edge above shell base panel 108. The back edge is the edge furthest from the base panel 108.

Top plate 122 also has two openings, openings 124 and 126. Openings 124 and 126 are both centered on the major axis that extends side to side across the plate 122. Opening 124 is spaced to be approximately 1 cm away from the minor axis across the plate. The minor axis is the axis that extends from the midpoint of the panel front edge to the midpoint of the panel back edge. Opening 126 is located on the side of the plate minor axis opposite the side closest to opening 124. Opening 126 is located closer to the adjacent curved sides of the top plate 122 than the minor axis. Rim 116 is also shaped to define a slot 119 identified only in FIG. 43. Slot 119 extends through the curved side of the rim 116 located adjacent opening 126.

The top plate 122 is further formed to have sleeves 123, 127 and 128 that project downwardly from the undersurface of the planner portion of the plate 122. Sleeve 123 extends downwardly from the planar portion of the plate below opening 124. Sleeves 127 and 128 are concentric and extend downwardly from the planar portion of the plate below opening 126. Sleeve 127 is the inner most sleeve, the sleeve that defines a bore that extends inwardly from opening 126, (bore not identified). Sleeve 128 is the outermost sleeve and is spaced radially outwardly from sleeve 127. The top plate 122 is further formed so that sleeve 128 projects downwardly from the top plate 122 than sleeve 127. A number of posts 129 are also seen projecting downwardly from the undersurface of the top plate 122, two posts identified. The free ends of the posts are shown as having bores, (bores not identified). The bores are present for receiving fasteners as discussed below.

Two support members are statically mounted to the inside of shell 104. A first one of the support members is a motor mount 132 seen only in FIG. 4. Motor mount 132 is generally plate like in shape and is mounted in the neck 112 so as to be relatively close to the pedestal 106. The motor mount 132 is formed with a large through hole 134.

Figure 8:
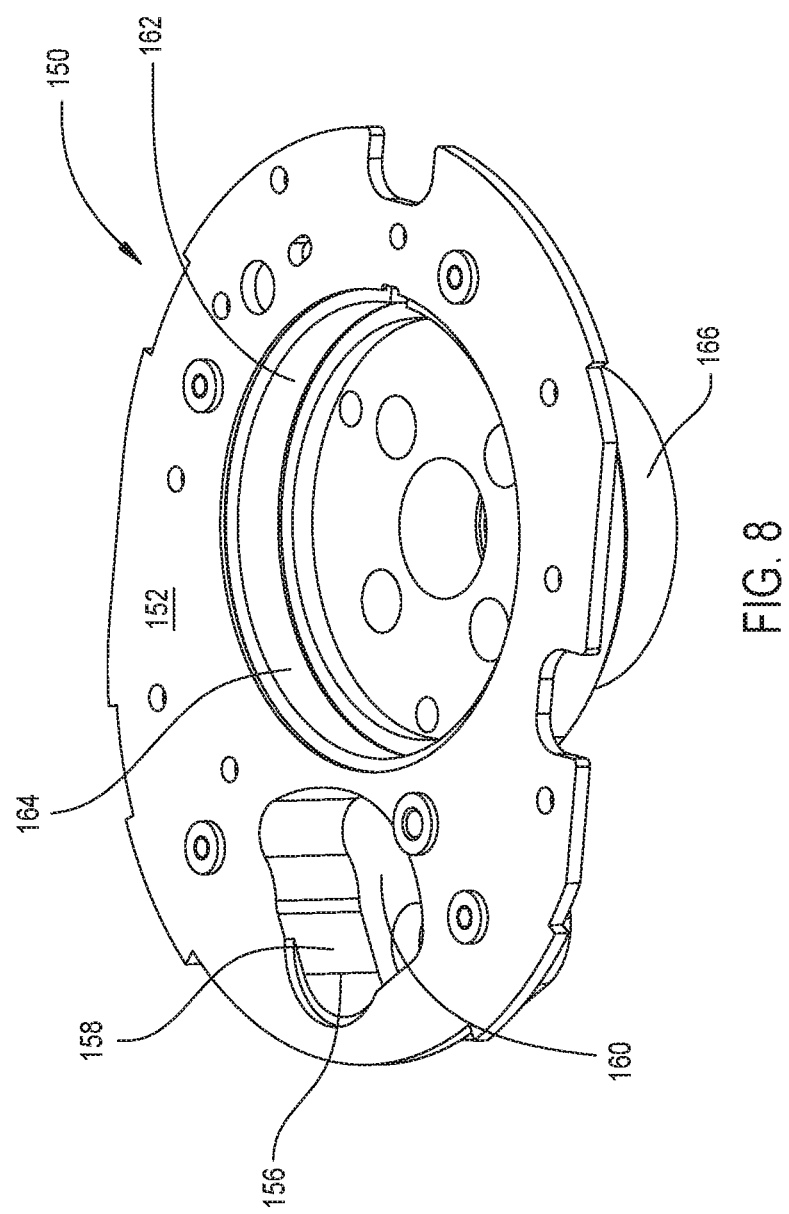
FIG. 8 is a perspective view of the inner plate internal to the shell.

A second support member, inner plate 150, is disposed in the shell head 114. Not identified is the step internal to the shell on which the outer perimeter of the inner plate 150 is seated. Plate 150, as seen best in FIG. 8, has a planar base 152. The plate 150 is further formed to have two voids, voids 156 and 162, that extend downwardly from openings in the base 152. The inner plate 150 is shaped so that the void 156 is approximately in the shape of triangle with rounded vertices. Inner plate 150 is formed so that void 156 is located below top plate opening 126. The base of void 156 is defined by a panel 160 that is located below base 152. A web 158 that extends downwardly from the base to connect the panel to the base defines the perimeter of the void 156. Void 162 is located to be coaxial with top plate opening 124. A boss 166 located below plate base 152 defines the base of void 162. A web 164, also part of plate 150, that extends between the plate base 152 to the boss 166 both holds the boss to the rest of the plate 150 and defines the outer perimeter of void 162.

Motor mount 132 and inner plate 150 are both seen as having a number of openings, through bores and closed end bores. Some of the openings and bores are surrounded by counterbores. Some of these bores open downwardly from circular islands that extend upwardly from the top directed surfaces of the motor mount 132 and plate base 152. These openings, bores, counterbores and islands are not identified. It should be understood that these bores and counterbores receive the pins and fasteners that hold the below discussed components of the assembly base 102 to the motor mount 132 and the inner plate 150. Some of the openings in the inner plate 150 are positioned to align with the posts 129 that extend downwardly from the top plate 122. Fasteners, (not illustrated) that extend through openings in the inner plate 150 and into the adjacent bores in the posts 129 hold the inner plate to the posts 129. Posts 129 thus connect the inner plate 150 to the top plate 122 so this sub-assembly, including the component mounted to the plate 122 and 150 can be fitted in the shell 104 as a single unit.

The motor 140 is mounted to the downwardly directed surface of the motor mount 132. Fasteners, not illustrated, hold the motor 140 to the mount 132. Motor 140 has a shaft 142, seen only in cross section in FIG. 10, that extends through an opening that extends through the mount 132. The opening through which shaft 142 extends is larger in diameter that the shaft. The motor 140 is mounted in shell 102 so that the motor shaft is coaxial with the opening 124 in the shell top plate 122.

Motor shaft 142 is connected to a gear train 144 the outer shell of which is seen in the drawings. The gear train 144 is seated in opening 134 internal to the motor mount 132 so as to be disposed over the portion of the motor 140 located immediately below the opening 134. Gear train 144 typically consists of a planetary gear assembly that steps down the speed of the rotational motion of the motor shaft 142. The rotational motion of the gear train is output through a shaft 145 that extends upwardly from the outer shell of the gear train. In one version of the invention, motor 140 is designed so that when actuated, rotate at a speed of the motor shaft 142 between 2500 to 5500 RPM. Gear train 144 is configured so that the speed ratio between the motor shaft 142 and gear train shaft 145 is between 5:1 and 90:1.

The base of gear train 144 is attached directly to face of the housing of motor 140. The base of the gear train 144 is thus seated in the opening in the motor mount 132 through which the motor shaft 142 extends. The top surface of the gear train 144 is mounted to the undersurface of boss 166 integral with plate 152. In the illustrated version of the invention a plate 151 is located between the top of the gear train 144 and the underside of the boss 166. The plate 151 may be formed from elastomeric material to cushion the vibrations of the motor. Fasteners 147, one fastener identified in FIG. 4, that extends through plate 151 into the top of the gear train holds the plate to the gear train. Gear train 144 has a shaft 145 that extends through an opening in the boss 166 so as to extend into void 162 internal to the plate 150. The gear train shaft 145 is generally cylindrical in shape. A key 146, identified in FIG. 9, extends outwardly from the cylindrical surface of the shaft 145. The key 146 extends longitudinally along the shaft 145.

Figure 9:
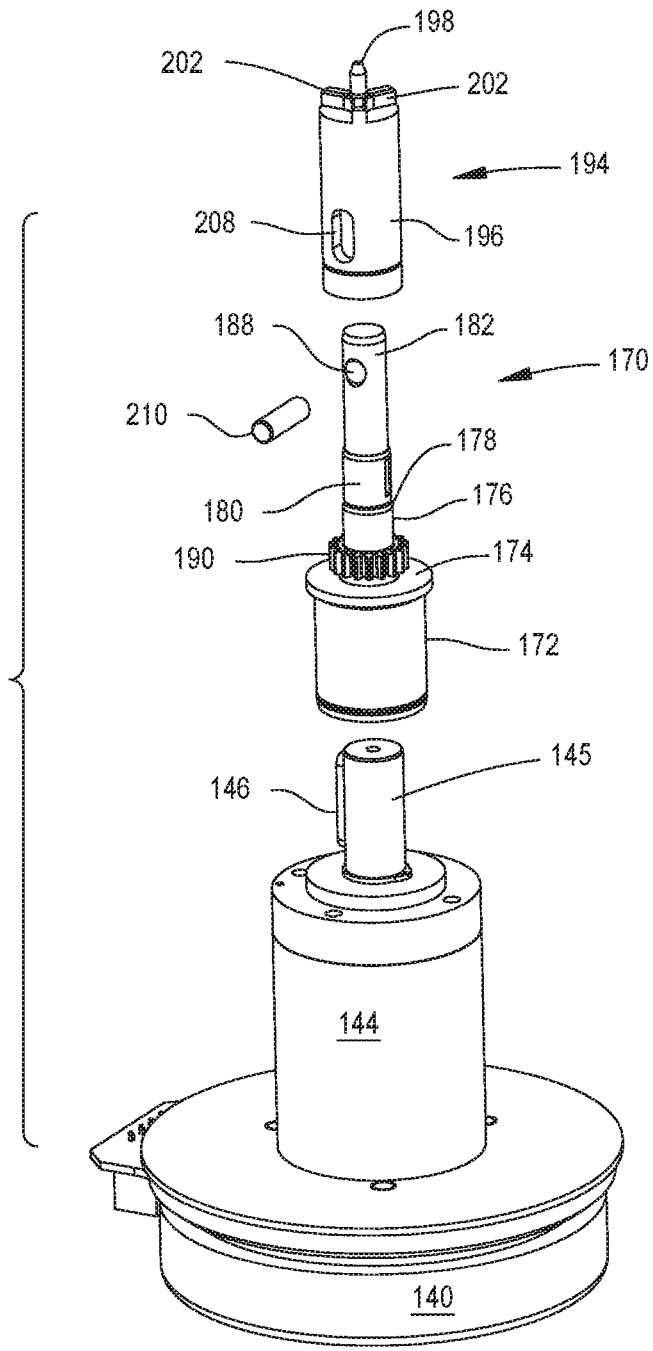
FIG. 9 is an exploded view of the motor and attached primary coupler that are part of the base.
Figure 10:
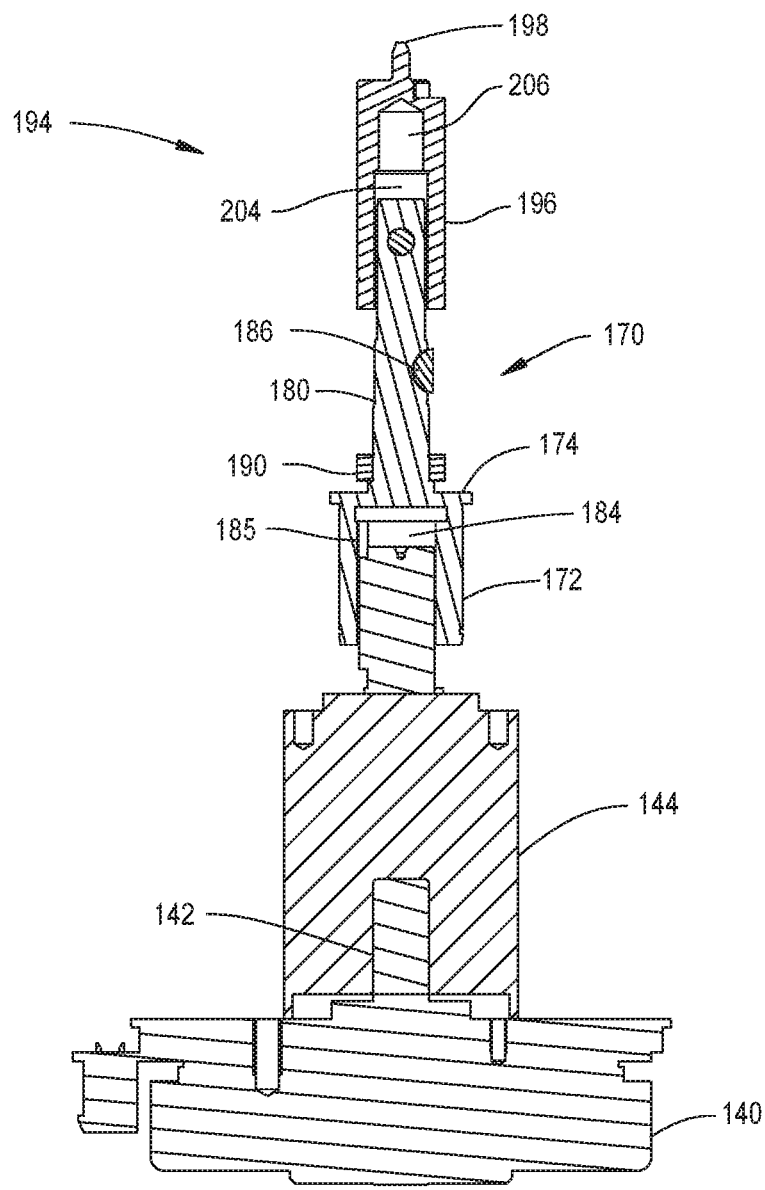
FIG. 10 is a cross sectional view of the motor and primary coupler.

A spindle 170, seen best in FIGS. 9 and 10, is mounted to the gear train shaft 145 to rotate in unison with shaft 145. Spindle 170 includes a cylindrical base 172. A cylindrical trunk 176 extends upwardly from the base 172. Trunk 176 is coaxial with the base 172 and has a diameter less than that of the base. Adjacent where the trunk emerges from the base 172, spindle 170 is shaped to have a step 174 that extends around the trunk. Above the trunk 176, the spindle has a neck 180. Neck 180 is coaxial with and smaller in diameter than the trunk 176. A step 178, thus extends circumferentially radially outwardly from the bottom of the neck 180 so as to function as the transition surface between the trunk 176 and the neck 180. The topmost portion of the spindle is head 182. The head 182 is coaxial with and has a smaller diameter than the spindle neck 180.

The spindle 170 is further formed to have a closed end bore 184 that extends upwardly from the bottom of base 172. Bore 184 is coaxial with the base 172. An indentation 186 extends inwardly from the outer surface of the spindle neck 180. Spindle 170 is further formed so a bore 188 extends longitudinally through the spindle head 182. In the illustrated version of the invention, bore 188 is centered on axis that is perpendicular to the center radial line that extends inwardly through indentation 186 to the longitudinal axis of the spindle 170.

Spindle 170 is seated over the gear train 144 so the gear train shaft 145 is seated in spindle bore 184. Key 146 seats in a slot 185 internal to the spindle that extends outwardly from outer perimeter of bore 184. This key in slot arrangement ensures that the gear train shaft 145 and spindle 170 rotates as a single unit.

A gear 190 is disposed around spindle trunk 176 to rotate in unison with the spindle 170. The gear 170 sits on step 174. The teeth of the gear 190 are located both above the spindle base 172 and radially outwardly from step 174 (gear teeth not illustrated).

A primary coupler 194 is mounted to spindle 170. The primary coupler 194 includes a cylindrical base 196. A pin 198 extends upwardly from the top of base 196. Also disposed on the top of base 196 are three equangularly spaced apart teeth 202. Each tooth 202 is an elongated member that projects radially outwardly from the pin 198 and extends upwardly from the top of the base 196. Primary coupler 194 is formed so that pin 198 projects above the teeth 202.

The primary coupler 194 is further formed to have a bore 204 that extends upwardly from the bottom of base 196. Bore 204 has a diameter that allows the spindle head 182 to closely slip fit in the in the bore 204. Bore 204 opens into a closed end bore 206 that extends towards the top of the base 196. The primary coupler 194 is formed so that bore 206 has a diameter that is less than the diameter of bore 204. More particularly, the coupler 194 is formed so that bore 206 has a diameter that is less than the diameter of the head 182 of stem 170. Coupler 194 is further formed to have two diametrically opposed oval shaped openings 208 that extends inwardly from the outer cylindrical surface of base 196 (one opening 208 seen in FIG. 10). Openings 208 extend into bore 204.

The primary coupler 194 is fitted to the rest of the assembly base 102 so that spindle head 182 is disposed in coupler bore 204. A pin 210 extends through coupler openings 208 and into bore 188 internal to the spindle head 182. Pin 210 holds the primary coupler 194 to the spindle 170 so the coupler rotates in unison with the spindle and is able to move longitudinally along the longitudinal axis through the spindle. The primary coupler is positioned so that the top of the coupler base 196 extends through top plate opening 124. Coupler pin 198 and teeth 202 are located above the shell top plate 122.

Figure 5A:
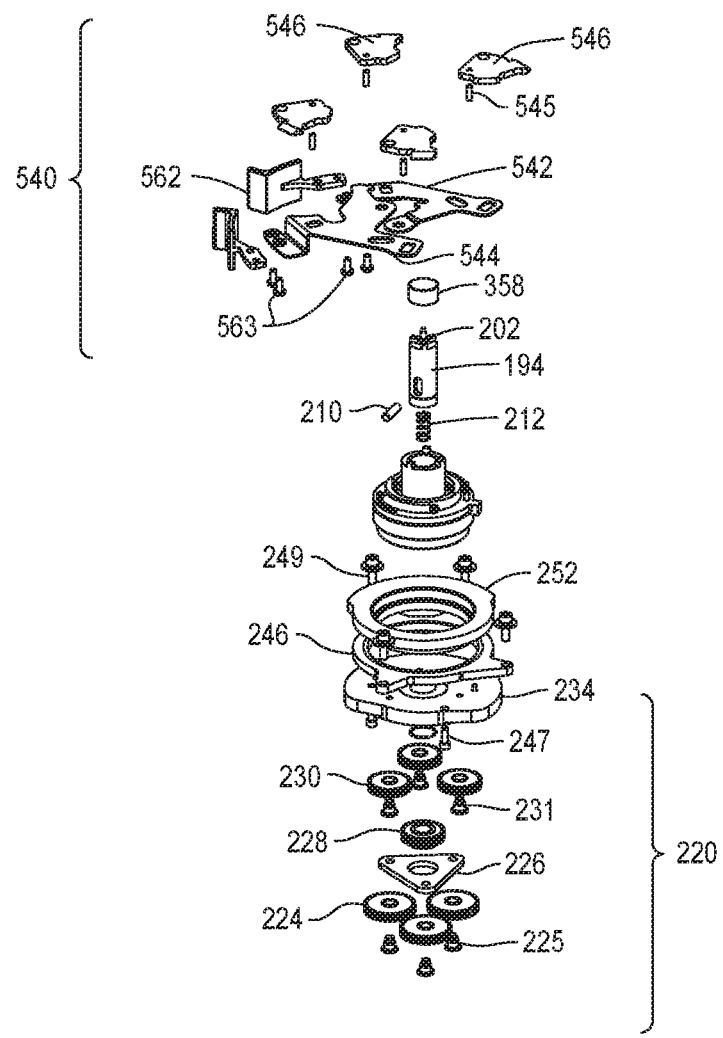

A spring 212, seen in FIG. 5A, is disposed in coupler bore 208. Spring 212 provides a bias force that normally displaces the coupler so the coupler pin 198 and teeth 202 are spaced away from the shell top plate 122. The upward movement of the coupler 194 is limited by the portion of the coupler that defines the bottom of opening 208 abutting pin 210. Downward movement of the coupler is limited by the step internal to the coupler defining the transition from bore 204 to bore 208 abutting the top of spindle head 182

Figure 11:
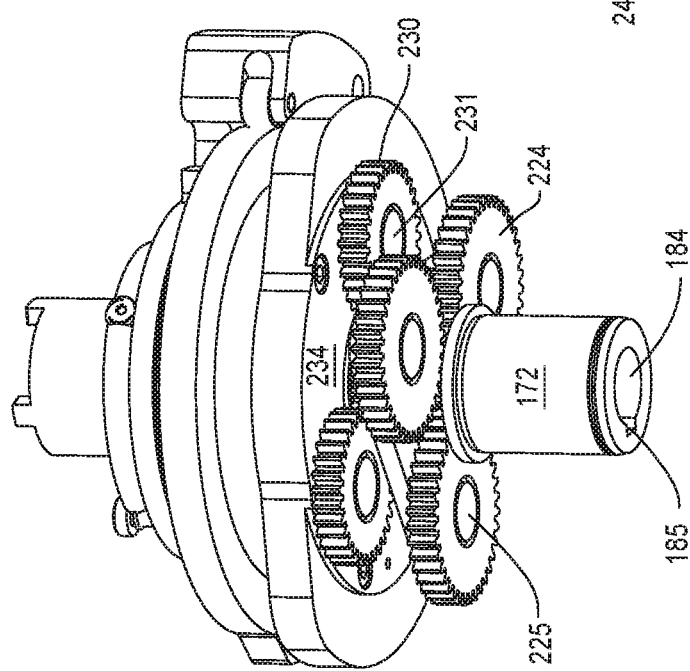
FIG. 11 is a perspective view of the planetary gear assembly disposed around the main spindle internal to the base.

A secondary gear train 220, the components of which are best seen in FIGS. 5A, 5B and 11, is disposed around the neck 180 of spindle 170. The secondary gear train 220 includes a ring gear 222 disposed in void 162 internal to inner plate 150. The gear 222 is positioned so that the outer surface of the gear is disposed against the inner surface of web 164. The teeth of the ring gear, (teeth not identified) extend inwardly towards the center of void 162. Not illustrated is the snap ring that is disposed around and above the outer perimeter of the ring gear 222. The snap ring protrudes outwardly from a groove in web 164. The snap ring holds ring gear 222 in void 162.

Gear train 220 also includes a first set of planet gears, gears 224. Gears 224 are rotatably mounted to a carrier 226 by pins 225. Gears 224 engage both gear 190 and the teeth of ring gear 222. Carrier 226 has its own sun gear 228 that surrounds the neck 176 of spindle 170. The inner diameter of sun gear 228 is spaced radially outwardly from the spindle 170.

Three planet gears 230, also part of the secondary gear train 220, extend between ring gear 222 and sun gear 228. Planet gears 230 are rotatably mounted to the below described arm cam 234 by pins 231. The secondary gear train is designed to cause the arm cam and attached components to rotate at a speed less than that of the rotation speed of the spindle. In some versions of the invention, the speed ratio between spindle 170 and the arm cam 234 is between 12:1 and 24:1.

Figure 12:
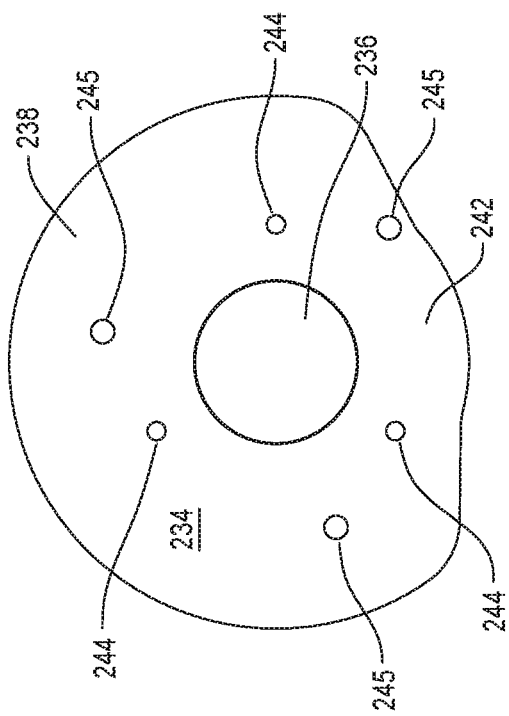
FIG. 12 is a plan view of the arm cam internal to the base.

Arm cam 234, seen best in FIG. 12, is a generally disc shaped component. The arm cam 234 is formed with a center opening 236. Opening 236 is dimensioned so as to have a diameter greater than that of the spindle neck 182. The arm cam has two lobes. An outer lobe, lobe 238, has an outer perimeter that is spaced relatively far away from the center of cam 234. Outer lobe 238 subtends an arc that extends more than 180° around the outside of the cam 234. In some versions of the invention the outer lobe subtends an arc of between 190 and 240°. The second lobe is inner lobe 242. Inner lobe 242 has an outer perimeter that is spaced radially inward from outer perimeter of the outer lobe 238. Inner lobe 242 subtends an angle around the cam 234 between 20 and 60°. Not identified are the transition surfaces between each end of the outer lobe 238 and the adjacent end of the inner lobe 242.

The arm cam 234 is formed with two sets of through bores that extend side to side through the cam and that are spaced radially outwardly from the opening 236. A first set of bores are three equangularly spaced apart bores 244. Bores 244 receive the pins 231 that rotatably hold planet gears 230 to the arm cam. A second set of bores are three equangularly spaced apart bores 245. Bores 245 are larger in diameter than bores 244 angularly offset from bores 244 and spaced slightly radially outwardly from bores 244. Bores 245 receive the fastening pins that hold the below described tube cam 252 to the arm cam 234 (fastening pins not illustrated).

The tube cam 252 now described by reference to FIGS. 13 and 14 is mounted the arm cam 234. The tube cam 252 is a single piece component that includes a ring shaped skirt 254. A rim 256 is disposed above the skirt 254 and extends radially outwardly from the skirt. Tube cam 252 is formed so rim 256 has inner and outer lobes 258 and 262, respectively. Inner lobe 258 has an outer surface 260 that, in terms of radial distance, is located relatively close to the center of the cam. The inner lobe 258 subtends an arc that subtends an arc of greater than 180° around the cam 252. In some versions of the invention the inner lobe 258 subtends an arc between 185° and 205° Outer lobe 262 is shaped to have an outer surface 264 located further from the center axis of the cam 252 than surface 260 of the inner lobe 252. Tube cam 252 is formed so that the cam surface 264 subtends an arc of between 40° and 140° around the center of the cam. Not identified are the transition surfaces between outer surface 260 and outer surface 264.

Tube cam 252 is formed so that the skirt 254 and rim 262 collectively define an opening 266 that extends through the center of the cam. The tube cam is further formed to define a step 268 that projects into and extends circumferentially around opening 266. Step 268 is located below the top surface of rim 262. Three equangularly spaced apart bores 270, identified in FIG. 14, extend from the bottom of skirt 254 to the top of step 268. Upon assembly of base 102, tube cam bores 270 are in registration with arm cam bores 245. Bores 270 receive the fastening pins that hold the shave cam 252 to the arm cam 234.

Figure 15:
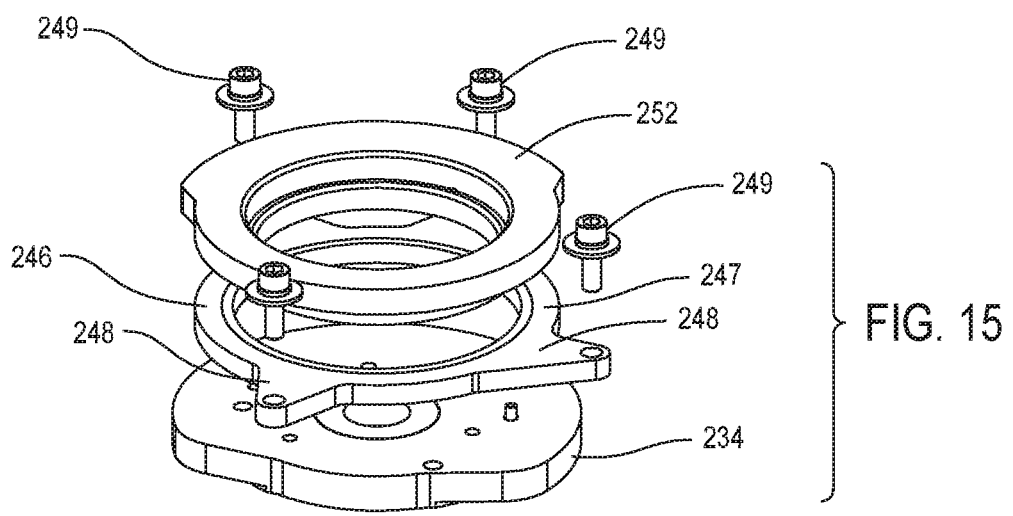
FIG. 15 is an exploded view showing how the balance collar is sandwiched between the arm cam and the tube cam.

As best seen in FIG. 15, a balance collar 246 is sandwiched between the arm cam 234 and the tube cam 252. The balance collar 246 includes a center ring 247. Assembly 102 is constructed so that the skirt 254 is disposed in and rotates within the void defined by ring 247. Four tabs 248, two seen in FIG. 15, project outwardly from the center ring 247. A fastener 249, three fasteners identified, extends through each of the tabs 248. The fasteners 249 are secured to base 152 of the inner plate 150. Fasteners 249 thus hold the balance collar 246 static to the assembly base 102. Tabs 248 and fasteners 249 are located radially outwardly of the arm cam 234. Thus, the presence of the static balance collar 246 does not inhibit the rotation of the arm cam 234 and the tube cam 252.

Figure 16:
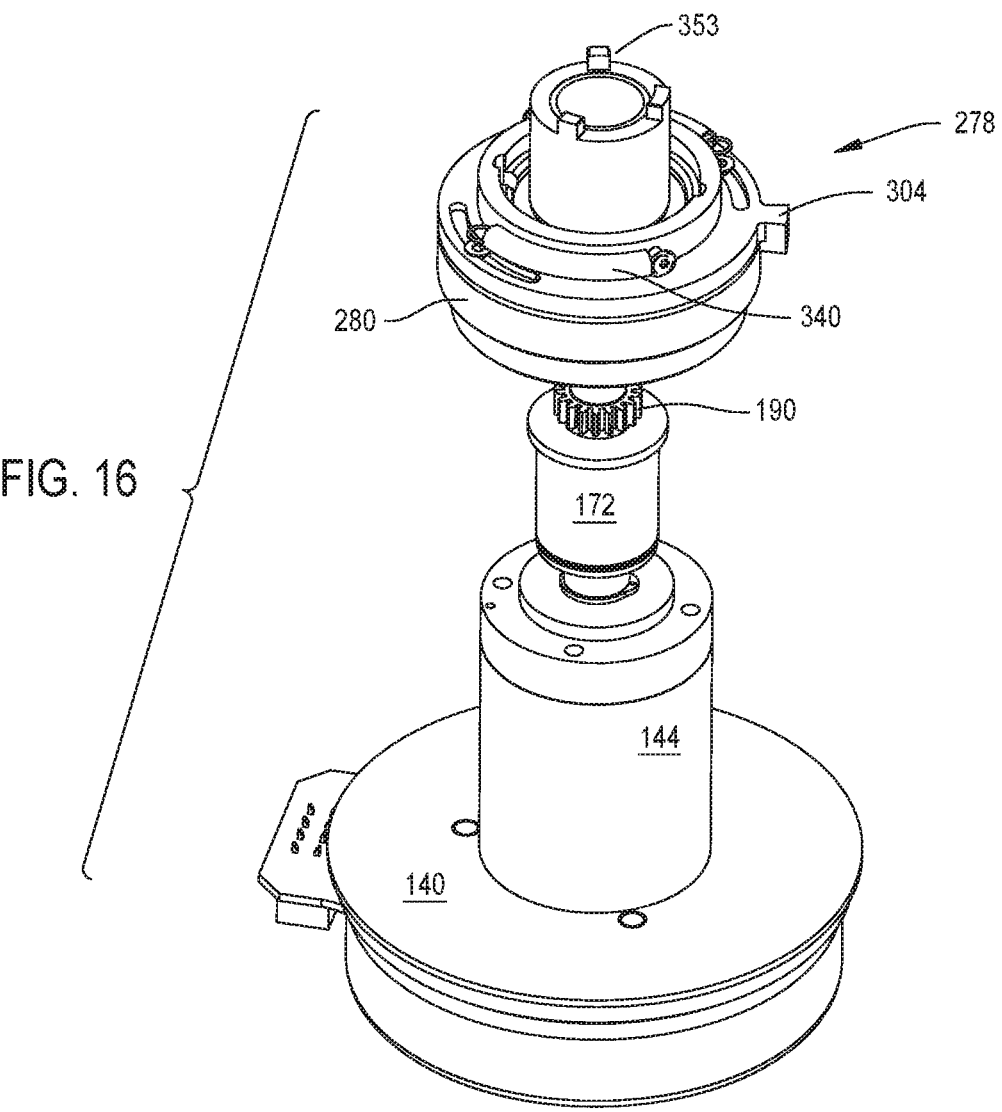
FIG. 16 is a perspective view how a clutch and tube coupler are disposed around the main spindle.
Figure 17:
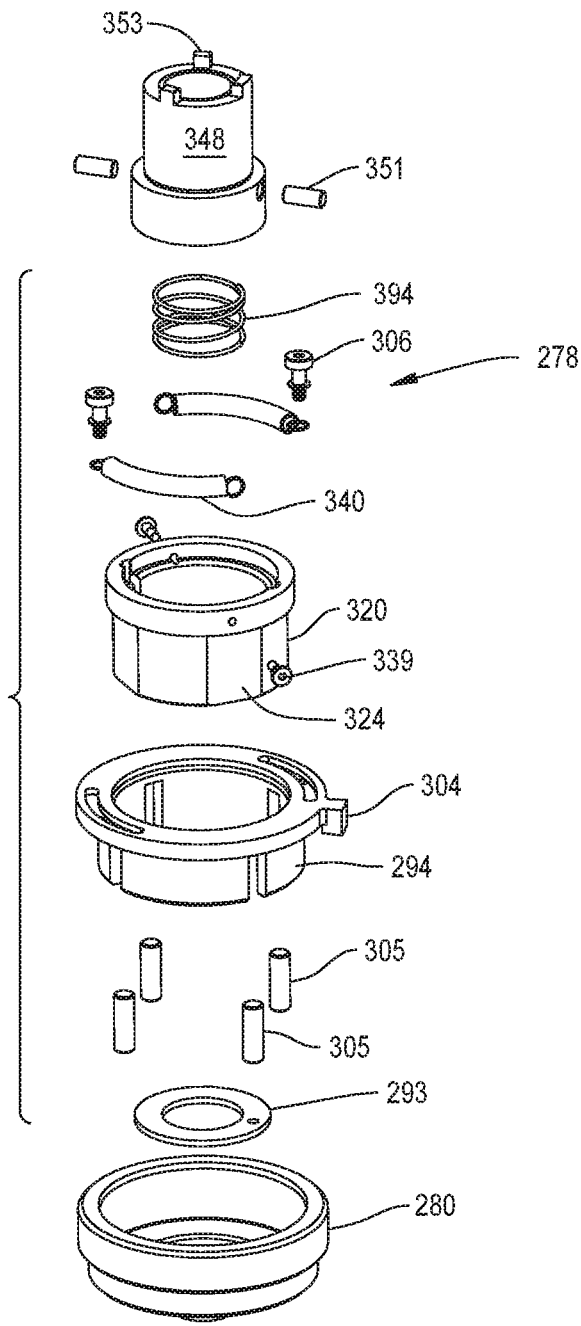
FIG. 17 is an exploded view of the clutch and tube coupler.
Figure 18:
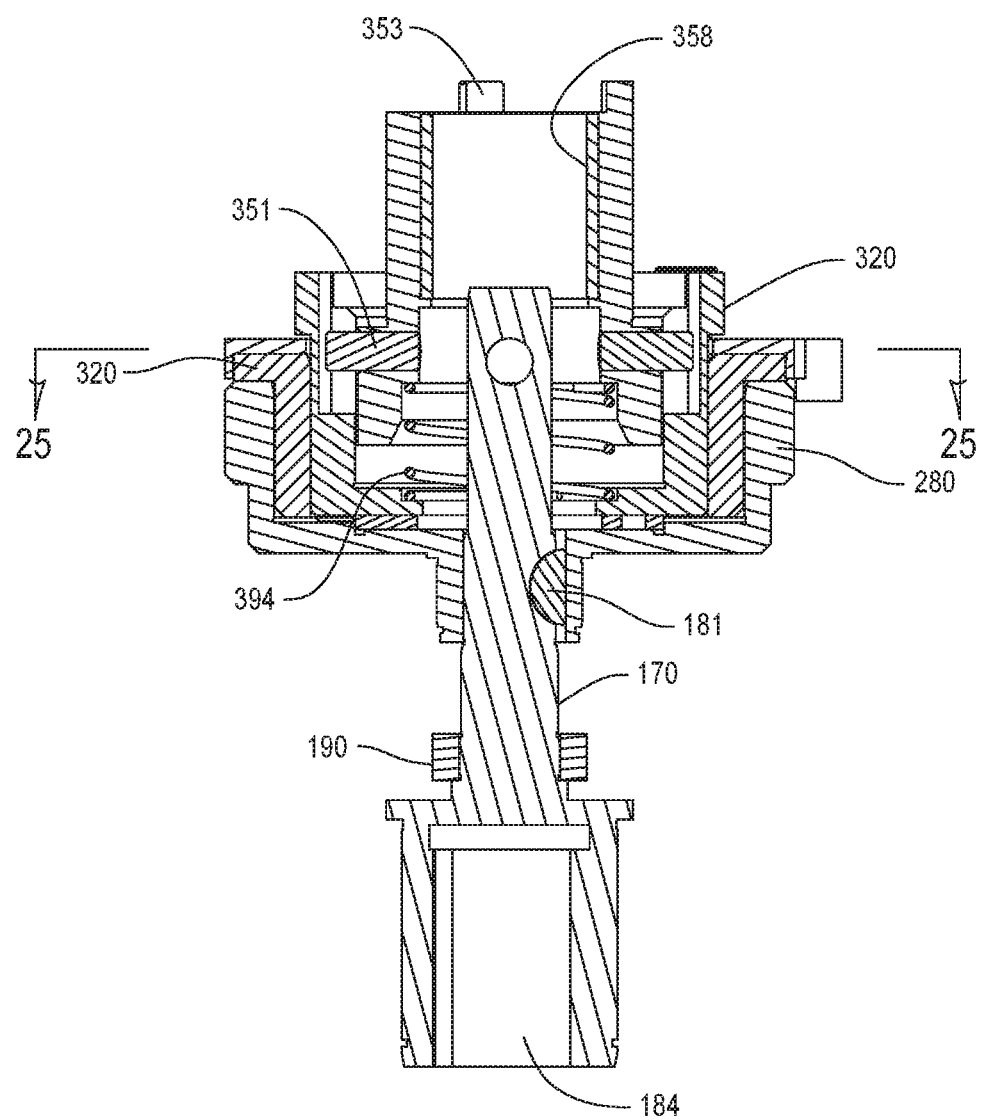
FIG. 18 is a cross sectional view of the clutch and tube coupler.

A clutch assembly 278, seen best in FIGS. 16-18, is disposed above the tube cam 252 around the spindle 170. In FIGS. 16 and 18, the arm cam 234, the shaving cam 252 and the gear assemblies below the arm cam 234 are not seen to simplify the Figures.

The clutch assembly 278 includes an input ring 280. The input ring 280, seen best in FIGS. 19 and 20, has a tubular shaped stem 282. Stem 282 is formed with a through bore 284 and is dimensioned to tightly fit around the neck 180 of spindle. A slot 285 extends outwardly from the inner surface of the stem 282 that defines bore 284. Slot 285 is thus contiguous with bore 284. Input ring 280 is further formed to have a head 286 that extends radially outwardly from the top of stem 282. Head 286 is shown to have a ring (not identified) that protrudes outwardly from the outer surface of the head. This ring provides mechanical strength to the input ring 280. The head 286 is formed to define in the center of the head are circularly shaped void 288. Void 288 is contiguous with and larger in diameter than bore 284 that extends through stem 282. The head 286 is further formed so that as to have a recessed surface 290 that surrounds the opening into bore 284

The input ring 280 is fitted to spindle 270 so the ring stem 284 is disposed over the spindle neck 180. Stem 284 is disposed within opening 236 of the arm cam 234. The lower portion of the ring head 286 is disposed within opening 266 of the tube cam. A key 181, identified only in FIG. 18, extends outwardly from the spindle neck 180. Key 181 seats in slot 285 internal to the input ring 280. This key-in-slot arrangement ensures that spindle 170 and the clutch output ring rotate as a single piece unit.

Figure 22:
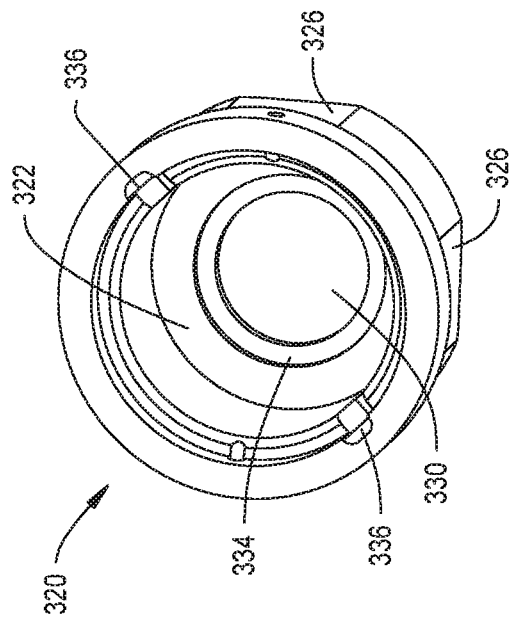
FIG. 22 is a second perspective view of the top of the clutch output ring.
Figure 21:
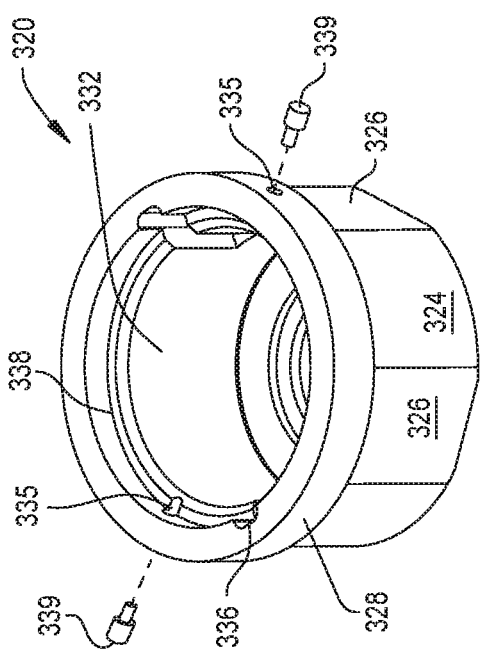
FIG. 21 is a perspective view of the top of the clutch output ring.

An output ring 320, also part of clutch 278, seen best in FIGS. 21 and 22, is disposed in the input ring void 286 and projects above the input ring 280. The input ring 320 has a circular base 322. A generally tube-shaped sleeve 324 extends upwardly from the outer perimeter of base 322. While the inner and outer surfaces of sleeve 324 are generally cylindrical in shape, these surfaces are not completely cylindrical. Output ring 320 is formed so as define four equangularly spaced apart flats 326 along the outer surface of sleeve 324, two flats identified in FIGS. 21 and 22. Flats 326 are located within the circular area defined by the curved outer surface of the sleeve 324. Relative to the top-to-bottom longitudinal axis through the outer ring 320, each flat 326 subtends and angle between 50° and 90°. The outer ring 320 is further formed to have a circular lip 328 that is disposed above sleeve 324. The ring 320 is formed so that lip 328 projects radially outwardly beyond the outer surfaces of sleeve 324.

The output ring 320 is further formed so there is an opening 330 in base 322. Opening 330 is of sufficient diameter so that, when the assembly base 102 is assembled, there is a clearance between the outer surface of the spindle head 182 and the surface of ring base 322 that defines the outer perimeter of the opening 330. Sleeve 324 and lip 328 collectively define a void 332 that is contiguous with opening 330. The base 322 is further formed to have a recessed surface 334 in the top surface of the base. Recessed surface 334 extends circumferentially around opening 330 and is defines the lowest section of void 332.

Output ring 320 is further formed to have two notches 336 that extend radially outwardly from the inner surfaces of sleeve 324 and lip 328. Notches 336 extend longitudinally from the top face of ring 320 through the ring and partially through the sleeve 324. The notches 336 are diametrically opposed to each other relative to the longitudinal axis through the outer ring 320. The outer ring is further formed so lip 328 is shaped to define a step 338 that extends inwardly around the inner perimeter of the lip. Step 338 is located below the top directed face of lip 328. The notches 336 intersect the step 338.

Two coaxial bores 335, identified only in FIG. 21, extend laterally through the lip 328 of the output ring 320. Bores 335 intersect step 338. When the clutch 278 is assembled, a pin 339 is seated in each of the bores 335. Each pin 339 has a head that is located radially outwardly from the adjacent cylindrical surface of lip 328 of the output ring 320.

Figure 24:
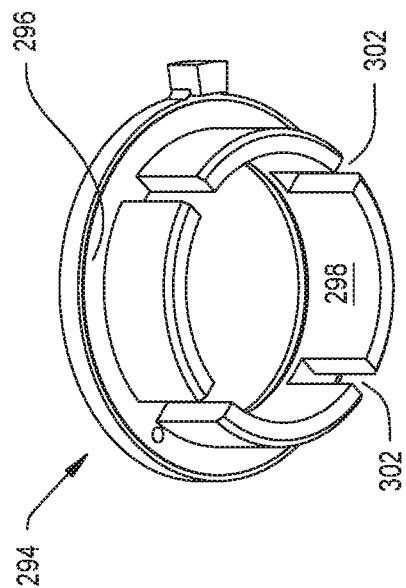
FIG. 24 is a perspective view of the underside of the clutch cage.
Figure 23:
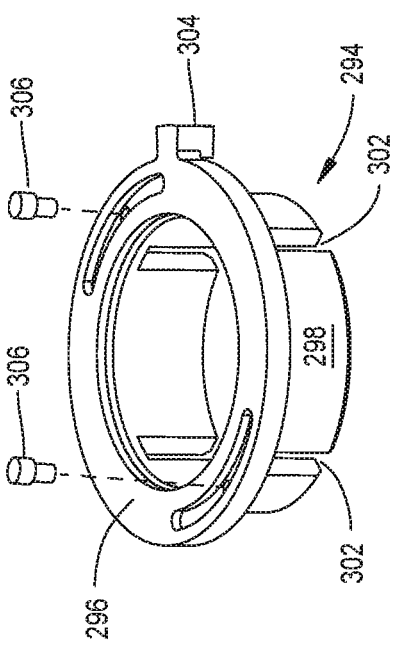
FIG. 23 is a perspective view of the top of the clutch cage.

A cage 294, seen best in FIGS. 23 and 24, also part of clutch 278, is disposed between input ring 280 and output ring 320. The cage 294 includes a ring 296. A generally tube shaped skirt 298 extends downwardly from the ring 296. Cage 294 is formed so the inner surface of skirt 298 is flush with the inner surface of ring 296. The outer surface of skirt 298 is located radially inwardly from the outer perimeter of ring 296. The cage is further formed so there are four equangularly spaced apart slots 302 in the skirt 298, two slots identified. Each slot 302 extends upwardly from the base of the skirt 298, the end of the skirt opposite the end adjacent ring 296. Each slot 302 is centered along a major axis that is parallel to the top to bottom longitudinal axis through the cage 294. The cage 294 is formed so that slots 302 terminate at a location spaced below where the skirt 298 extends downwardly from ring 296.

Cage 294 is further formed so a tab 304 projects outwardly from the outer perimeter of the ring 296. Two pins 306, identified in FIG. 23, extend upwardly from the top facing surface of ring 296. Pins 306 are diametrically opposed to each other relative to the longitudinal axis through the cage 294. Not identified are closed end bores in the top surface of the ring in which the pins are seated.

In some versions of the invention, cage 294 is formed from two components that are assembled together to function as a single piece unit. This is facilitates the selective positioning of the tab 304 relative to the pins 306 during the manufacturing process.

When clutch 270 is assembled, the output ring 320 is seated in void 288 of the input ring 280. Base 322 of the output ring is seated on a low friction washer 293 seated over recessed surface 290 of the input ring 280. The presence of washer 293 facilitates the relative rotation movement of the input ring 280 to the output ring 320. The cage skirt 298 is disposed between the head 286 of the input ring 280 and sleeve 324 of the output ring. Each skirt slot 302 is adjacent one of the flats 326 formed in the outer surface of the outer ring sleeve. The components forming the clutch are dimensioned so that the cage 294 can rotate relative to both the input ring 280 and the output ring 320.

A cylindrical pin 305 is disposed in each of the slots 302 formed in clutch cage 294, two pins identified in FIGS. 17 and 25. Pins 305 have a common diameter that is less than the wall thickness of the cage skirt 298. Each pin 305 thus projects inwardly toward from the skirt 298 to the adjacent flat 326 formed in the output ring 320.

A spring 340, one identified in FIG. 17, also part of clutch 270, extends between each pin 306 and adjacent pin 339, one spring identified in each of FIGS. 16 and 17. Springs 340 normally hold the cage so that each slot 302 is adjacent the end of the adjacent flat 326 as seen in FIG. 25. As a result of the cage 294 being in this orientation, each pin 305 is essentially wedged between the inner surface of the input ring head 286 and the adjacent flat 326. When the input ring 280 undergoes counterclockwise rotation in the view depicted in FIG. 25, pins 306 transfer this rotation to both the cage 294 and the output ring 320. When the output ring 320 so rotates, clutch 278 is considered to be in the engaged state.

Figure 27:
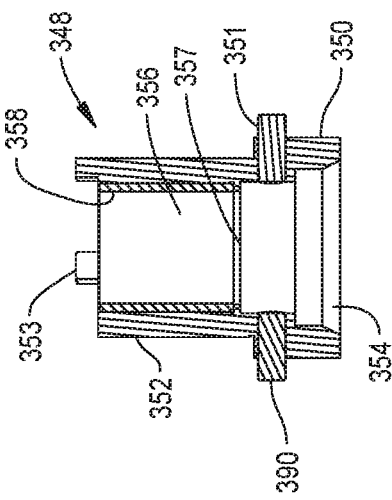
FIG. 27 is a cross sectional view of the tube coupler.
Figure 26:
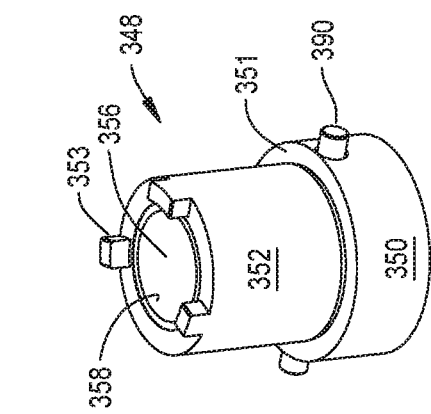
FIG. 26 is a perspective view of the tube coupler.

Clutch 278 drives a tube coupler 348 now described by reference to FIGS. 26 and 27. Tube coupler 348 includes a cylindrical pedestal 350. Pedestal 350 has an outer diameter that is greater than the inner diameter of the sleeve 123 below top plate opening 124. The outer diameter of the pedestal is also such that the pedestal can slip fit within void 332 defined by the inner cylindrical surface of sleeve 324 of the output ring 320. A tube shaped head 352 extends upwardly from pedestal 350. A circular step 351 defines the transition between the coupler pedestal 350 and head 352. A sleeve like low friction bushing 358 is shown disposed around the inner cylindrically shaped wall of head 352. Three equangularly spaced apart teeth 353 extend upwardly from the circularly shaped top face of coupler head 352, one tooth identified.

The tube coupler 348 is formed to have a bore 354 that extends upwardly from the bottom of pedestal 350. Not identified is the tapered counterbore that forms the opening into bore 354. Bore 354 opens into a bore 356. Bore 356 is coaxial with and has a smaller diameter than bore 354. Bushing 358 it is understood is disposed against the inner surface of coupler head 352 that defines bore 356. A small lip 357 protrudes into bore 356. Lip 357 is located near the bottom of the coupler head 352. Lip 357 is the structural feature of the tube coupler that supports bushing 358 in bore 356.

Two axially aligned pins 390 extend radially outwardly from opposed sections of the coupler pedestal 350. Not identified are the bores internal to the pedestal in which the pins are seated. The pins 390 are dimensioned to seat in notches 336 internal to the output ring 320. As a result of the seating of pins 390 in the output ring notches 336, tube coupler is connected to clutch 278 to both rotate in unison with the output ring 320 and move longitudinally relative to the ring 320.

Assembly base 102 is constructed so that the tube coupler 348 is able to both rotate in and move longitudinally in sleeve 123 integral with the shell top plate 122. A spring 394, identified in FIGS. 17 and 18, extends between recessed surface 334 of the output ring 320 and the step internal to the tube coupler between bore 354 and bore 356. Spring 394 biases the tube coupler 348 so teeth 353 are normally urged away from the shell top plate. The abutment of the external step 351 above the coupler pedestal 350 against the overlying end of sleeve 123 limits the upward movement of the tube coupler 348.

The primary coupler 194 extends through bushing 358. Owing to the dimensioning of the components of base 102 and the low friction nature of the bushing 358, primary coupler 194 is able to both rotate relative to and move longitudinally within bushing.

Figure 29:
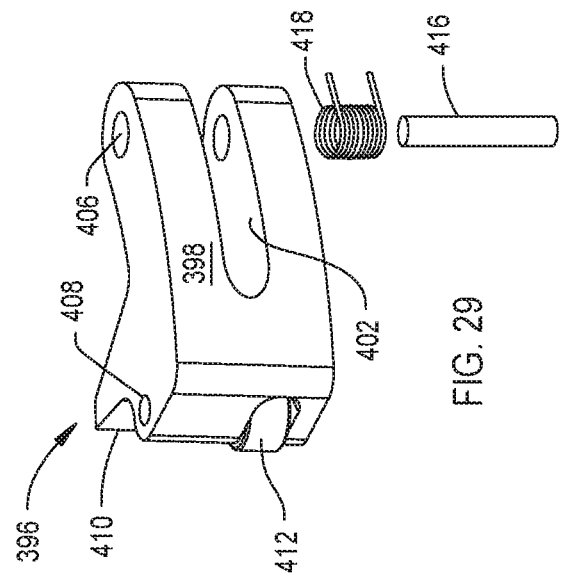
FIG. 29 is an exploded view of the pawl and attached components.
Figure 28:
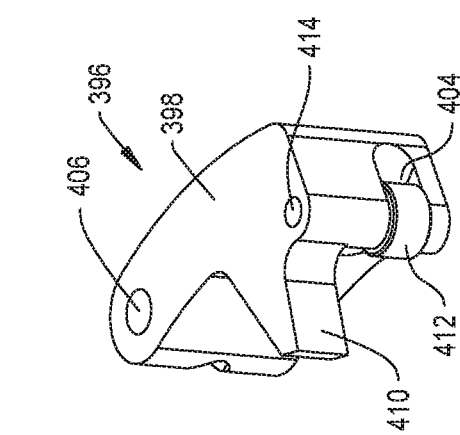
FIG. 28 is a first perspective view of the pawl that engages the clutch.

A pawl 396, seen best in FIGS. 28 and 29, selectively blocks the rotation of the clutch cage 294 to transition clutch 270 between the engaged and disengaged states. The pawl 396 has a body 398 that is formed as to have a longitudinal axis that is curved. The corners of the body 398 are rounded. Pawl body 398 is further formed to have a groove 402 that extends longitudinally along the body. Groove 402 extends inwardly from the outer side of the body 398, the side of the body that is directed away from the tube cam 252. The groove 402 forms an opening in one end of the body 398, opening not identified. As the groove 402 extends from the end of the body in which the groove forms an opening, the depth of the groove decreases. The pawl body 398 is further formed to have a notch 404. Notch 404 is located in the end of the body opposite the end of the body from which groove 402 extends. By reference the gravity reference plane, notch 404 is located below groove 402.

Pawl body 396 is further formed to have two bores that extend top to bottom through the body. A first bore, bore 406, extends through the body adjacent the end of body from which groove 402 extends. Bore 406 intersects groove 402. The second bore, bore 408, is located inward of the end of body opposite the end in which bore 406 is formed. Bore 408 intersects notch 404.

The pawl 396 is further formed so as to have a finger 410. Finger 410 extends outwardly from inner side of the body 398. The pawl 396 is formed so that the finger 410 is located above notch 404.

A roller 412 is disposed in pawl notch 404. The roller 412 is rotatably held to the pawl body by a pin 414 that is seated in bore 408 and extends through the roller.

The pawl 396 is pivotally mounted to a pin 416 that extends upwardly from base 152 of inner plate 150. A spacer 417, seen only in FIG. 5B, holds the pawl above the base 152. In the depicted version of the invention, pin 416 extends through the spacer 417. Spacer 417 is mounted to the inner plate 150 to be static relative to the plate.

A torsion spring 418, seen only in FIG. 29, is seated in groove 402. More particularly, the helically center portion of spring 418 is seated around the section of pin 416 that extends through pawl groove 406. One leg of the torsion spring 418 is disposed against the surface of the pawl body 398 that defines the base of groove. The opposed leg of the torsion spring 418 bears against an adjacent surface of inner plate web 164.

Owing to the presence of spacer 417, pawl 396 is positioned so that the pawl roller 412 is positioned so that the roller 412 is in the same plane as the tube cam 252. Pawl finger 412 is the same plane in which tab 304 integral with clutch 270 rotates. Torsion spring 418 places a force of the pawl that forces roller 412 against the outer surface of tube cam 252. The components forming the assembly base 102 are dimensioned so that when the roller 412 rides against the cam inner lobe 258, finger 410 is disposed in the space through which tab 304 rotates. When the rotation of cam causes the outer lobe 262 to rotate against roller 412, the force of the cam 252 overcomes the force of spring 422. Pawl 396 pivots around pin 416. As a result of this pivotal movement, finger 410 moves away from the space through which tab 304 rotates.

When pawl 398 is spaced from tab 304, springs 340 place a torque on the clutch cage to hold the cage in the position depicted in FIG. 25. Specifically, the pins 305 are held adjacent the flats 326. Owing to where the pins 305 are positioned between the input ring 280 and the output ring 320, the pins become wedged between these two components, the input ring and the output ring. Pins 305 are thus blocked from rotational motion. The pins 305 are also understood to be in frictional contact with the inner cylindrical surface of the head 286 of the input ring 280. When the input ring 280 is rotated counterclockwise when viewed from the perspective of FIG. 25, the rotation of the input ring 280 is, owing to the frictional contact, transferred to the pins 305. Pins 305 thus rotate with the input ring. Owing to the pins 305 being wedged against the output ring 320, the pins force the output ring into a like counterclockwise rotation. When the clutch is in this state, the clutch is on the engaged state.

Figure 30:
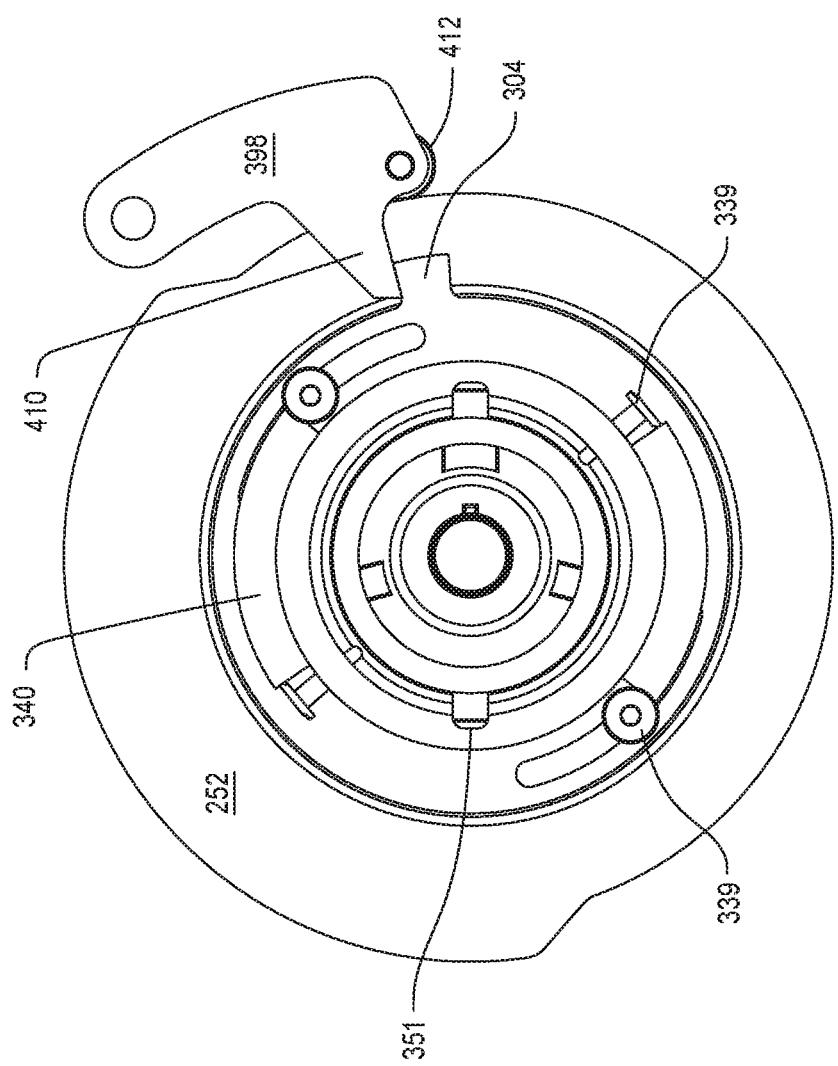
FIG. 30 depicts the engagement of the pawl with the tab integral with the inner coupler of the clutch.
Figure 31:
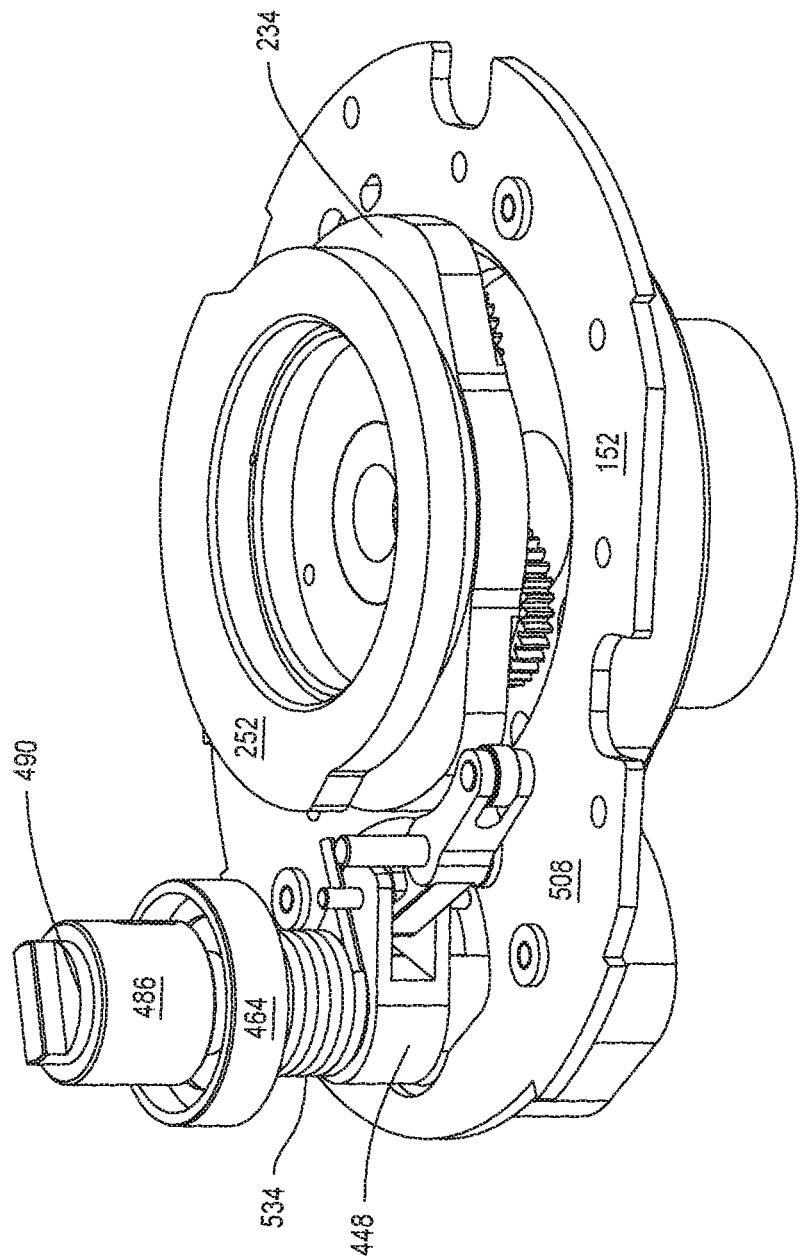
FIG. 31 is a first perspective view of the arm coupler integral with the base and the assembly that pivots the arm coupler.

There are times during the operation of the assembly 100 when the pawl 398, as seen in FIG. 30, presses against the tab 304 integral with the clutch cage 294. As a result of this pawl against tab abutment, the clutch cage is blocked from further rotation. When this even occurs, the rotation of the pins 305 relative to the output ring 320 shifts. Specifically, the cage 294 and pins move to a rotation orientation, relative to the inner output ring 320 that is clockwise to the rotation orientation seen in FIG. 25. As a result the pins are no longer wedged against the output ring. When the pins 305 are in this rotation, the pins do not transfer the rotational movement of the input ring 280 to the output ring 320. The clutch is in the disengaged state.

The assembly base 102 also includes a cage driver 420. Cage driver 420 pivots the cage 764 internal to the cleaning module 602. The cage driver 420 includes a shaft 422 seen best in FIG. 35. Shaft 422 is a single piece component with a number of coaxial sections that have different diameters. At the bottom of shaft 422 there is a foot 424. Foot 424 is formed to have two parallel flats 423 (one seen) that are located inwardly of the outer cylindrical surface of the foot. A trunk 428 is located immediately above the foot 424. Trunk 428 has a diameter that is larger than the diameter of the foot 424. A collar 430, also part of shaft 422, extends circumferentially around and radially outward from a portion of trunk 430. Shaft 422 is formed so that the trunk 428 extends outwardly from the shaft starting at a location slightly above the mid-level of the shaft. The top of the collar 430 is located below the top of the trunk 428. The shaft 422 is further formed to have a head 432 that extends upwardly from the trunk 428.

A closed end bore 436 extends upwardly from the bottom of foot 424. Flats 423 and bore 436 are present to facilitate assembly and disassembly of the base 102 and are otherwise not relevant to this invention, The shaft 422 is further formed to have an elongated oval shaped hollow 438 that extends side-to-side through the shaft. Hollow 438 is centered on a major axis that is perpendicular to the top-to-bottom longitudinal axis through the shaft 422. Shaft 422 is formed so that the hollow 438 extends across the whole height of the collar 430. Hollow 438 also extends a short distance into the portions the shaft trunk 428 that extends below and above the collar 430. The hollow 438 is closed ended; the hollow does not extend laterally through the trunk 428 and collar 430. The shaft is further formed with a circular through bore 440. Bore 440 is formed in the shaft head 432 and located immediately above the trunk 428. The bore 438 is centered on an axis that is perpendicular to and intersects the longitudinal axis through the shaft 422.

Shaft 422 is disposed in the base 102 so foot 424 and torso 428 extend through panel 160 that is part of inner plate 150. The foot and leg 424 extend through concentric openings formed in panel 160. A bushing 444 formed from acetyl or other low friction material extends around the leg 424 and the adjacent opening defining surface of the plate 150. Bushing 444 facilitates the rotation of the shaft 422.

A crank 448 that extends outwardly from the shaft 422 sets the rotational orientation of the shaft 422. The crank 448 includes a circular ring 450. Ring 450 has an inner diameter that allows the crank to tightly fit over the collar 430 integral with the shaft 422. Two parallel, spaced apart overlapping tabs 454 extend radially outwardly from ring 450.

The crank 448 is further formed so ring 450 has two opposed recessed steps 452. Steps 452 are recessed inwardly relative to the opposed top and bottom faces of the ring 450 and surround the through center opening 454 that extends axially through the ring. Crank 448 is further formed to have a slot 456. Slot 456 extends radially outwardly from the cylindrical inner surface of the ring that defines opening 454. Slot 456 is thus contiguous with the center opening 454. The crank 448 is formed so that slot intersects the surfaces of steps 452. Each one of the crank tabs 454 is formed with an opening 458 that extends through the tab. The openings 458 are located slightly inward of the outer ends of the tabs 458. Openings 458 are coaxial.

Crank 448 is seated around shaft 422 so that the crank slot 456 is aligned with hollow 438 internal to the shaft. A key 460 extends from the hollow 438 to slot 456. Key 460 thus holds the crank 448 to the shaft 422 so the two components rotate as a single piece unit.

A hat 464 is disposed over shaft head 432. The hat 464, as seen in FIGS. 36 and 37, has a cylindrical core 468. A brim extends outwardly radially outwardly from and circumferentially around the core 468. The brim has an inner section 469 that is the section of the brim that extends radially outwardly from the core. Inner section 468 of the brim lies in a plane that is perpendicular to the top-to-bottom longitudinal axis through the core. Hat 464 is formed so this inner section of the brim extends outwardly from a location approximately midway along the length the core 468. The brim has an outer section 470 that extends upwardly from the outer perimeter of the inner section. Hat 464 is formed so the inner diameter of the brim outer section 470 is slightly greater than the inner diameter of sleeve 127 integral with the shell top plate 122.

Hat 464 is formed to have a closed end bore 472 that extends upwardly from the bottom of core 468. The core 468 is formed to define two diametrically opposed notches 474. Notches 474 extend upwardly from the bottom of core 468. Each notch 474 opens into bore 472. Bore 472 is dimensioned to allow the shaft 432 to slip fit in the bore. The hat core 468 is formed with a second bore, closed end bore 476. Bore 476 extends downwardly from the top of core 468. The hat is formed so that upwardly directed portion of the brim inner section 469 is formed with a surface 478 that is recessed relative to the outer portion of this section of the rim. This recessed surface 478 is understood to surround the core 468. Above the brim hat 464 is formed to have two diametrically opposed openings 477 that extend onto the core 468. Each opening 477 extends into bore 476.

Hat 464 is disposed over the head 432 of shaft 422 so head 432 is disposed in and able to rotate in hat bore 472. The bottom face of the core 468, which is the bottom of hat 464, seats on the step that is the transition surface between shaft trunk 428 and head 432. A pin 480 is seated in bore 440 internal to the shaft head 432. The opposed ends of pin 480 project radially outwardly from the shaft 422 so as to seat in notches 474 located at the base of hat 464. Owing to the presence of pin 480 in the hat notches 474, the hat 464 is able to engage in a limited degree of rotation around the shaft 422. In some versions of the invention, the components forming the assembly base are constructed so that the hat can rotate between 5° and 45° around the shaft.

A pin 479, seen only in FIG. 34, extends downwardly from the brim inner section 469. Pin 479 is spaced radially outwardly from the core 468 of hat 464. Not shown is the bore in the hat 464 in which the top of the pin 479 is press fit.

An arm coupler 486, also part of the cage driver 420, is disposed over hat 464. The arm coupler 486, seen best in FIGS. 38 and 39, includes a cylindrical base 488. Arm coupler base 488 has an outer diameter that allows the base to seat in the space immediately above the recessed surface 478 of hat 464. A circular boss 490, also part of the arm coupler 486, rises above the top of base 488. Arm coupler 486 is formed so that the boss 490 has an outer diameter less than the outer diameter of the base 488. A bar 492, integral with the boss 490, rises above the top surface of the boss. Bar 492 has opposed side surfaces that are parallel. The bar extends laterally across the boss to intersect the top to bottom common longitudinal axis of the base 488 and the boss 490.

The arm coupler 486 is further formed to have a closed end bore 494 that extends upwardly from the bottom face of the base 488. The arm coupler 486 is formed so that bore 494 has a diameter that allows the slip fitting of the hat core 468 in the bore. Arm coupler 486 is also formed to have two diametrically opposed openings 496 that extend inwardly from the outer surface of the base 488. Openings 496 are oval shaped and are formed in the arm coupler 486 to have major axes that are parallel to the longitudinal axis through the coupler. The openings 496 each open into bore 494.

When the cage driver 420 is assembled, the arm coupler 486 is seated over hat core 468. A pin 502 is seated in at least one of the bores 477 integral with the hat 464 so as to extend outwardly from the core 468 of the hat. The pin 502 extends into a one of the openings 496 internal to the arm coupler 486. This pin-in-opening arrangement holds the coupler 486 to that hat 464 so the coupler both will rotate in unison with the hat and is able to move longitudinally relative to the hat. A spring 504 is seated in hat bore 476 and extends upwardly above the hat 464. The spring 504 extends into the coupler bore 494 and presses against the interior surface of the coupler 486 that defines the closed end of bore 494. Spring 504 thus places a force on the arm coupler 486 that, in the absence of an opposing force, holds the arm coupler in its disposition relative to hat 464.

A rocker arm 508, pivots the crank 448 to cause the like pivotal motion of the cage driver 420. The rocker arm 508, as best seen in FIG. 41, is generally in the shape of an elongated beam. In the illustrated version of the invention, the arm has a first section 510 that is generally solid. A slot 512 is formed in beam first section 510 to extend inwardly from the outer end of the rocker arm 508. The opposed end of the arm first section 510 is slightly larger in cross sectional width than the rest of the section. Rocker arm has a second section 514 that extends outwardly from the first section 510. More particularly, the arm second section 514 extends outwardly from the end of the first section 510 opposite the end in which slot 512 is formed. Rocker arm 508 is formed so the major axis through the arm second section 514 is angled relative to the major axis through the arm first section 510. In the illustrated version of the invention, rocker arm 508 is also shaped so the bottom face of the arm second section 514 is above the adjacent bottom face of the arm first section 510. The top face of the arm second section 514 below the adjacent top face of the arm first section 510.

Two bores 516 and 518 extend top to bottom through the arm first section 510. Bore 516 is located immediately inward of the free end of the arm first section 510, the end of section 510 spaced from the second section 514. Bore 516 intersects slot 512. Bore 518 extends through the end of the arm first section 510 that is adjacent the arm second section 514. The rocker arm 508 is further formed so that an elongated slot 520 extends top to bottom through the arm second section 514.

A roller 524 is mounted in slot 512 internal to the rocker arm 508. A pin 522 the ends of which are seated in the sections of bore 516 on either side of the slot 512 rotatably holds the roller 524 to the rocker arm 508. The components forming the assembly base 102 are arranged so that the outer surface of the roller 524 projects beyond the perimeter of the rocker arm 508.

A pin 526, identified in FIG. 34, pivotally holds the rocker arm 508 to the inner plate 150 immediately above the top surface of base 152 of the plate. The pin 526 is seated in one of the openings formed in the inner plate 150. When the rocker arm 508 is mounted to the inner plate 150, roller 524 is able to press against the outer faces of lobes 238 and 242 of the arm cam 234.

When the rocker arm 508 is mounted to the inner plate 150, the arm second section 514 is located between the tabs 454 integral with crank 448. A pin 530 that extends through crank tabs 454 and arm slot 520 couples the crank 448 to the rocker arm 508. In the depicted version of the invention, a block 528 is slidably disposed in the arm slot 520. Pin 530 extends through a hole 529 formed in the block 528. Cage driver 420 is further constructed so that pin 530 projects both above the top located crank tab 454 and the bottom located crank tab 454.

Figure 33:
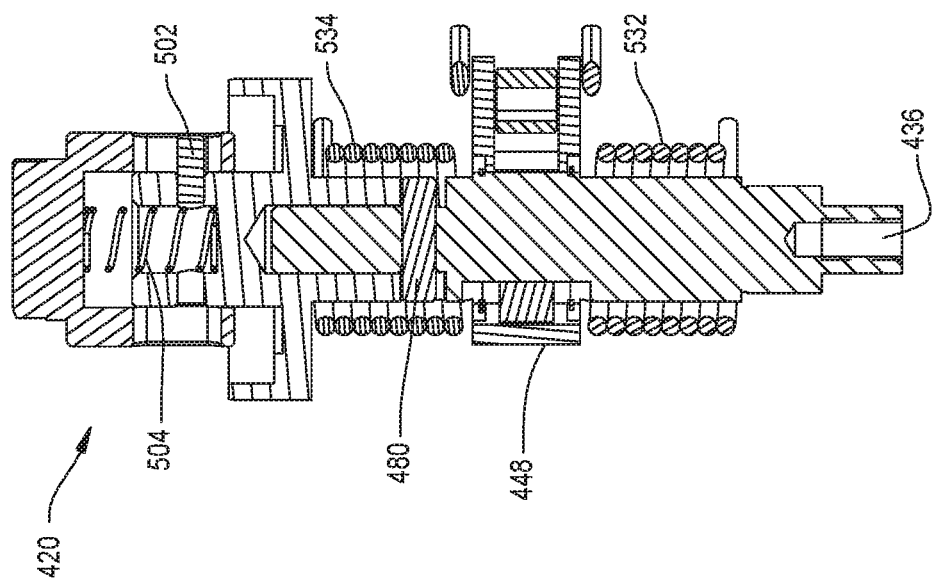
FIG. 33 a cross sectional view of the arm coupler integral with the base and the assembly that pivots the arm coupler.
Figure 32:
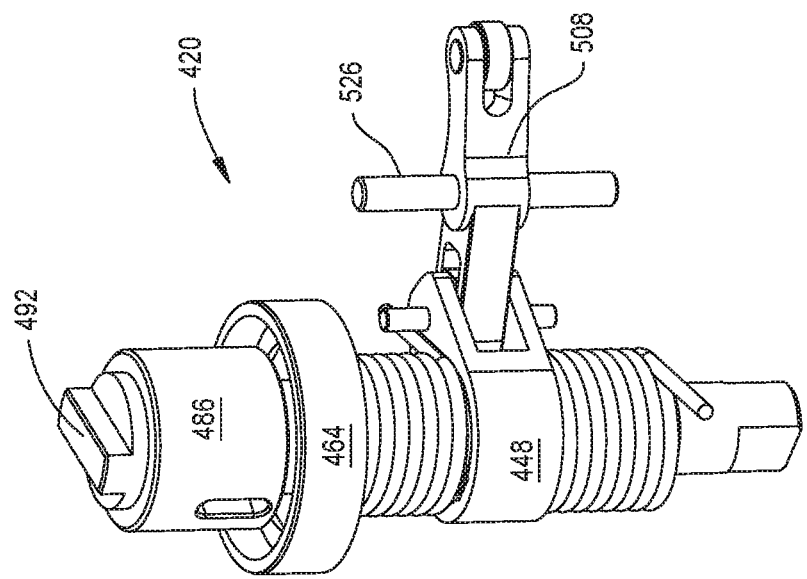
FIG. 32 is a is a second perspective view of the arm coupler integral with the base and the assembly that pivots the arm coupler.

From FIGS. 33 and 34 it can be seen that the cage driver 420 includes two torsion springs 532 and 534 that are disposed around shaft 422. Torsion spring 532 is disposed around the section of the shaft trunk 428 below collar 430. Spring 532 is thus seated in void 156 formed in plate 150. One leg of the torsion spring 532 is pressed against the section of the pin 530 that extends below the crank 448. The opposed leg of spring 532 presses against a portion of the web 158 that defines void 156 internal to inner plate 150.

The second spring, spring 534, is actually disposed around the section of the hat core 468 located below the brim 469. One end of spring 534 is disposed against the section of pin 530 that extends above the crank 448. The opposed leg of spring 534 presses against the pin 479 that extends from hat 464. Spring 534 thus normally holds the hat 464 in a fixed rotational orientation over shaft 422. The extent to which the hat 464 is able to rotate is limited by the extent to which the hat notches 474 can rotate over the pin 480 held fast to shaft 422.

During operation of the bone cleaner and bone mill of this invention, springs 532 and 534 can, individually or collectively, cause the rocker arm 508 to place an appreciable side loading force against arm cam 234. Balance collar 246 resists this force. The balance plate thus holds the arm cam 234 and by extension the tube cam 252 in axially stable position within the assembly base.

Figure 42:
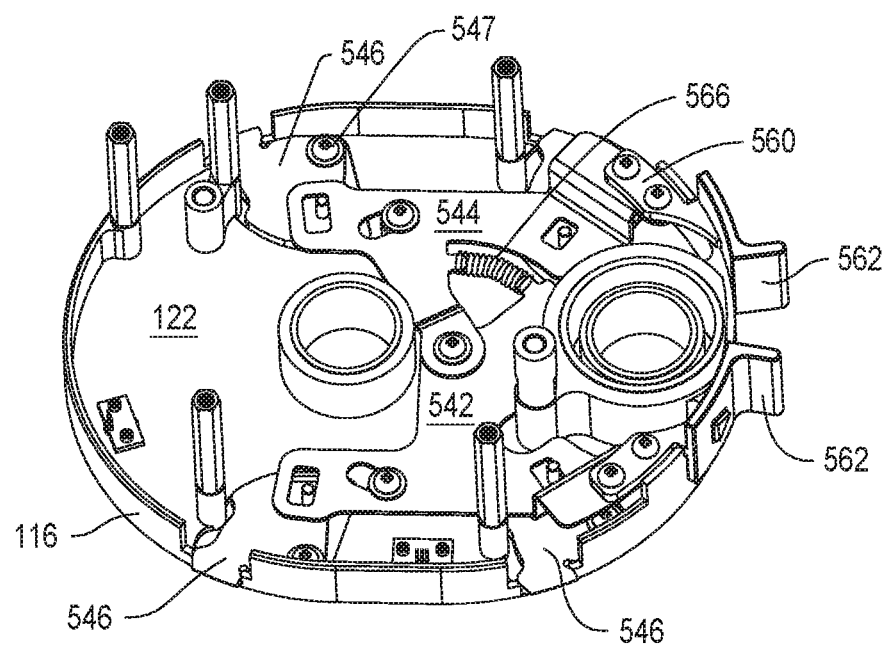
FIG. 42 is a perspective view of the latch assembly attached to the underside of the shell.
Figure 43:
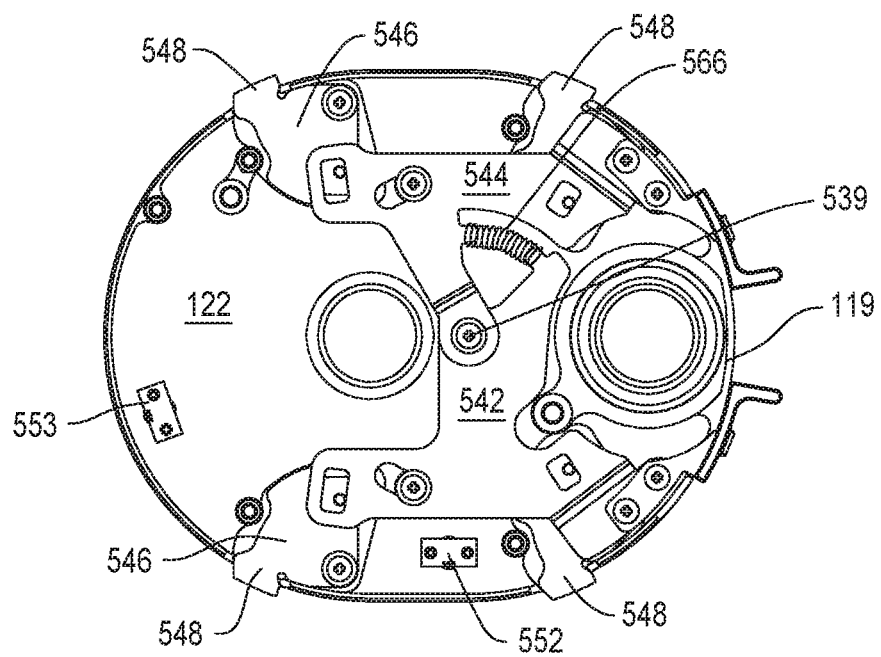
FIG. 43 is a plan view of the latch assembly.

A latch assembly 540, seen in FIGS. 5A, 42 and 43, is mounted to the underside of the top plate 122 of the assembly base 102. The latch assembly 540 releasably holds first the cleaning module 602 and then the milling module 902 to the base 102. Latch assembly 540 includes two primary plates 542 and 544. Primary plates 542 and 544 are mounted to the underside of the top plate 122 to pivot around a common axis. In the Figures the primary plates 542 and 544 are both seen being pivotally held to the undersurface of the top plate 122 by a common fastener 539. Fastener 539 defines the axis around which the primary plates 542 and 544 pivot. Four secondary plates 546 are also pivotally mounted to the underside of the top plate, three secondary plates identified in FIG. 42. In FIG. 42 a single one of the fasteners 547 that holds one of the secondary plates to the underside of the top plate 122 and around the secondary plate pivots is identified. Each secondary plate 546 is formed with a tab 548. The secondary plates 546 are mounted to the top plate 122 so that each tab 548 extends out of a separate one of the openings 118 in the top plate 122. Two of the secondary plates 546 are coupled to primary plate 542 to move upon the pivoting movement of plate 542. Two of the secondary plates 546 are coupled to the primary plate 544 to move upon the pivoting movement of plate 544. In FIG. 5A, a single one of the pins 545 that connects one of the secondary plates 546 to primary plate 542 for pivotal movement is identified.

Latch assembly 540 also includes two finger grips 562. The finger grips 562 are located adjacent the curved outer side of the top plate 122 closest to opening 126. A bracket 560 extends inwardly from each finger grip 560. The brackets 560 extend through slot 119 formed in the rim 116 so as to extend into the space immediately below the top plate. Each bracket 560 connects the finger grip from which the bracket extends to a separate one of the primary plates 542 or 544. One of the fasteners 563 that holds the brackets 560 to each of the primary plates 542 and 544 is seen in FIG. 5A. Not identified are the openings in the primary plates 542 and 544 and bracket 560 through which the fasteners 563 extend.

A spring 566 extends between the latch assembly primary plates 542 and 544. Spring 566 is in compression to hold the primary plates in the position in which the plate 542 and 544 are arcuately spaced from each other. When the primary plates 542 and 544 are so spaced, the secondary plates 546 are positioned so that tab 548 extend out of the openings 118 integral with the shell op plate 122. The force spring 566 places on the primary plates 542 and 544 can be overcome by the manual pressing of the finger grips 562 towards each other. This displacement of the finger grips 562 results in the like displacement of the primary plates 542 and 544 so the plates 542 and 544 pivot inwardly towards each other. The inward movement of the primary plates 542 and 544 results in the pivoting movement of plates 546 that retract tabs 546 inwardly away from the shell openings 118.

Two circuit boards 552 and 553 are also shown mounted to the underside of top plate 122. Circuit board 552 is mounted to the top plate 122 so as to be adjacent the side edge of the plate closest to the shell face panel 108. Circuit board 553 is mounted to the curved end of the plate closes to plate opening 124 to the top plate 122 so as to be adjacent the side edge of the plate closest to the shell face panel 108.

Figure 44:
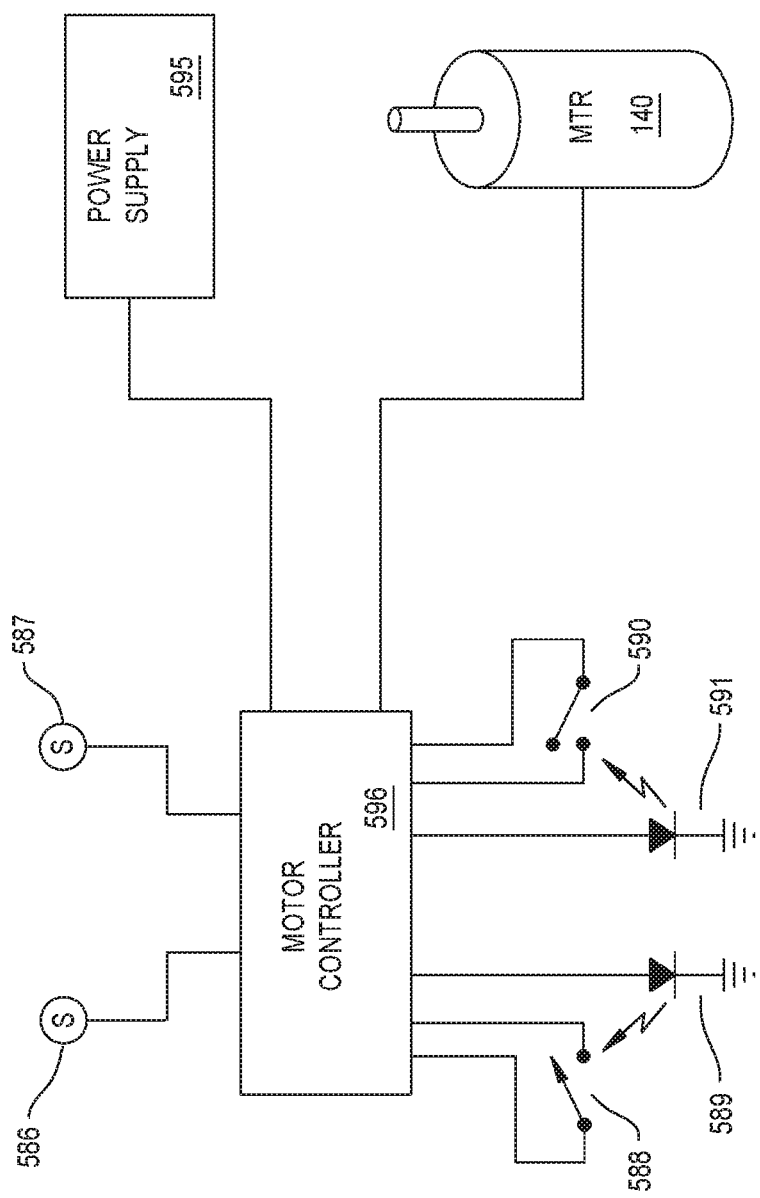
FIG. 44 is a block diagram of the components that actuate the assembly of this invention.
Figure 45:
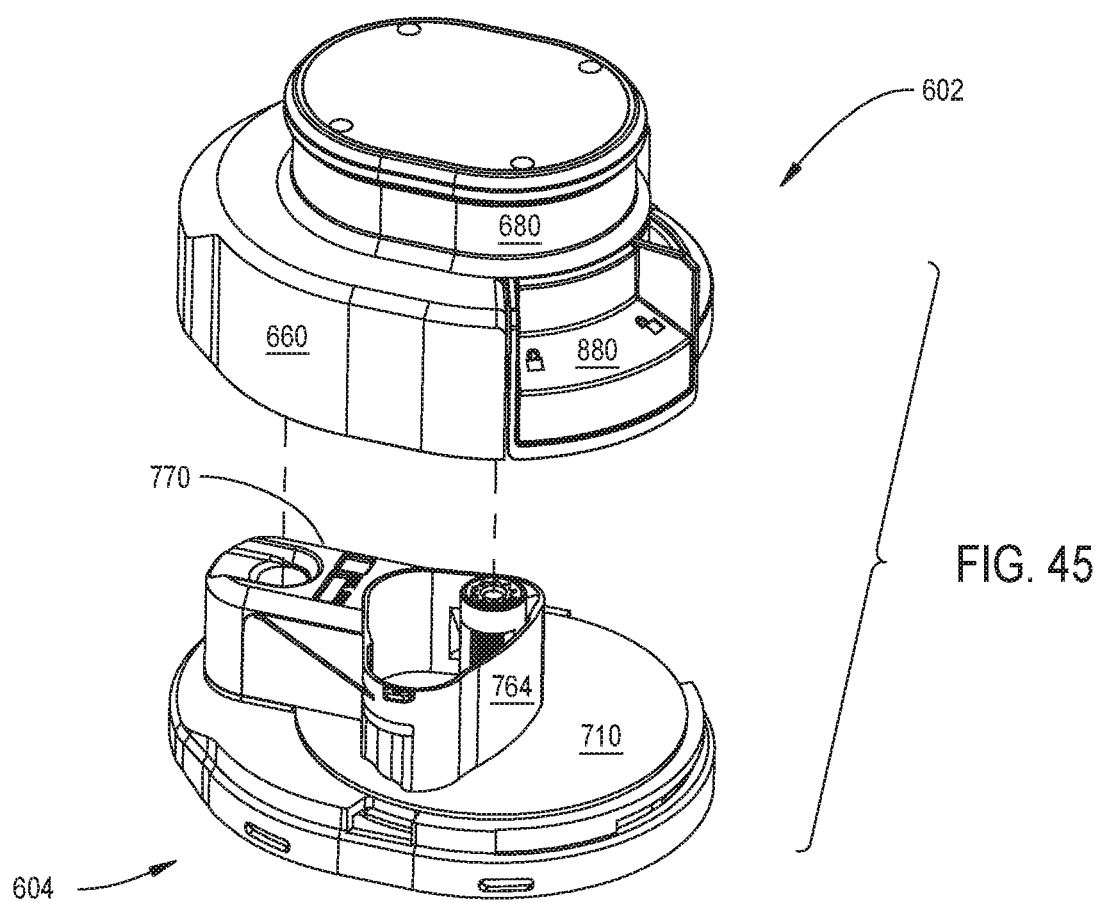
FIG. 45 is a perspective view of the cleaning module depicting how the shell is removably attached to the module base.

Sensors 586 and 587, shown as block components in FIG. 44, are mounted to the circuit boards 552 and 553, respectively. Sensors 586 and 587 each generate signals based on the absence/presence of a local magnetic field. In some versions of the invention, sensors 586 and 587 are Hall effect sensors. It should be understood that top plate 122 is formed from material that allows the transmission of localized magnetic fields therethrough. Specifically, the top plate 122 is formed from material that does not attenuate the passage of localized magnetic fields to the extent that the sensors 556 and 557 are not able to sense the absence/presence of the fields.

From FIG. 44 it is further appreciated that sensors 586 and 587 are part of the sub-assembly that regulates the actuation of assembly 100 of this invention. This sub-assembly also includes a motor controller 596 also disposed in the assembly base. Motor controller 596 regulates the application of energization signals sourced from a power supply 595 to the motor 140. The signals output by the sensors 586 and 587 representative of the absence/presence of the localized magnetic fields are output to the motor controller 596.

Also part of the sub-assembly that regulates the operation of motor 140 are two momentary contact switches 588 and 590. In FIG. 2, switches 588 and 590 are called out as the control buttons disposed on the face panel 108 of base shell 104. Switches 588 and 590 are shown connected to the motor controller 596.

The control sub-assembly is also shown as having two LEDs. LEDs 589, and 591. LED 589 is shown as emitting light adjacent switch 588. LED 591 is shown emitting light adjacent switch 590. In some versions of the invention each switch 588 and 590 is surrounded by a transparent ring, transparent rings not identified. The light emitted by each LED 589 and 591 is visible through the transparent ring adjacent the switch 588 or 590 with which the LED is associated.

In some versions of the invention one or both of the power supply 595 and controller 596 are not disposed in the shell 104 of the base 102. For example in one version of the invention, the power supply 595 and motor controller 596 are components of a control console to which the base 102 is removably attached. One such control console is sold by the Applicant as the CORE Console. Features of this console are disclosed in U.S. Pat. No. 7,422,582/PCT Pub. No. WO 2006/039331, the contents of which are explicitly incorporated by reference. Not shown is the cable that is used to connect the components internal to the control console to the components internal to the assembly base 102.

III. Cleaning Module

The cleaning module 602 of assembly 100 of this invention, as seen 45-48, includes a base 604 to which a shell 660 is removably attached. Base 604 and shell 660 collectively form substantial portions of the housing of the cleaning module 602. A fluted screw 690 is rotatably mounted to the base 604 and disposed in the shell 660. A shaving tube 724 surrounds the fluted screw 690. In the illustrated version of the invention, the shaving tube 724 is mounted to a plate 710 that rests on the upwardly directed surface of the base 604. Plate 710 and shaving tube 724 are fitted to the cleaning module to be able to rotate over the base 604. Within the module housing, a cage 764 surrounds the fluted screw and shaving tube 724. Cage 764 is located at the free end of an arm 750. Arm 750 has features that facilitate the coupling of the arm to the arm coupler 436 of assembly base 102.

A cap 680 is disposed over shell 660. The cap 680 is part of the housing of the cleaning module 602. Cap 680 defines a catch space 682 above the shell 660. Catch space 682 is the space internal to the module housing that receives the soft tissue cleaned from the bone stock. A hub 850 is disposed in the catch space 682. Hub 850 steadies the fluted screw 680 and the shaving tube 724.

Figure 49:
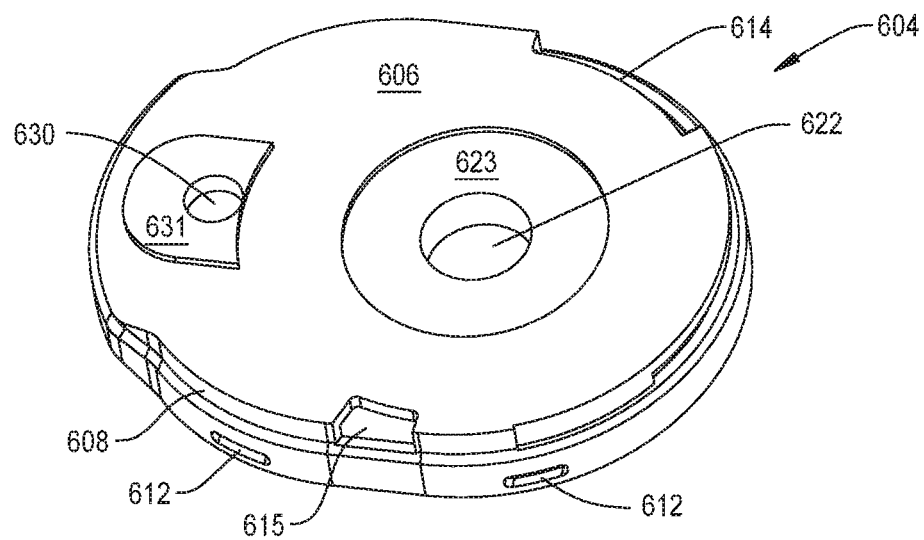
FIG. 49 is a perspective view of the top of the bottom plate of the cleaning module.
Figure 50:
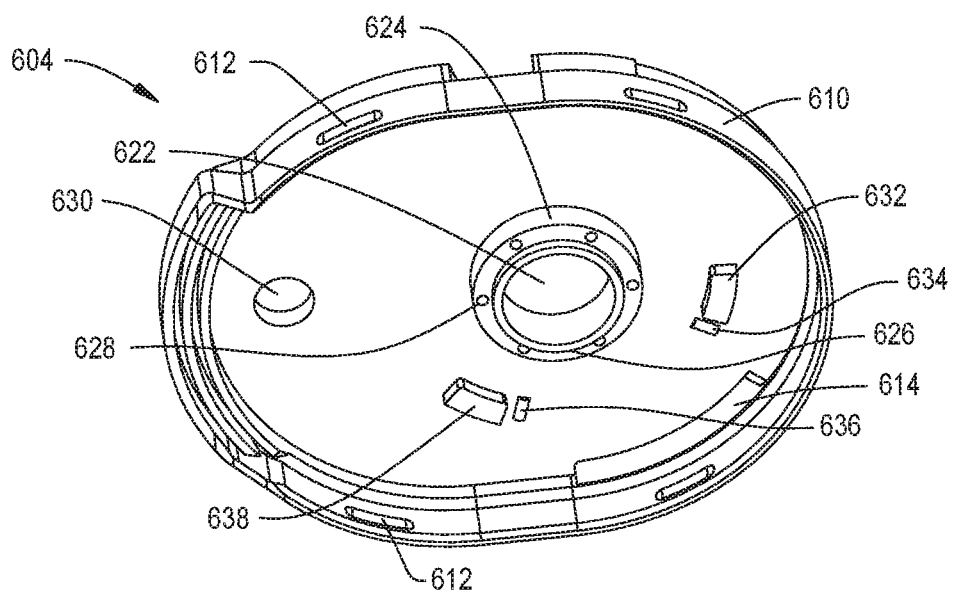
FIG. 50 is a perspective view of the underside of the bottom plate of the cleaning module.

The cleaning module base 604, as seen in FIGS. 49 and 50, is a single piece component. The base 604 includes a planar plate 606. Plate 606 has a shape that approximates the shape of the assembly base top plate 122. An inner rim 608 extends downwardly from the outer perimeter of base plate 606. An outer rim 610 extends downwardly and outwardly around the inner rim 608. Base 604 is formed so that when cleaning module 602 is seated on the assembly base 102, outer rim 610 integral with module 602 seats against rim 116 integral with the assembly base 102.

Cleaning module base 604 is further formed so four slots 612 extend through the base outer rim 610, two slots identified. Slots 612 are positioned and shaped so that when the cleaning module 602 is seated on the assembly base 102, each tab 546 integral with the assembly base latch assembly 540 is in registration with and can seat in a separate one of the slots. The base 604 is further formed so a slot 614 extends through the inner rim 608. The slot 614 extends through a portion of one of the curved end sections of the rim 608. Slot 614 extends a short distance into plate 606. Base 604 is also formed with a notch 615 that forms a void in plate 606. Notch 615 extends inwardly from a portion of the plate 606 opposite slot 614.

Module base 604 is further formed to have two openings 622 and 630. Opening 622 is positioned so that when the module 602 is seated on the assembly base 102, the opening is disposed over the primary coupler 194 and the tube coupler 348. The base 604 is further formed so on the top surface of plate 606 a circularly shaped recessed surface 623 is centered around and extends circumferentially around opening 622. The module base 604 is formed to have an outer ring 624 that extends downwardly from the underside of plate 606 around opening 622. An inner ring 626 extends downwardly from the downwardly directed face of the outer ring 624. Outer ring 624 and inner ring 626 have the same diameter, the diameter of opening 622. Inner ring 626 has an outer diameter less than the outer diameter of the outer ring 624. The module base 604 is further formed so that when the module 602 is seated on the assembly base 102, the exposed circular face of the inner ring is disposed against the surface of top plate 122 around opening 124. Base 604 is further formed to have a number of bores 628, one bore identified, that extend inwardly from the circular face of the outer ring 624 that is located immediately radially outwardly of the outer ring 622.

The opening 630 formed in plate 606 so that when the module 602 is seated on the assembly base, the opening 630 is in registration with the opening 126 formed in top plate 122. Base 604 is further formed so as to have an island 631 that extends a short distance above the top surface of plate 606. The base 604 is shaped so that island 631 surrounds opening 630.

The module base 604 is further formed so that two lock stops 632 and 638 project downwardly from the undersurface of plate 606. Stops 632 and 638 are located a common radial distance away from the center of opening 622. Stops 632 and 638 are arcuately spaced apart from each other by approximately 90°. A small rib protrudes downwardly from the undersurface of the plate 606 adjacent each stop 632 and 636. Rib 634 is located adjacent stop 632. Rib 636 is located adjacent stop 638. The ribs 634 and 638 lie on the same circle around opening 622 around which the stops 632 and 636 are located. Ribs 634 and 636 do not extend downwardly from the undersurface of the plate 606 to the same extent stops 632 and 638 extend downwardly. Base 604 is further formed so that in planes perpendicular to the longitudinal axes along the ribs 634 and 636, the ribs have a convex shape.

Figure 47:
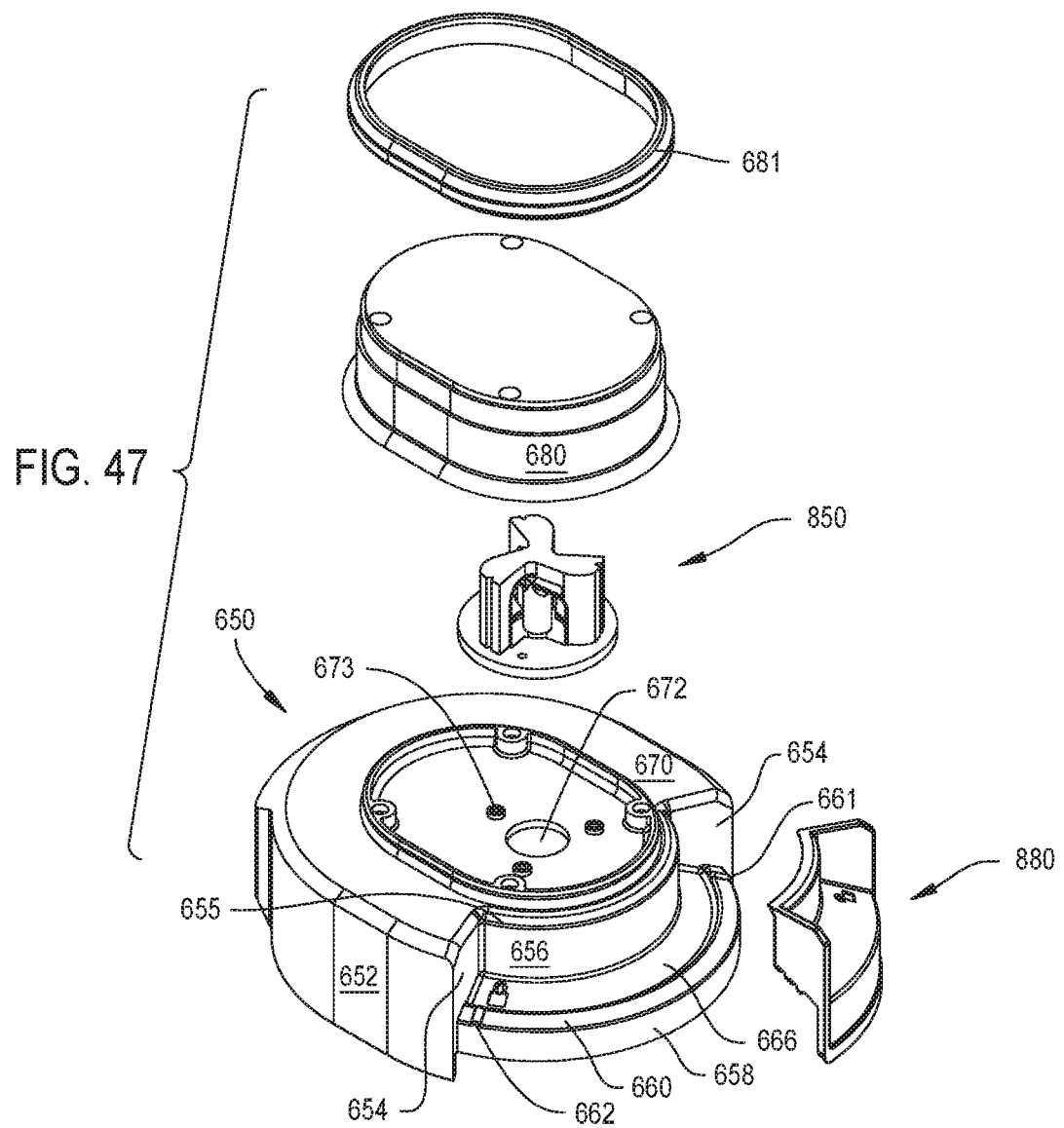
FIG. 47 is an exploded view of the components internal to the top of the cleaning module
Figure 48:
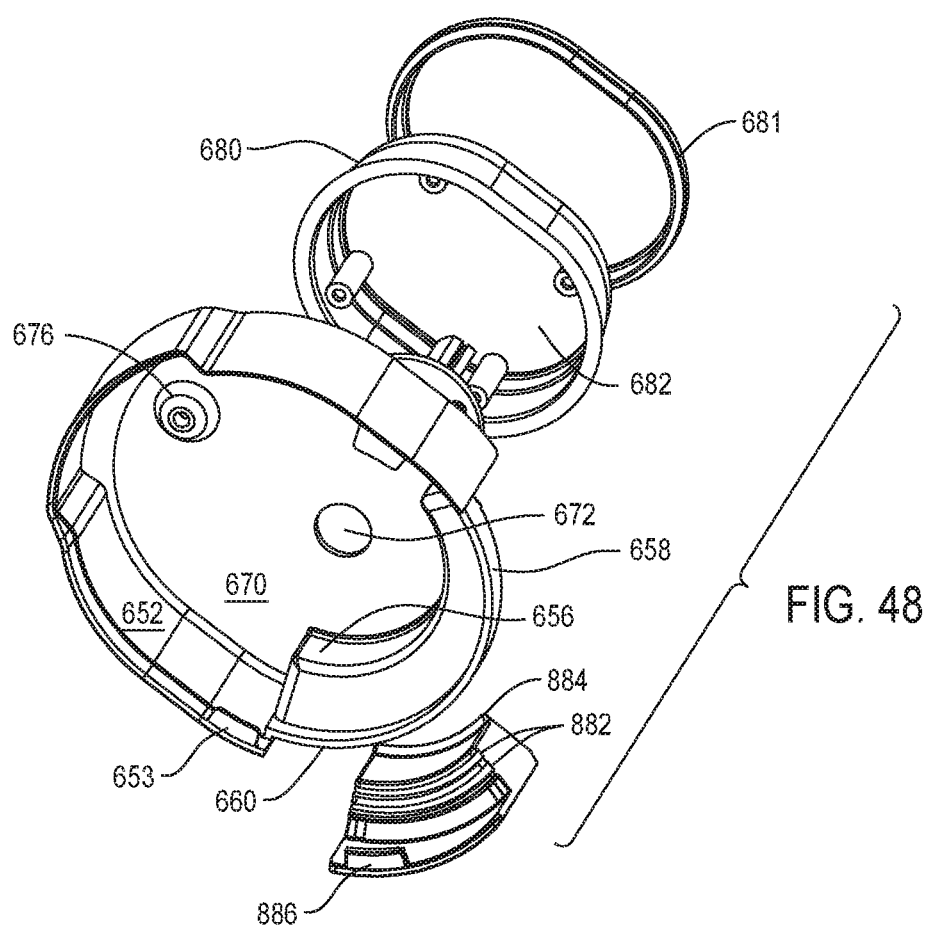
FIG. 48 is an exploded view of the cleaning module and shell and the components located above the shell.

The module shell 650, seen best in FIGS. 47 and 48, is formed to have an outer wall 652. Outer wall 652 is shaped to sit on the outer step between the inner and outer rims 608 and 610, respectively of base 604. The outer wall 652 is further shaped to extend around the base so as to extend around approximately 70% of the circumference of the base. More particularly, outer wall 652 does not subtend the curved end of the base closest to opening 622. Where the outer wall 652 does not subtend the step surface of the module base 604, shell 650 is shaped to have an inner wall 656. The shell 650 is shaped so the inner wall 656 is located radially inwardly from the outer wall 652. Shell 650 is further formed so adjacent the top of inner wall 656 there is an inwardly extending groove 655. Groove 655 extends along to the right to left length of wall 656. End panels 654 extend inwardly from the opposed ends of the outer wall 652 to the adjacent ends of the outer wall 656. The shell 650 is further formed so that the inner wall 656 does not extend the full length of the outer wall 652. While the tops of the walls 652 and 656 are generally in the same plane, the inner wall 656 only extends approximately one-third the distance downwardly that the inner wall 652 extends downwardly.

Shell 650 also has two tabs 653, one tab identified in FIG. 48. Tabs 653 extend inwardly from the bottom of the outer wall 652. The tabs 653 are located adjacent the opposed ends of the wall 652. When shell 650 is seated on base 604, one tab 653 is located below slot 614. The opposed tab 653 is located below notch 615.

Three webs 658, 660 and 666 extend between the opposed ends of the outer wall 652. Web 658 is generally vertically aligned and is located outwardly of the inner wall 656. The web 658 curves from one of the end panels 654 to the opposed end panel 654. The bottom edge of web 658 is located above the bottom edge of the outer wall 652. The top edge of web 658 is located below the top edge of the inner wall 656.

Web 660 extends upwardly and inwardly from the top of web 658. Web 666 extends inwardly and upwardly from web 660. The shell 650 is formed so the outer perimeter of web 666, the portion of web 666 closest to web 660 is stepped below the inner perimeter of web 660. Web 666 extend to the bottom of the inner wall 656. Webs 658, 660 and 666 are arcuate and subtend the gap between the ends of the outer wall 652. Shell 650 is further formed so that two ribs 661 and 662 protrude upwardly and extend the width of web 660. Rib 661 is located a short distance away from a first one of the shell end panel 654. Rib 662 is located a short distance with from the opposed shell end panel 654. Ribs 661 and 662 each extend from the outer perimeter of web 660 to the inner perimeter of the web 660.

The cleaning module shell 650 includes a lid 670. The lid 670 is located above the shell outer wall 652 and inner wall 654. An opening 672 is formed in the lid 670. A boss 676 extends downwardly from the undersurface of lid 670. The shell 650 is formed so that when the shell is disposed on the module base 604, the shell opening 672 is centered over base opening 622 and boss 676 is centered over base opening 630. Three bosses 673, one boss identified extend upwardly from the top surface of lid 679. Bosses 673 are centered around the center of shell opening 672 and are spaced radially away from the outer perimeter of the opening. Bosses 673 are equangularly spaced apart from each other.

Cap 680 also forms part of the housing of the cleaning module 602. The cap 680 is disposed over the lid 670. The means by which the cap 680 is secured to the lid 670 is not part of the invention. The lid 670 thus forms the base of the catch space 682 defined by the cap 680. Opening 672 in the lid 670 opens into the catch space 682.

A ring 681 formed of elastomeric material extends around the top of cap 680. The ring 682 is provided to facilitate the grasping of the integrated shell 650 and cap 680 unit.

Figure 51:
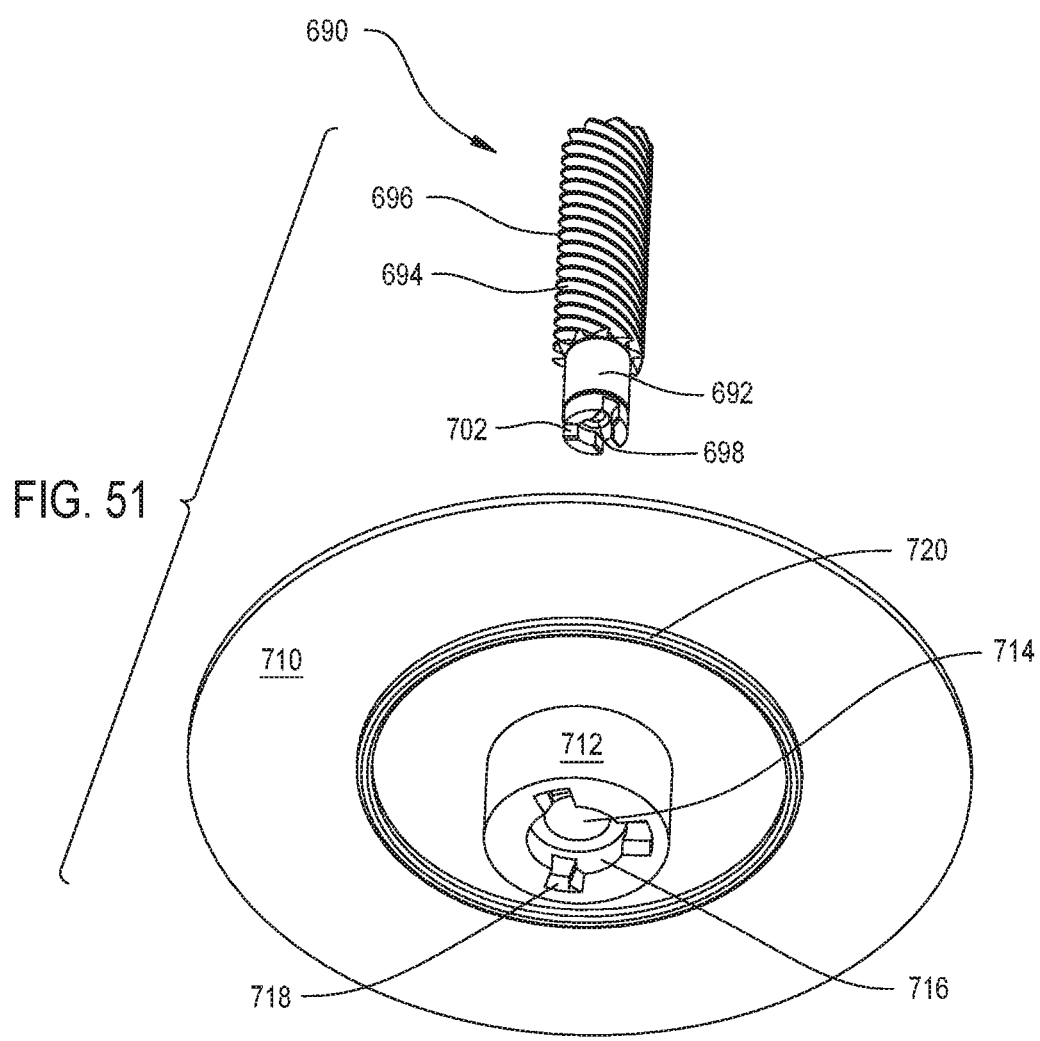
FIG. 51 is an exploded view of how the fluted screw extends through the disk internal to the cleaning module shell.
Figure 52:
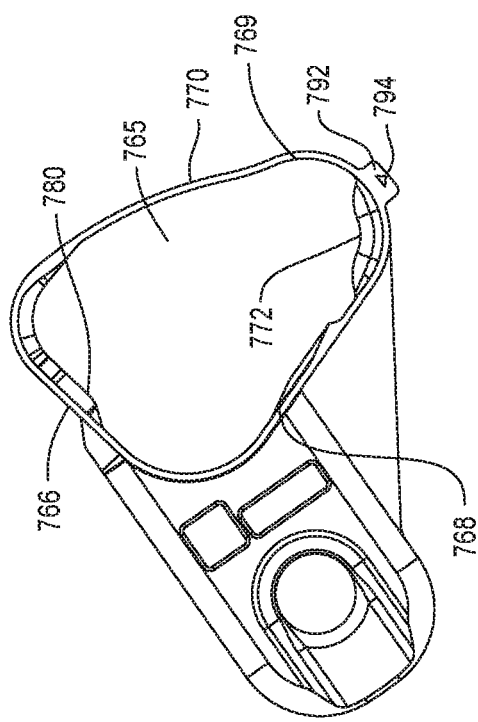
FIG. 52 is a top plan view of the arm internal to the cleaning module shell.
Figure 53:
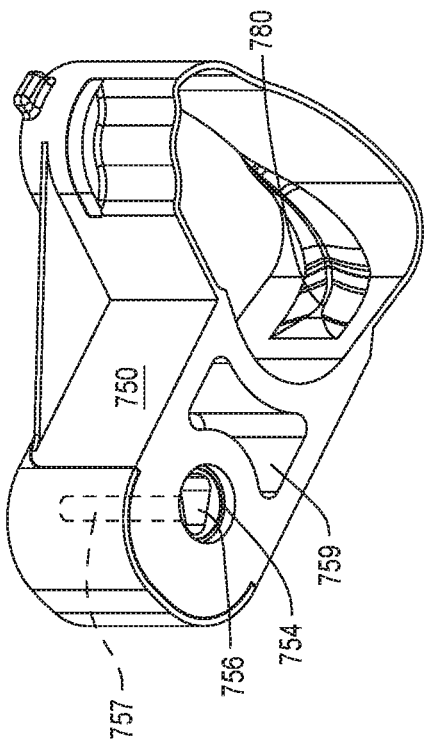
FIG. 53 is a perspective view of the underside of the arm.

The fluted screw 690, seen in FIG. 51, is rotatably mounted to base plate 606. The screw 690 includes a cylindrical stem 692. At a location starting approximately one-fifth the way up from the bottom of the stem, flutes 694, one flute identified, extend helically around the stem 692. The flutes 694 extend to the top of the stem 692. Each flute 694 is formed to define a cutting edge 696, one cutting edge identified. Extending upwardly from the base of stem 692, screw 690 is formed to have closed end bore 698 seen in FIG. 51. Bore 698 is dimensioned to receive pin 198 integral with the primary coupler 194. Fluted screw 690 is further formed to have three equangularly spaced apart notches 702 that extend upwardly from the base of the stem 692, one notch identified. Each notch 702 extends from the outer perimeter of the stem 692 to the bore 698. The notches 702 do not extend as far up the stem 692 as bore 698. The notches 702 have a common width. Each notch 702 is sufficiently wide so a tooth 202 integral with the primary coupler 194 can seat in the notch. The fluted screw 690 is further formed so a closed end bore 704, seen in FIG. 46, extends downwardly from the top of stem 692. Bores 698 and 704 are coaxial with the longitudinal axis through stem 692.

Figure 46:
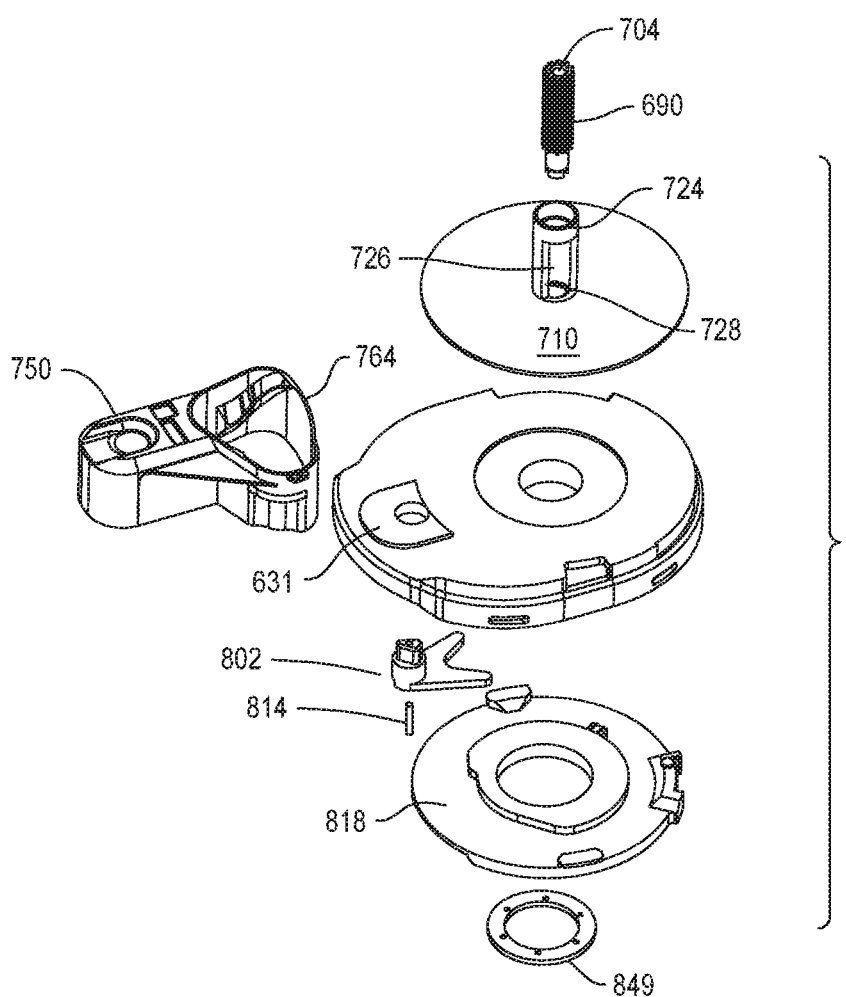
FIG. 46 is an exploded view of components internal to the cleaning module.

Rotating plate 710, sometimes identified as the tumble plate 710, seen in FIGS. 46 and 51, is seated on the module plate 606. The top surface of the tumble plate 710 is essentially planar in shape. A boss 712 extends downwardly from the undersurface of the tumble plate 710. Boss 712 has a diameter that allows the boss to seat and rotate in opening 622 formed in the module base 604. A bore 714 extends upwardly from the bottom of boss 712 through the boss and to the top surface of the plate 710. At the bottom end of the boss 712 a counterbore 716 extends radially outwardly around bore 714. Counterbore 716 has a diameter that is approximately 2 mm less than the diameter of the tube coupler 348. Plate 710 is further formed to have three equangularly spaced apart notches 718. Notches 718 extend radially outwardly from the outer perimeter of counterbore 716. Each notch 718 is able to receive a separate one of teeth 353 integral with the tube coupler 348.

A ring 720 also protrudes downwardly from the undersurface of plate 710. Ring 720 is coaxial with and spaced radially outwardly from boss 712. The outer diameter of ring 720 is marginally less than the diameter of the outer perimeter of the recessed surface 623 that surrounds opening 622 internal to module base 604. When cleaning module 602 is assembled, the plate 710 seats on plate 606 so boss 712 is able to rotate in opening 622. The ring 720 is located immediately inside of the step that defines the transition from recessed surface 623 and the surrounding portion of the plate 604. Ring 720 thus minimizes lateral wobble of the tumble plate 710 in the cleaning module 602.

Shaving tube 724, seen best in FIG. 46, extends upwardly from the bore 714 internal to plate 710. The tube 724 is further shaped to have a window 728. Window 728 extends into the lumen that extends axially through the tube and are diametrically opposed to each other around the longitudinal axis through the tube 724. Window 728 is defined by two arcuately spaced apart and longitudinally extending cutting edges 726 formed in the tube 724, one cutting edge identified. Each cutting edge 726 is the edge defined by the intersection of the inner wall of the tube and a side surface that extends inwardly from the outer wall of the tube to define a side perimeter of the associated window 728.

Collectively the components forming the cleaning module 602 are shaped so that there is a clearance between the edges 696 of the screw flutes 694 and the cutting edges 726 formed in tube 724 of between 0.03 and 0.5 mm.

The shaving tube 724 is press fit mounted in bore 714 internal to tumble plate 710. Shaving tube 724 is mounted to the plate 710 so that bottom end of window 728 is essentially flush with the top surface of the plate.

Arm 750 and cage 764, best seen in FIGS. 52-55, are formed as a single piece unit. Arm 750 is in the form of an elongated bar. One end of the arm 750 is rounded. Molded into the top of arm 750 are cavities 752. The cavities 752 are used as standard guides to provide visual representations of the maximum dimensions of the bone stock that can be cleaned by the module 602.

The arm 750 is formed so that inward of the rounded end of the arm, there are first and second bores 754 and 756 which are accessible from the bottom of the arm. Bore 754 is circular in shape and extends upwardly from the under surface of the arm 750. Bore 754 opens into bore 756. Bore 756 is, in cross sectional planes parallel to the longitudinal axis through the bore 756, generally in the shape of a rounded triangle. Bore 756, in cross section, subtends an area less than the cross sectional are of bore 754. Not identified is the step in the arm between bore 754 and bore 756. Bore 756 is close ended. A closed end cylindrical bore 757, seen in phantom only in FIG. 53, extends upwardly from the top of the closed end of bore 756.

Figure 54:
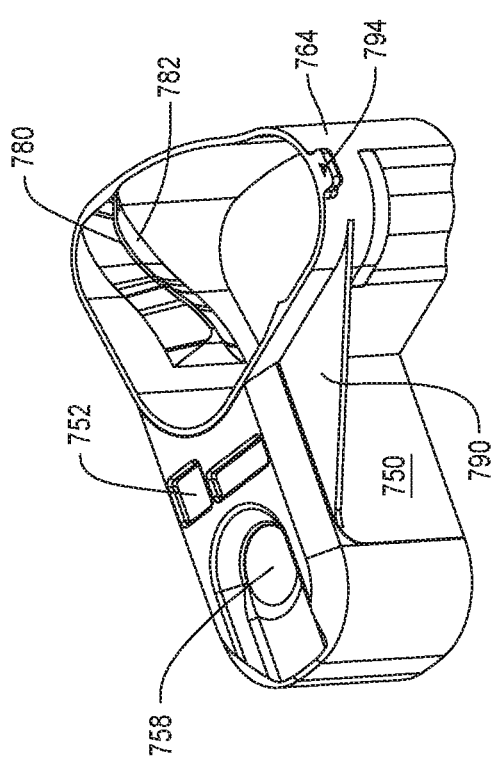
FIG. 54 is a first perspective view of the top of the arm.
Figure 55:
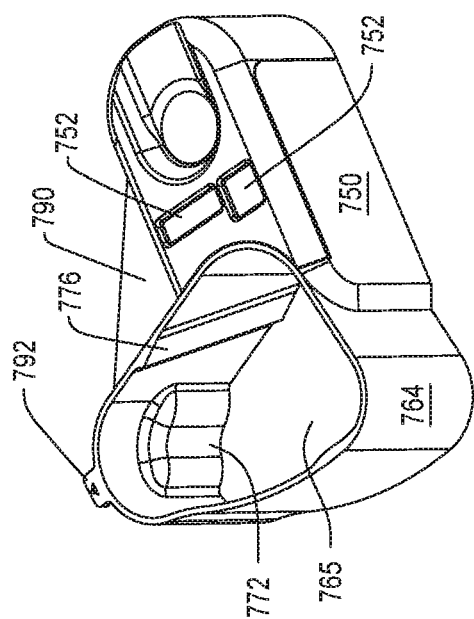
FIG. 55 is second perspective view of top of the arm.

The arm 750 is further formed so as to have a dimple 758, identified in FIG. 54, that extends inwardly from the top surface of the arm. Dimple 758 is concave in shape. The dimple 758 is formed in the arm to be concentric with bore 754. Arm 750 is formed so that when the shell 650 is fitted over the base 604, the shell boss 676 is seats in the dimple 758. A void 759 is seen extending upwardly from the undersurface of the arm 750. Void 759 is separate from bores 754 and 756. The void 759 is present for manufacturing reasons only.

The cage 764 is a structure generally formed as a triangle with rounded vertices. The cage 764 extends outwardly from the end of the arm 750 opposite the curved end of the arm. Arm 750 and cage 764 are formed so that a relatively short length panel 766 of the cage 764 extends along a line that is approximately parallel to the longitudinal axis of the arm. A medium length panel 768 of the cage extends generally perpendicularly from the short length panel and is adjacent the arm 750. The longest length panel 770 of the cage, essentially that panel that is the hypotenuse of the triangle formed by the cage, extends between the free ends of panels 766 and 768. Cage panel 770 is spaced away from arm 750.

Cage 764 is formed to have structural features that extend inwardly from the surfaces of the panels 766-770 into the void space 765 internal to the cage. One of these structural is an indentation 769 in panel 770.

Indentation 769 is located adjacent the curved vertex between panels 768 and 770. Indentation 769 appears to extend into void space 765.

A second structural feature that extends into void space 765 is a press block 772. The press block 772 consists of portions of the panel 768 and the portion of the adjacent curved vertex that forms the section of the cage between panel 768 and panel 770. The press block 772 has a face that is located inwardly of the inner surfaces of panel 768 and the adjacent curved vertex. The cage 764 is formed so the press block 772 extends upwardly from the bottom edge of the panel. The press block 772 extends approximately half the distance up the top-to-bottom distance of the cage. The press block 772 presents a curved face to the void space defined by the cage. More particularly, the press block 772 is curved so that the face has a curvature that, in planes perpendicular to the bottom-to-top longitudinal axis along the press block, is concave.

A third structural feature of the cage 764 that projects into void space 765 is a rib 776 that extends inwardly from the inner surface of panel 768. Rib 776 has a shape that, in planes perpendicular to a bottom-to top axis along the panel 766, is triangular. The apex line along the rib 776 is the portion of the rib spaced furthest from panel 766. Rib 776 does not have a longitudinal axis that simply extends perpendicularly upward from the bottom of the panel 768. Instead, at the bottom of the panel, the base of rib 776 is located within an area subtended by the arm 750. Extending upwardly from this portion of panel 768, the rib 776 extends diagonally towards the curved vertex between cage panels 768 and 770. Thus, the top portion of rib 776 is integral with a section of the panel 768 that is spaced away from the arm 750.

A rib 780 is the fourth structural member of the cage 764 that extends into void 765. Rib 780 extends inwardly from the inner surface of panel 766 and the curved vertex between panel 766 and panel 770. In planes that extend vertically, top to bottom along the cage 764, rib 780 has a cross sectional shape that is generally triangular. Cage 764 is further formed so that the apex of rib 780 extends along a line that is not parallel to the bottom of the cage. Instead, the cage is formed so that the end of the rib 780 that extends outwardly from panel 766 projects outwardly from a location generally near the mid-section between the top and bottom of the panel 766. As the rib extends away from panel 768 and curves around vertex that leads to panel 770, the rib extends upwardly. The second end of the rib 780 thus terminates at the top edge of the cage where the vertex between panels 768 and 770 curves into panel 770. Rib 780 has a surface 782 below the apex of the rib. Surface 782 tapers upwardly from both panel 766 and vertex between panels 766 and 770. Starting where vertex 771 curves away from panel 770, surface 782 curves around and downwardly along around the vertex. From the vertex, as the surface 782 extends along panel 766, surface 782 extends downwardly.

A web 790 extends between the outside of arm 750 and the outer surface of cage panel 768 that projects away from the arm. A tab 792 extends outwardly from the top of the cage 764. More particularly, the tab 792 projects outwardly from the top of vertex 769. Tab 792 is formed with an arrow head shaped icon 794 that points away from the cage 764

Figure 57:
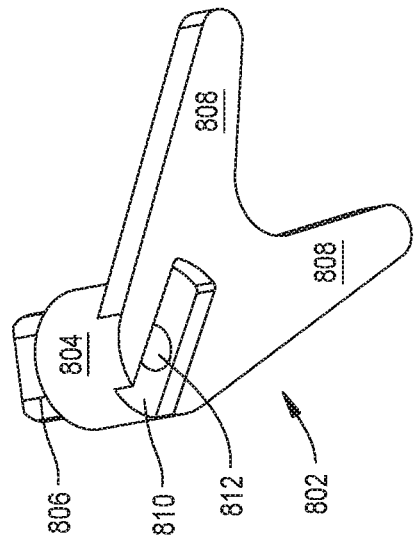
FIG. 57 is a perspective view of the undersurface of the drive pin.
Figure 56:
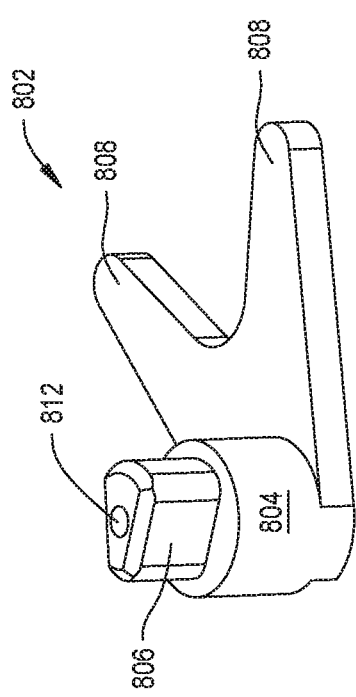
FIG. 56 is a perspective view of the top of the drive pin internal to the cleaning module.

A drive pin 802, best seen in FIGS. 56 and 57, is mounted to and extends outwardly from arm 750. The drive pin 802 includes a cylindrical stem 804. Stem 804 is dimensioned to seat in bore 754 formed in the arm 750. Stem 804 has a diameter approximately equal to the diameter of head 490 of arm coupler 486 that is part of the assembly base 102. A head 806 extends upwardly from the stem 804 of pin 802. Head 806 is triangular in shape and subtends a cross sectional area that is within the circle defined by stem 804. The pin head 806 is dimensioned to tightly fit in the bore 756 formed in the arm 750.

The drive pin 802 is further formed so that at the base of stem 804, the end of the stem opposite the end from which head 806 extends, two toes 808 extend away from the stem. Toes 808 lie in a common plane. The toes 808 are arcuately spaced apart from each other. Drive pin 802 is shaped so that each toe 808 has an outer side surface that essentially extends tangentially away from the curved wall that forms that outer surface of pin stem 804.

Drive pin 802 is further formed so as to have a slot 810 that extends upwardly from the base of stem 810. The slot 810 is rectangular in shape and is dimensioned to receive the bar 492 integral with the assembly base arm coupler 586. In the illustrated version of the invention, slot 810 projects slightly radially beyond the stem 810 into a web between toes 808. A bore 812 extends upwardly from the inner surface of stem 804 that defines the ceiling of slot 810. Bore 812 extends through the stem 804 and head 806.

Upon assembly of the cleaning module 602, the arm 750 is positioned so the bores 754 and 756 are located over opening 630 in the module base 604. As a result of the positioning of the arm 750, the cage 770 is disposed over plate 710 to surround the fluted screw 690 and the surrounding tube 724. The drive pin stem 804 is inserted in opening 630 so the stem and head seat in, respectively, bores 754 and 756 formed in the arm. A fastener 814, seen only in FIG. 46, that extends through pin bore 812 and bore 757 internal to arm 750 holds pin 802 to the arm 750. The toes 808 and slot 810 integral with the drive pin are located adjacent the undersurface of plate 604, the surface of the plate opposite the surface against which arm 750 rests.

Figure 60:
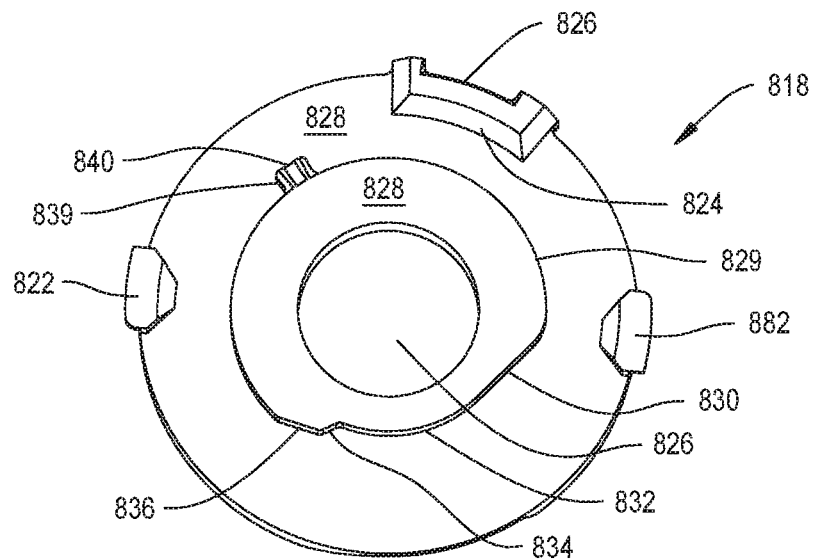
FIG. 60 is a perspective view of the top of the lock plate internal to the cleaning module.
Figure 61:
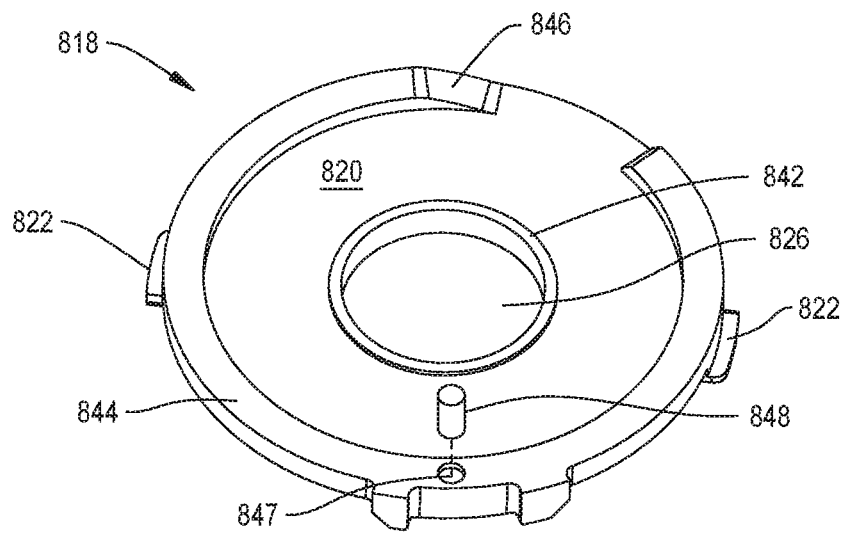
FIG. 61 is a perspective view of the bottom surface of the lock plate.

A lock disc 818, now described by reference to FIGS. 60 and 61, is rotatingly mounted to the module base 604 so as to be located below the undersurface of plate 604. Lock disc includes a circular plate 820. Two tabs 822 are disposed on the top surface of the plate 820. The tabs 822 are diametrically opposed to each other relative to the center of the plate. Each tab 822 extends upwardly from the top surface of the plate 820. The portion of the tab 822 that is disposed above the plate top surface projects radially outwardly beyond the perimeter of the plate 820. A ridge 824 also extends upwardly from the top surface of plate 820. Ridge 824 is a three section structure, individual sections not identified. There is a center section located adjacent the perimeter of the plate 820. This center section is curved in shape and subtends an arc of approximately 20 to 30°. Two end sections project radially outwardly from the opposed ends of the middle section. The end sections project a short distance, approximately 5 mm, beyond the perimeter of the plate. Ridge 824 thus defines a mortise 826 located adjacent the outer perimeter of the plate 820.

The lock disc 818 is further formed to have a center located through hole 826. The lock disc 818 is formed so that hole 826 has a diameter that the outer ring 624 of the module base 604 can seat in the hole and the disc 818 can rotate around the ring 624. An atoll 828 formed integrally with plate 820 extends upwardly from top surface of the plate and extends around hole 826. The atoll 828 is formed to have outer side surfaces that are located different distances from the center of hole 826. A first side surface, surface 829 the edge of which is identified, is an arcuate surface that is located furthest from the center of hole 826. The atoll is formed so that surface 829 subtends an arc that extends more than 180° around the perimeter of the atoll 828. At one end, surface 829 curves into a surface 830. Surface 830 goes along a path around hole 826 that is generally linear in shape. Surface 830 merges into an arcuate surface, surface 832. Surface 832 is centered around center the center of hole 826. Relative to surface 829, surface 832 is located closer to hole 826. A linear surface, surface 834, extends both arcuately and radially outwardly away from surface 832. Surface 834 extends to an adjacent linear surface, surface 836. Surface 836 is located along a line that is approximately parallel to the tangent line that would be present on surface 832, where surfaces 832 and 834 meet. Surface 838 extends to surface 829.

The lock ring 818 is further formed so that a tab 839 extends radially outwardly from the surface 828 of the atoll 828. Tab 839 is formed with an indentation 840. The indentation 840 is dimensioned to receive either one of the ribs 634 or 636 that extend downwardly from the module base 604.

A ring 842 extends downwardly from the undersurface of the lock disc 818. Ring 842 extends circumferentially around hole 826. A rim 844 also extends downwardly from the undersurface of the plate 824. The rim 844 extends downwardly from the outer perimeter of the disc 818. The rim 844 does not extend completely circumferentially around the outer perimeter of the plate 824. The plate has a section that subtends an arc of between approximately 30 and 50° that is rim free. One end of the rim 844 is formed to have a ramp surface, surface 846. As surface 846 extends arcuately, the surface tapers away from the surface of the plate 824 towards bottommost surface of the rim 844.

Lock ring 818 is further formed to have a closed end bore 847 that extends upwardly from bottom directed face of ring 842. Bore 847 is located in the portion of the ring above ridge 824. A magnet 848 is disposed in bore 847.

Cleaning module 602 is assembled by positioning the lock disc 818 adjacent the underside of the base 604 so outer ring 624 seats in hole 826 and extends downwardly a short distance beyond the disc. As a result of this positioning of the lock disc. Toes 808 integral with the drive pin 802 are disposed on the surface of the disc adjacent the atoll 828. A retaining ring 849 is seated against the stepped surface between the rings 624 and 626 integral with the module base 604. Fasteners 851, one identified in FIG. 72, extend through holes in the ring 849 and bores 628 in the base to hold the ring to the base. Ring 849 has an outer diameter greater than the diameter of the hole 826 internal to the lock disc 818. The ring 846 thus projects under the ring 842 integral with the module base 604. Ring 849 thus holds the lock disc to the module base 604. When the cleaning module is assembled, the lock disc 818 is spaced below the undersurface of plate 606. Tabs 822 and mortise 826 are disposed in the space between plate 606 and disc 818. The mortise 826 is accessible through slot 614 in ring 608 integral with the module base 604.

Figure 59:
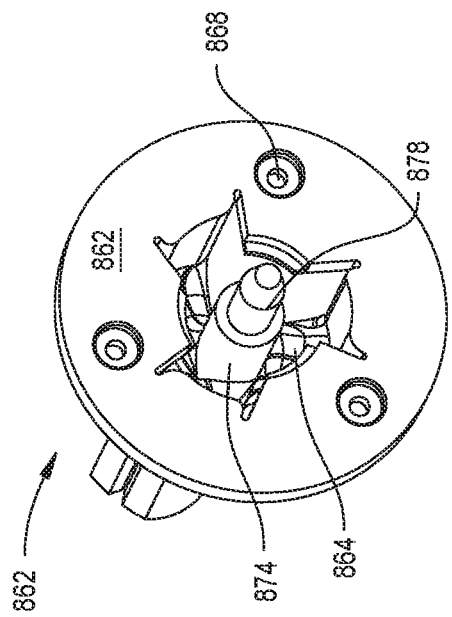
FIG. 59 is a second perspective view of the hub of FIG. 58.
Figure 58:
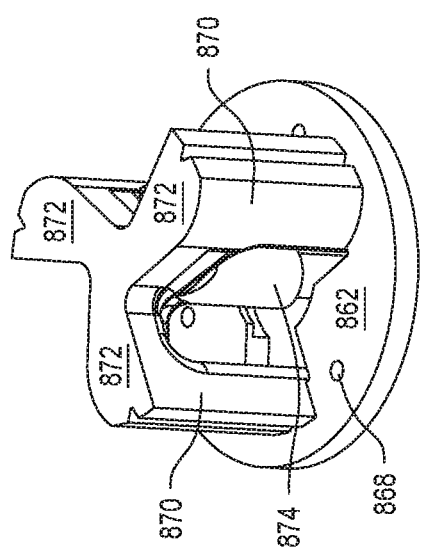
FIG. 58 is a first perspective view of the hub integral with the cleaning module.

A hub 860, seen best in FIGS. 58 and 59, is disposed in catch space 682 internal to the cleaning module 602. Hub 860 is a single piece component. The hub 860 has a disc shaped base 862. Base 862 is formed with a center opening 864 that extends between the opposed downwardly and upwardly directed surfaces of the base. The downwardly directed surface of base 862 is understood to be the surface that is faces the underlying shell lid 670. Three bores 868, one bore identified, that are spaced radially outwardly of opening 864 and equangularly spaced apart from each also extend between the opposed downwardly and upwardly directed surfaces of base 862. Each bore 868 has a counterbore, (counterbores not identified). Hub 860 is shaped so that when the base 862 is positioned so that the hub center opening 864 is disposed over the opening 672 in the shell lid 670, each one of the bosses 673 formed in the lid 670 seats in separate one of the counterbores associated with bores 868. Fasteners that extend through the lid bosses and the hub bores 868 hold the hub to the top of the shell lid 670, fasteners not illustrated.

Three equangularly spaced apart stanchions 870, two stanchions identified, also part of the hub 860, extend upwardly from the outer surface of the base 862. The stanchions 870 are located on a circle located adjacent the perimeter of the center opening 864. A web 872 extends radially inwardly from the top of each stanchion 870. Webs 872 meet at a location above the center of center opening 864. A pin 874 extends downwardly from the location where webs 872 meet. A foot 878 extends below the free end of the pin 878. Foot 878 has a diameter less than the diameter of the pin 874. More particularly, the pin foot 878 has a diameter that allows the pin foot 878 to closely slip fit in bore 704 formed in the fluted screw. When the cleaning module 602 is assembled, the pin foot 878 seats in fluted screw 690 and the screw is able to rotate around the pin 874.

A latch 880, see best in FIGS. 47 and 48, is moveably mounted to the shell 650. The latch 880 is formed with a number of panels such that the panels forming the latch are located adjacent the shell inner wall 656 and adjacent webs 658, 660 and 666. Two arcuately shaped beams 882 extend downwardly from one of the panels. An arcuate shaped lip 884 projects outwardly from the top most webs. The components forming the cleaning module 602 are formed so that the latch 880 can be snap fitted to the shell such that beams 882 seat over shell web 666 and lip 884 seats in shell groove 655. The latch 880 subtends an arc less than the arc subtended by the shell inner wall 656 and adjacent webs 658, 660 and 666. The latch 880 can thus slide over the shell inner wall 656 and adjacent webs 658, 660 and 666.

The bottommost panel of the latch 880 extends below shell web 658. A tab 886 projects perpendicularly away from the bottom edge of the bottommost panel of the latch. Tab 886 thus extends below and inwardly from the bottom edge of shell web 658. The latch is shaped so that the tab 886 can seat in the mortise 826 defined in lock disc 818.

IV. Milling Module

Figure 62:
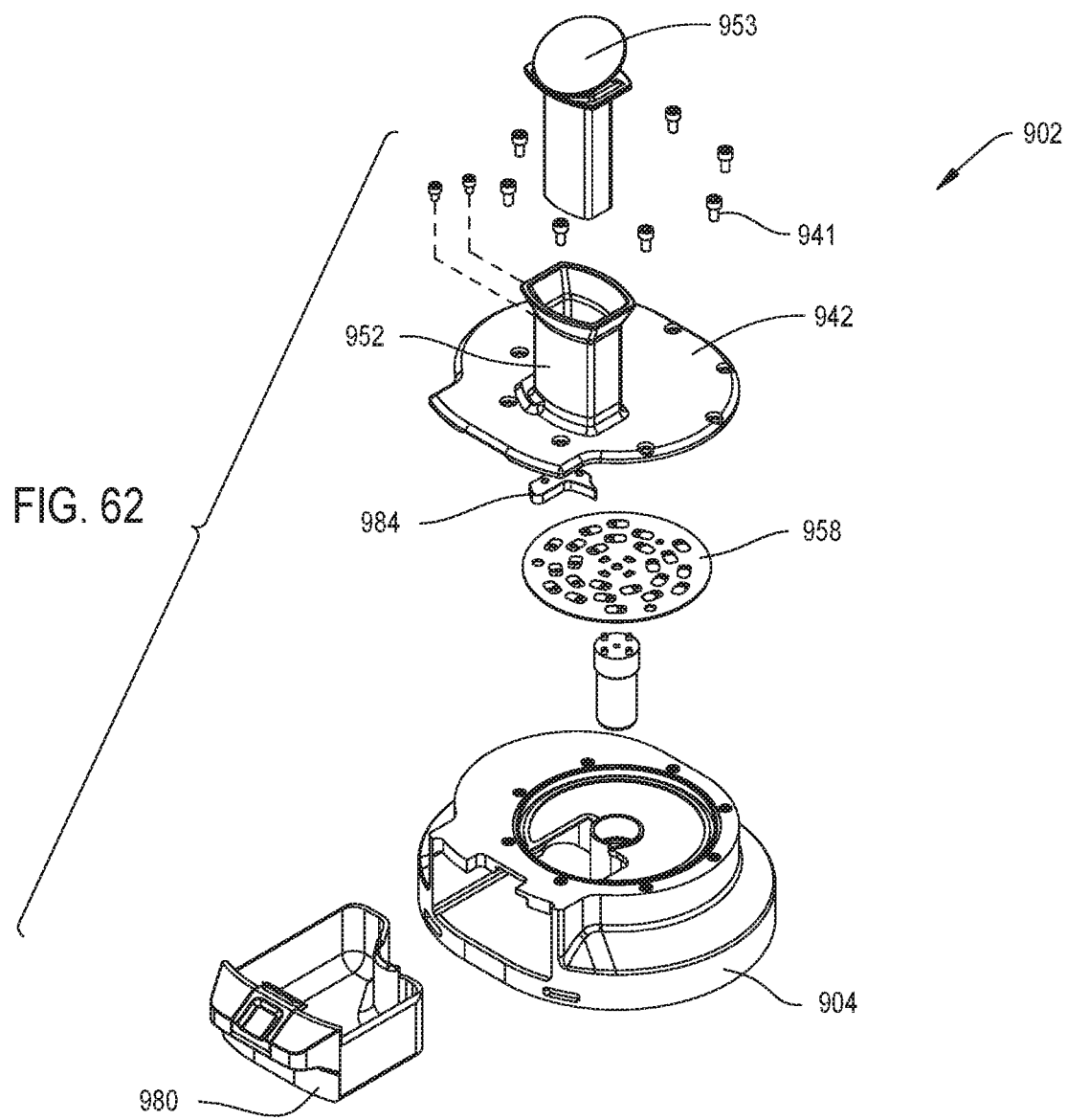
FIG. 62 is an exploded view of the milling module of the assembly of this invention.

The milling module 902 as seen in FIG. 62, includes a bottom shell 904 and a top shell 940 that collectively form the housing of the module. Top shell 940 is disposed above the bottom shell 902. A cutting disc 958 and an impingement plate 984 are disposed between the shells 902 and 940. A hopper 952 extends upwardly from the top shell 940. A plunger 953 can be pushed through the hopper 952. A catch tray 980 is removably attached to the bottom shell 904 below the cutting disc 958.

Figure 63:
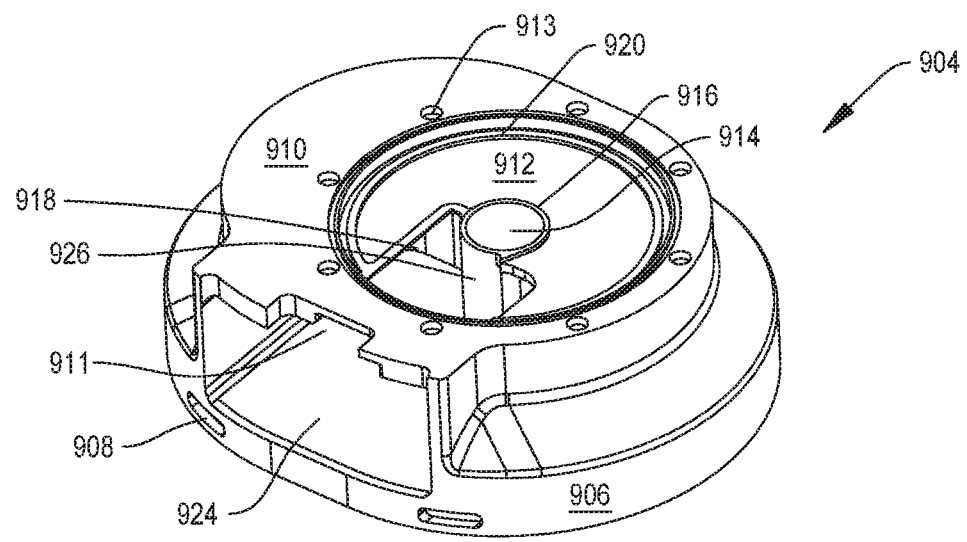
FIG. 63 is a perspective view of the top of the shell of the milling module.
Figure 64:
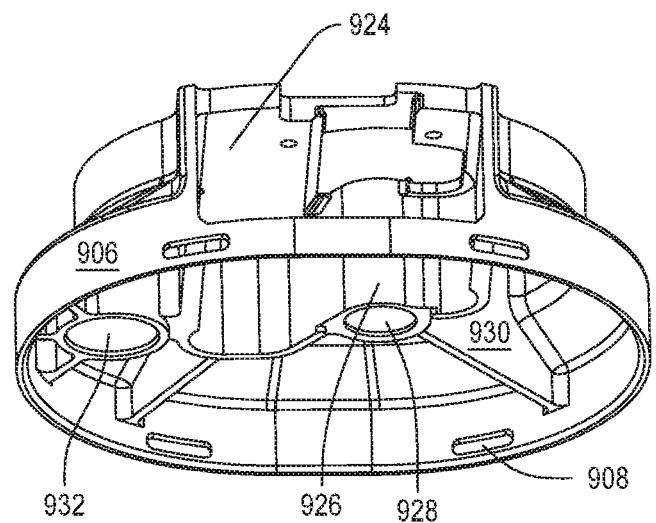
FIG. 64 is a perspective view of the underside of the shell of the milling module.

As seen in FIGS. 63 and 64, bottom shell 904 integral with the cleaning module has a rim 906. The rim 906 is dimensioned to seat on the step 115 that extends around the top of the assembly base 102. Rim 906 is formed to have four openings 908, one opening identified. Shell 904 is formed so that when the milling module 902 is seated on the assembly base 102, latch assembly tabs 548 can seat in openings 908 to releasably hold the module 902 to the base 102.

The bottom shell 904 is further formed to have a planar top surface 910. A recessed surface 912 that is generally circular in shape is located below the top surface 910. Plural bores 913, one bore identified, extend inwardly from the top surface 910. Bores 913 are located around and spaced radially outwardly from the recessed surface 912. Shell 904 is formed so that there are two openings in the recessed surface 912. A first opening, opening 914, is circular in shape and is concentric with the center of the recessed surface 912. The outlet opening, opening 918, extends inwardly from the outer perimeter of the recessed surface 912. Opening 918 extends toward opening 914. A ring 916 extends upwardly from the recessed surface 912 and circumferentially surrounds opening 914. Ring 916 functions as a barrier between opening 914 and opening 918. Shell 904 has a second ring, ring 920, that also extends upwardly from recessed surface 912. Ring 920 is located immediately inward of the outer perimeter of the recessed surface 912. Ring 920 does not extend circumferentially around recessed surface 912. Instead, opening 918 interrupts ring 920.

Bottom shell 904 is further formed to have a number of panels that extend upwardly from the rim 906 to the top surface 910, (panels not identified). One of the side panels is formed with an opening 924. Opening 924 extends inwardly into the shell and is positioned to be located below and contiguous with opening 918. The bottom shell 904 is also shaped so that the panel of the shell that forms top surface 910 is shaped to have a notch 911. Notch 911 extends inwardly from the portion of the top surface-defining panel that defines opening 924

A sleeve 926 extends downwardly from the underside of the shell recessed surface 912. Sleeve 926 defines a through bore 928 that extends downwardly from opening 914. The bottom shell 904 is further formed so a number of webs 930 extend downwardly from the undersurface of the top surface and inwardly from panels that form the side of the shell. Webs 930 provide structural shape to the bottom shell. One of the webs 930 defines an upwardly extending opening 932. The bottom shell 904 is shaped so that when the milling module 902 is placed on the assembly base 102, bore 928 is centered over the primary coupler 194 and opening 932 is centered of the arm coupler 486.

Figure 65:
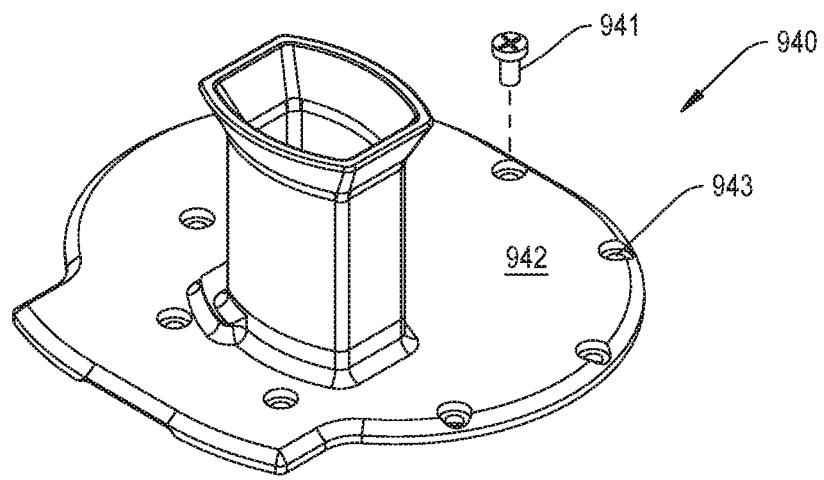
FIG. 65 is a perspective view of the top of the top plate and hopper of the milling module.
Figure 66:
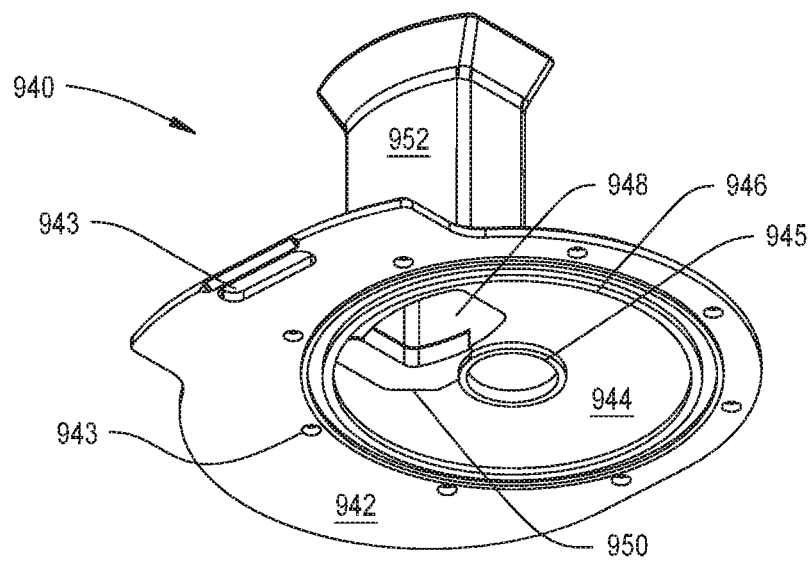
FIG. 66 is a perspective view of the underside of the top plate and hopper of the milling module.

The top shell 940, now described by reference to FIGS. 65 and 66, integral with milling module 902 has a planar shaped base 942. The shell base 942 is dimensioned to seat over the top surface 910 of the bottom shell 904. Top shell 940 is formed to have a circularly shaped raised surface 944 that is located above the planar bottom face of the base 942. A set of openings 943, extend top to bottom through the portion of shell 940 that defines the base 942. Openings 943 are located around and radially outwardly from the raised surface 944. Milling module 902 is formed so the raised surface 944 is positioned to be concentric with and have the same diameter as the recessed surface integral with the bottom shell recessed surface 912. Each opening 943 is centered above a bottom shell bore 913. Fasteners 941, one seen in FIG. 65, extend through each top shell opening 943 into the underlying bottom shell bore 913. The fasteners 941 thus hold the top shell 940 to the bottom shell 904.

Two rings that are concentric with the raised surface 944 extend downwardly from base 942. An inner ring 945 extends downwardly from surface 942 adjacent the center of the surface. An outer ring 946 extends downwardly from the raised surface and is located slightly inward of the outer perimeter of the raised surface. More particularly, when the milling module 902 is assembled, ring 945 is disposed over the ring 916 integral with the bottom shell 904. The outer ring 946 is disposed over the underlying ring 920.

The shell base 942 is further formed to have a notch 943. Notch 943 is oval in shape. The notch 943 is positioned so that, upon assembly of module 902, the notch is located immediately above the notch 911 formed in the top surface 910 of the bottom shell. Notch 943 does not extend completely through the base 942.

Base 942 of the top shell 940 is further formed to have an inlet opening 948. Inlet opening 948 opens into a section of raised surface 944 between rings 944 and 946. More particularly, the top shell opening 948 is positioned to be in registration over the bottom shell opening 918. Top shell 940 is further formed so that the hopper 952 extends upwardly from the shell base 942 around inlet opening 948. The base 942 of top shell 940 is also formed to have a cavity 950, the edge of which is identified in FIG. 66. Cavity 950 extends upwardly from the raised surface 944. The top shell 940 is formed so that cavity 950 is adjacent and contiguous with inlet opening 948.

Cutting disc 958, seen best in FIG. 67, is circular in shape and is dimensioned to sit in the space between the bottom shell recessed surface 912 and the top shell raised surface 944. More particularly, the cutting disc 958 rests on the rings 916 and 920 that extend above the recessed surface 912. The cutting disc has a diameter approximately 4 mm less than the diameter of the void space in which the disc is seated. The cutting disc 958 has a thickness approximately 0.25 mm less than the distance separating the bottom shell rings 916 and 920 from the top shell rings 945 and 946. The cutting disc 958 is thus capable of rotating in the void space in which the disc is seated as well as a limited amount of side to side movement and a limited amount of up and down movement.

The cutting disc 958 is formed with plural cutting elements 960, one element identified. The exact structure of the cutting elements 960 are not part of the current invention. One such structure of cutting elements is disclosed in the incorporated by reference U.S. Pat. Pub. No. US 2009/0118735/PCT Pub. No. 2009/061728. Generally, it should be understood each cutting element has a shearing edge 962, (one edge identified). Each shearing edge 962 defines a portion of an opening 963 in the cutting disc 958, one opening identified. The cutting disc is further formed to have four equangularly spaced apart openings 964 (one opening identified). The openings 964 are located radially inward of the cutting elements 960.

A shaft 966, seen best in FIGS. 68 and 69, extends downwardly from the center of the cutting disc 958. The shaft 966 is generally cylindrical in shape. The shaft is formed to have a head 970. The shaft head 970 has a diameter that allows the head to seat in and rotate in bore 928 internal to the bottom shell 904. A cylindrical stem 972 extends below the head 970. Stem 972 has a diameter less than that of the head 970. The shaft is formed so a closed end bore 974 extends upwardly from the bottom of the stem 972. The bore 974 is centered on the longitudinal axis of the shaft 966. Bore 974 is dimensioned to receive the pin 198 integral with primary coupler 194. The shaft 966 is further formed so as to have three equangularly spaced apart notches 976 that extend radially outwardly from the base of bore 972. The notches 976 do not extend as far upwardly into the shaft stem 972 as bore 974. Notches 976 are dimensioned to receive the teeth 202 integral with the primary coupler 194.

Four pins 980, one pin identified, extend upwardly from the top surface of shaft head 970. Pins 980 extend through and over the opening 964 internal to the cutting disc 958. The pins 980 thus hold the shaft 966 to the cutting disc 958. When the milling module 902 is assembled, shaft 966 is disposed in bore 928 internal to the bottom shell 904.

An impingement plate 984, seen in FIG. 62, is mounted in cavity 950 formed in the top shell 940. The impingement plate 984 is formed to have a surface that is immediately below inlet opening 948. Milling module 902 is designed so that when the module is actuated, the shearing edges 962 of the cutting disc rotate towards the over surface of the impingement plate 984.

Figure 70:
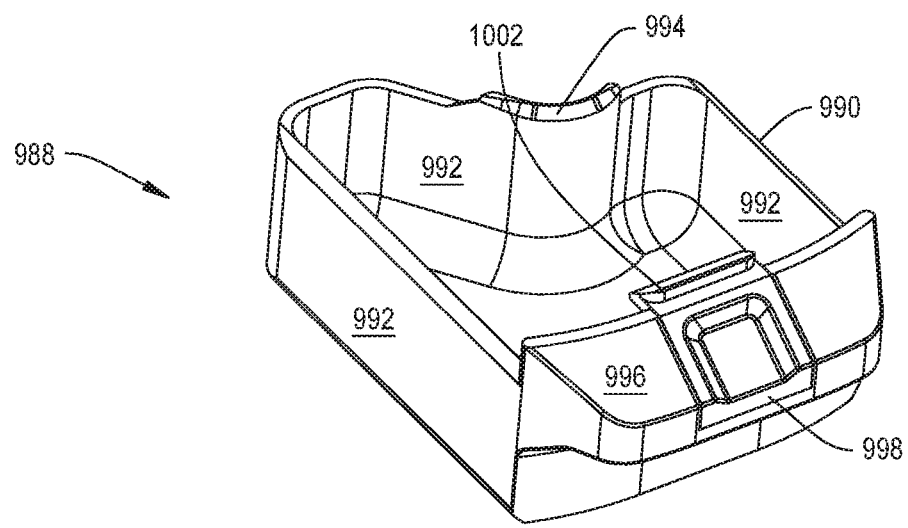
FIG. 70 is a perspective view of the top of the catch tray that is fitted to the milling module.
Figure 71:
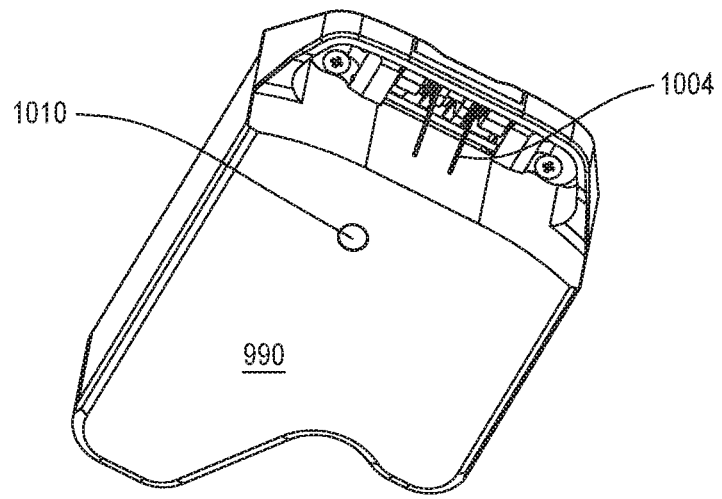
FIG. 71 is a perspective view of the underside of the catch tray.

The catch tray 988, now described by reference to FIGS. 70 and 71, is dimensioned to slidably seat in opening 924 internal to the bottom shell 904. The catch tray 988 has a base 990 from which a set of panels 992 extend upwardly, three panels identified. A lip 994 extends upwardly from the innermost panel 992, the panel located closest to the shell sleeve 926. Catch tray 988 is formed so that when the tray is removed from the rest of the milling module 902, the lip sweeps under the section of the cutting disc 958 located immediately above opening 918.

A handle 996 also projects outwardly from the outermost panel 992, the panel spaced furthest from the panel from which the lip 994 extends. Handle 996 extends in front of the panel with which the lip is associated. Handle 996 functions as the portion of the catch tray the user grasps to insert the tray in and remove the tray from the rest of the milling module 902.

A latch 998 is pivotally mounted to handle 996. Latch 998 includes a tab 1002 that projects above the rest of the catch tray 988. Tab 1002 is positioned so that when the catch tray is full seated in opening 924, the tab is seated in the notch 943 internal to the top shell 940. Springs 1004, one spring identified, place a force on the latch that normally holds the latch in the locked state, the state in which tab 1002 is disposed in notch 943. Finger force on the body of latch 998 is sufficient to overcome the force imposed by the springs 1004 so as to pivot the latch 998. The pivoting of the latch 998 rotates tab 1002 out of the notch 943. Once the tab 1002 is so rotated, the catch tray 988 can be removed from the rest of the milling module 902.

A magnet 1010 is mounted in the base 990 of the catch tray 988. Not identified is the bore in the base 990 in which the magnet 1010 is seated. The components forming assembly 100 of this invention are arranged so that when the catch tray 988 is latched in the milling module 902 and the cleaning module is seated on the assembly base 102, magnet 1010 is located above sensor 587.

V. Operation

A first step in preparing assembly 100 of this invention for use is the connection of the console containing the power supply 595 and/or motor controller 596 to the assembly base 102. This step is required if these sub-assemblies are separate from the assembly base 102. The cleaning module 602 is then seated over the top plate 122 of the assembly base. More particularly, the cleaning module 602 is fitted to the assembly base so that tabs 548 that are part of the latch assembly 540 extend through the slots 612 in the cleaning module. Spring 566 exerts sufficient force on latch plates 542 and 544 and, by extension, latch plates 546, to maintain tabs 548 in their outwardly directed positions. When the tabs 548 are in the outwardly directed positions, latch assembly 540 is in the latched state.

Figure 72:
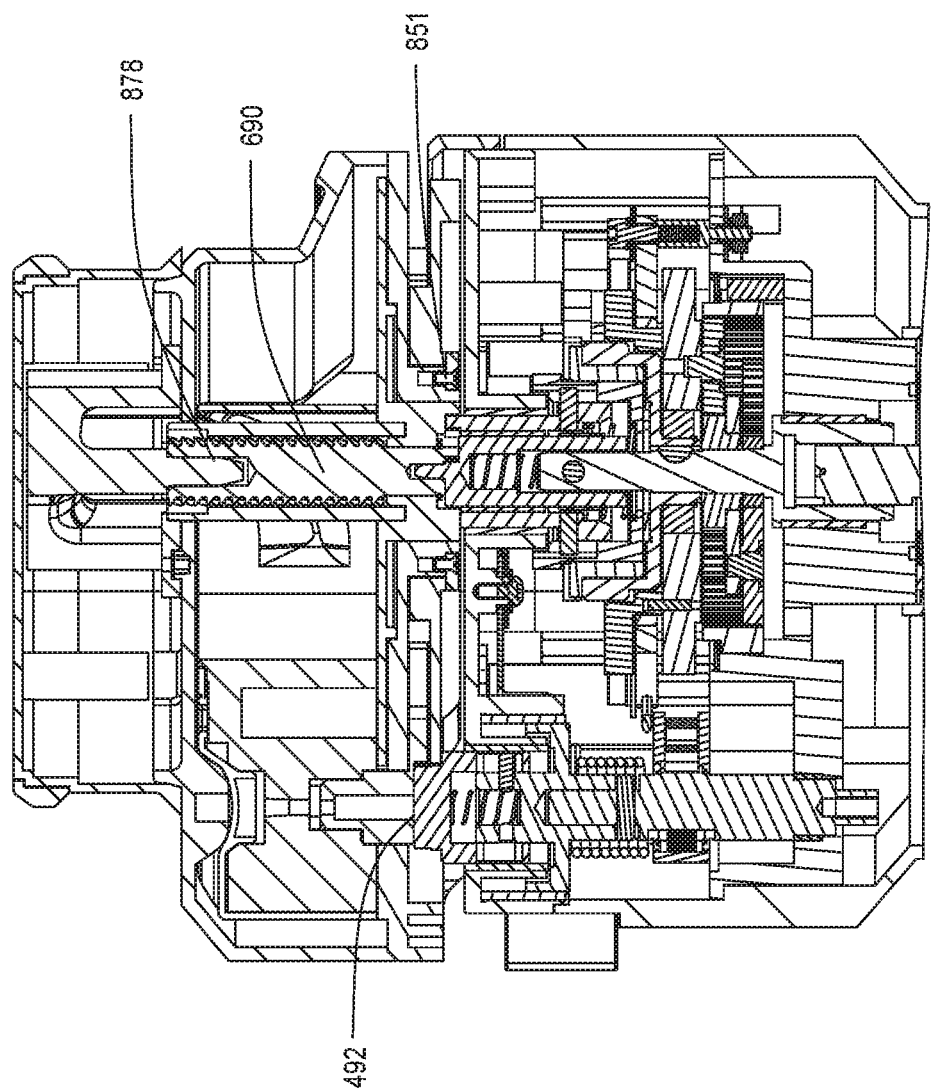
FIG. 72 is a cross-sectional view of the cleaning module mounted to the assembly base.

When the cleaning module 602 is latched to the assembly base 102, stem 692 of fluted screw 690 is disposed over the primary coupler 194 as seen in FIG. 72. If the coupler teeth 202 are not seated in overlying flute notches 702, the coupler 194 bears down against spring 212. The notch 718-defining portion of the boss 712 integral with plate 710 is disposed over the tube coupler 348. If teeth 353 integral with the tube coupler 348 are not seated in notches 718, the tube coupler 348 pushes down against spring 394. Stem 804 of drive pin 802 is disposed over cage coupler 486. If the bar 492 integral with the arm coupler 486 is not seated in slot 810 integral with the drive pin, the arm coupler pushes down against spring 504.

To place the bone stock to be cleaned in module 602 it is necessary to lift the shell 650 off the module base 604. To remove the shell 650, the latch 880 is rotated to the unlocked state. This would mean rotating latch 880 counterclockwise as the latch is viewed in FIG. 1. This rotation of the latch through the engagement of tab 886 against mortise 826 results in a like rotation of the lock plate 818. As a result of this rotation of the lock plate 818, the lock plate tabs 822 rotate clear of the tabs 653 integral with shell 650. This allows the shell to be removed from the base 604.

A further result of the rotation of the lock plate 818 is that magnet 848 rotates away from sensor 586. In many versions of the invention, the motor controller 596 is configured to allow the motor 140 to be actuated when a signal from a single one of the sensors 586 or 587 indicates that there is a magnet in close proximity to the sensor. When the lock plate 818 is in the unlocked position no magnet adjacent either sensor 586 or sensor 587. This means that depressing of either switch 588 or 590 will not result in the actuation of the motor 140.

Also as a result of the rotation of lock plate 818, atoll 828 integral with the lock plate rotates so atoll surface 829 is rotated against one if not both of the toes 808 of the drive pin 802. The rotation of the toes 808 results in a like rotation of the drive pin 802 and, by extension, the pivoting of arm 750 and cage 764. Specifically, the cage 764 is positioned to the orientation relative to the flutes screw seen in FIG. 77D. As a result of the abutment of the at least one toe 808 against atoll surface 829, the drive pin 802 and therefore arm 750 and cage 764 are inhibited from further movement.

When latch 880 is rotated to the unlocked position, further rotation of the latch is blocked by the abutment of tab 839 integral with atoll 828 abutting the stop 632. When the lock plate 818 is so positioned, rib 634 seats in indentation 840 to releasably hold the lock plate, and by extension, latch 880 in the unlocked position.

The bone stock to be cleaned and milled is then placed void space 765 internal to the cage 764. Shell 650 is seated back over the module base 604. As result of the seating of the shell on the base 604, pin foot 878 integral with hub 860 seats in bore 704 internal to the fluted screw 690. Latch 880 is rotated to the position shown in FIG. 1 to return the shell to the locked state. As a result of this rotation of the latch lock plate 818 is rotated to the locked state. Lock plate 818 is rotated so the lock plate tabs 822 seat over the tabs 653 integral with shell 604. This tab-over-tab registration is what releasably locks the shell 650 to the base 604.

Figure 74:
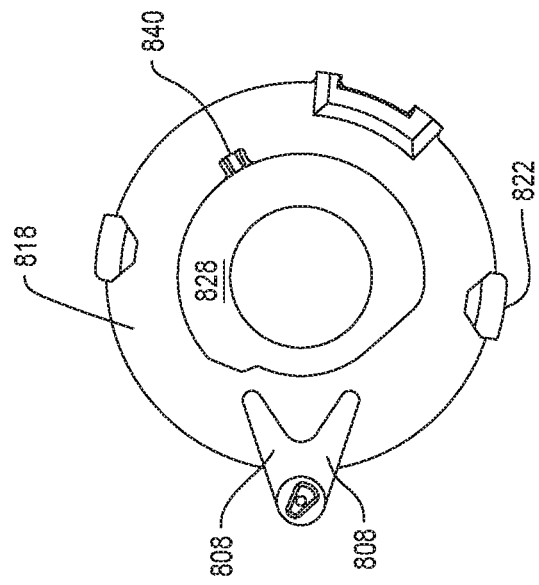
FIG. 74 depicts the relationship of the lock plate to the drive pin internal to the cleaning module when the lock plate is in the unlocked state.

As a result of the rotation of lock plate 818, the lock plate atoll 828 assumes the orientation relative to toes 808 integral with drive pin 802 as seen in FIG. 74. More specifically the atoll 828 spaces away from the toes 808. This means the drive pin and by extension arm 750 and cage 764 are free to rotate.

When latch 880 is rotated to the locked position, further rotation of the latch is blocked by the abutment of tab 839 integral with atoll 828 abutting the stop 638. When the lock plate 818 is so positioned, rib 636 seats in indentation 840 to releasably hold the lock plate, and by extension, latch 880 in the locked position.

The rotation of the lock plate 818 to the locked position also results in the rotation of magnet 848 so the magnet rotates over sensor 586. Sensor 586, in turn, outputs a signal to the motor controller 596 indicating a magnet is in the presence of the sensor. Motor controller 586 interprets this signal as indicating that assembly 100 is in a state in which the cleaning module 602 is attached to the base and the module shell 650 is locked to the module base 604. When the motor controller 596 determines assembly 100 is in this state, the controller actuates LED 588, the LED adjacent switch 586. This provides a visual indication that the switch that needs to be depressed to actuate the assembly is switch 586, the switch used to start the cleaning process.

Once switch 586 is depressed, the motor controller 596 actuates the motor 140 for a set period of time. Often this period of time is between 3 and 20 minutes. As discussed below, the actuation of the motor 140 results in a like rotational movement of the three couplers 194, 348 and 486. When the primary coupler 194 is rotated, spring 214 urges the coupler teeth 202 into the notches 702 of the overlying fluted screw 690. The fluted screw 690 thus rotates in unison with the primary coupler 194. Spring 394 urges the tube coupler 348 upwardly so the coupler teeth 353 seat in the notches 718 associated with the tumble plate 710. This tooth-in-slot engagement causes the tumble plate and shaving tube to rotate with the tube coupler. Spring 504 causes bar 492 of the rotating cage coupler to seat in the slot 810 integral with drive pin 802. The drive pin thus transfers the rotational motion of the cage coupler to arm 750 and cage 764.

The actual bone cleaning process consists of plural cleaning cycles. Each cycle consists of a set of phases. In this version of the invention, the motor 140, through gear train 144 and the spindle 170 continually rotates the primary coupler 194. Fluted screw 690, which is connected to the primary coupler 194, rotates with the primary coupler. The fluted screw 690 rotates even in the some of the below described phases in which the rotation of the screw may not contribute to the bone cleaning process.

The rotational movement of the spindle 170 is transferred through the gear train 220 to the arm cam 234 and the clutch cam 252. The arm cam 234 rotates in a counterclockwise when looking at the view of the cam presented in FIG. 75. The clutch cam 252, when looking at the view of the cam as presented in FIG. 76, also rotates counterclockwise.

A first phase of a cleaning cycle is the press phase. In the press phase, the inner lobe 258 of the clutch cam 252 rides against pawl 396. In FIG. 76, the roller 412 of pawl 396 is represented by a triangle. This means the clutch is in the disengaged state. Tumble plate 710 and the shaving tube 724 therefore do not rotate. Simultaneously, the outer lobe 238 of the arm cam rotates against the rocker arm 508. In FIG. 75, the roller 524 of rocker arm 508 that bears against arm cam 234 is represented by a circle. As a result, the rocker arm 508, and crank 448 cooperate to hold the shaft 422 in specific rotational orientation. This specific rotational orientation, as the orientation that, as represented by FIG. 77A being the orientation in which the cage is positioned so press block 772 is directed towards the window 728 internal to the shaving tube 724.

As a result of the cleaning module 602 having cycled through the below described sweep phase of the previous cycle, the bone chips being cleaned were previously collected in the cage void space 765 adjacent the press block 772. As discussed below the press block 772 is positioned to be located relatively close to the shaving tube window 728. A benefit of this close positioning of the press block to the fluted screw and shaving tube is that it increases the likelihood that the bone stock will be pressed against the fluted screw 690. This means that when the cleaning module 602 is in the press phase, the press block 772 presses the bone stock through the tube window 728 against the rotating fluted screw 690. Soft tissue attached to the bone stock becomes entrained in the individual rotating flutes 694. The rotating flutes 694 pull the soft tissue against the cutting edges 726 of the shaving tube 724. This movement of the tissue against the shaving tube cuts the tissue from the bone. More specifically, the movement of the rotating cutting edges 696 of the fluted screw against the static cutting edges of the shaving tube cuts the soft tissue away from the bone stock.

Prior to the cleaning module 602 cycling through an individual press phase, it is not possible to know the size and shape of the piece or pieces of bone stock that will be pressed by the press block 772 against the fluted screw 690. To ensure that press block 772 presses bone stock of varying sizes and shapes against the fluted screw 690, it will be recalled that hat 464 of the cage driver 420 is able to engage in a limited degree of rotation relative to shaft 422. Spring 534 holds the hat 464 in a specific rotational orientation around the shaft 422. More particularly, the spring 534 holds the shaft in an orientation so that if there is no bone stock against the press block 772, the hat 464, the arm coupler 486, the drive pin 802 and arm 750 cooperate to hold the cage 764 so that the press block 772 is spaced a short distance, away from the shaving tube window 728. In most versions of the invention, the cleaning module is constructed so that if there was no bone stock present adjacent the press block, when a cleaning cycle is in the press phase, the maximum distance between the press block and the outer surface of the shaving tube 724 is 8 mm. More ideally, the maximum distance between the press block and the shaving tube 724 when no bone stock is present is 4 mm.

When bone stock is sandwiched between the press block 772 and the shaving tube 724, the play between the shaft 422 and the cage 764 means that the movement of the cage does not result in an unyielding force urging the press block into its close proximity position against fluted screw 690. Instead, spring 534 places a torque on hat 464 that causes the associated components to in turn place a force on the cage 764. The force is placed on the cage to cause the press block 772 to push the bone stock through the shaving tube window 728 and into the rotating flutes 694. In some versions of the invention, assembly base 102 is constructed so that the force spring 534 causes the cage 764 to place a force on the bone stock trapped between the press block 772 and the fluted screw 690 between 8 and 40 Newtons.

During the press phase, the fluted screw 690 is subjected to side loading. The presence of the static pin 874 in the bore 704 internal to the screw 690 prevents this side loading from deflecting the fluted screw 690 to the point at which the flutes 694 start to scrape against the inner surface of the shaving tube 724.

The press phase is followed by the tumble phase. The assembly transitions from the press phase to the tumble phase as a result of the clutch cam 252 rotating so that the cam outer lobe 262 rotates against the pawl 396. The resultant pivoting of the pawl away from tab 304 shifts the clutch to the engaged state. The tumble plate 710 and shaving tube 724 therefore rotate simultaneously with and in the same direction and at the same speed as the fluted screw 690. The outer lobe 238 of the arm cam 234 continues to rotate against the rocker arm 508. Thus, the cage remains in the same position relative to the shaving tube as when module was transitioning through the press phase.

Figure 77B:
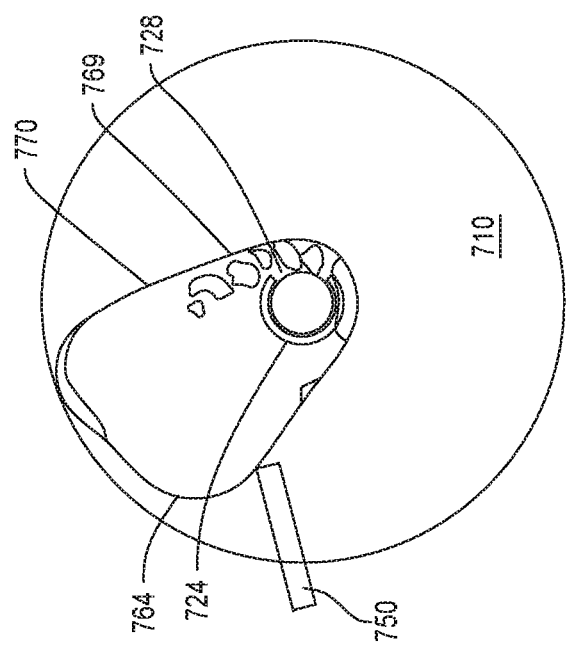
FIGS. 77A through 77E are diagrammatic depictions of the components of the cleaning module and the bone stock disposed in the cleaning module during the phases of a cleaning cycle.
Figure 77A:
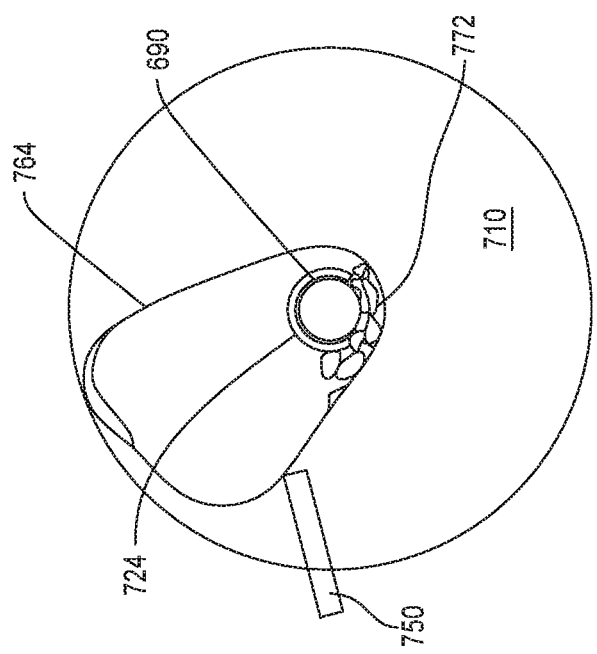

As a result of the rotation of shaving tube 724, the tube rotates the bone stock disposed in the tube window in the counterclockwise direction in the representation of FIG. 77B. This clears the bone stock out of the space between the shaving tube 724 and the press block 772.

During the tumble phase, the rotation of the tumble plate 710 may assist in the tumbling of the bone.

A shift phase follows the tumble phase. The transition to the shift phase occurs when the linear surface of the arm cam 234 between the outer lobe 238 and the inner lobe 242 rotates against the rocker arm 508. The resultant pivoting of the rocker arm 508 causes the cage driver 420 to pivot the cage 764 so that the press block 772 moves away from the fluted screw 690 and rib 780 moves towards the fluted screw as seen in FIG. 77C.

During the shift phase, outer lobe 262 of clutch cam 252 continues to ride against pawl 396. Tumble plate 710 and shaving tube 724 continue to rotate. The rotation of these components of the cleaning module during the shift phase may not appreciably contribute to the cleaning of the bone.

Figure 77C:
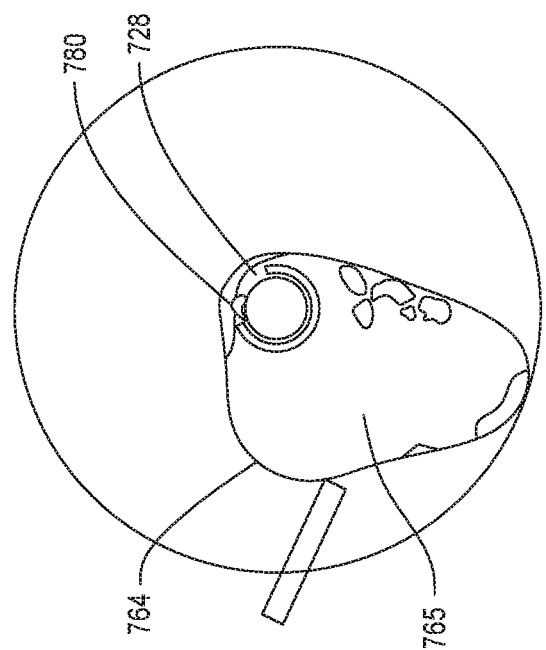

As depicted in FIG. 77C, during the cleaning process, a piece of bone stock may become caught between the relatively fast rotating fluted screw and the slower rotating shaving tube 724. This event occurs because a tail of soft tissue may be drawn into the tube window 728 and wrap around the fluted screw 690. If the tissue does not catch on a flute 694, the tissue may not be pressed against the cutting edge 726 with the force needed to cause the severing of the tissue.

Once rotation of the arm cam 234 results in the cam inner lobe 242 riding against the rocker arm 508, the assembly of this invention enters the clear and gather phase. During the clear and gather phase, outer lobe 226 of clutch cam 252 continues ride against pawl 396.

Figure 77D:
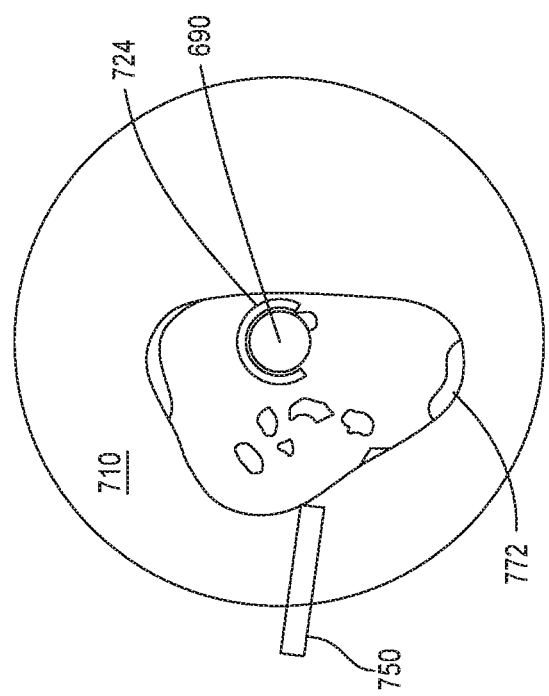

Thus during the clear and gather phase, rib 780 is in close proximity to the fluted screw and shaving tube. The fluted screw, the tumble plate and the shaving tube continue to rotate. As a result of the rotation of the tumble plate, the bone stock is rotated towards the inner surface of cage panel 770 as seen in FIG. 77D. Rib 780 thus functions as a component of the cleaning module that facilitates the clearing of trapped bone stock away from the cleaning assembly, the fluted screw and the shaving tube.

As a result of the rotation of the shaving tube, bone stock caught between the fluted screw and the shaving tube is rotated against rib 780. Most often, the bone stock is rotated against surface 782. The bone stock travels downwardly along surface 782. As the bone moves downwardly, the tail of tissue is pressed against the cutting edge of 726 of the rotating shaving tube 724. The result of this cutting edge-against-tissue action is the cutting of the tissue away from the bone stock. The bone stock is thus cut free from the fluted screw 690.

The last phase of a single cleaning cycle is the sweep phase. As a result of the rotation of the clutch cam 252, the cam inner lobe rotates against pawl 396. Tab 304 is then forced back against the pawl 396. This returns clutch 278 to the disengaged state. The tumble plate 710 and shaving tube 724 therefore stop rotating. More specifically, when this event occurs, the shaving tube 724 needs to have so the press block can be directed towards the window 728 in the following press phase.

Figure 77E:
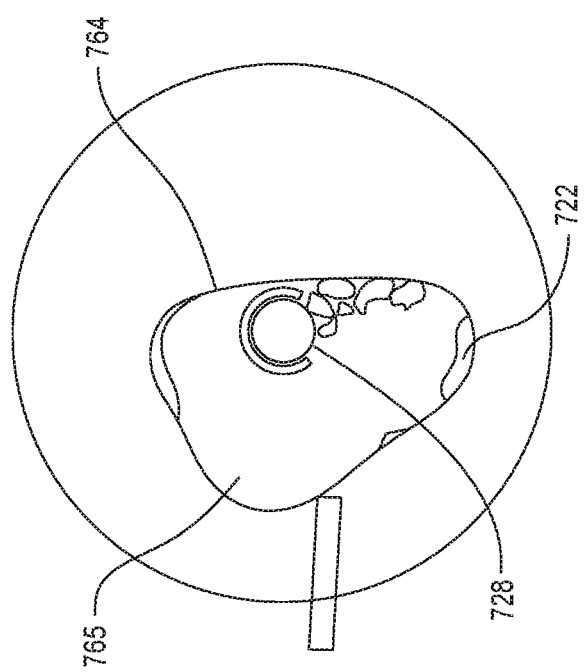

Also during the sweep phase, as a result of the rotation of the arm cam 234, the cam transition surface between the inner lobe 242 and outer lobe 238 rotates against rocker arm 508. Cage driver 420 thus pivots the cage 764, as represented by FIG. 77E, so the press block 772 is again positioned back to the position when in the press phase as represented by FIG. 77A. As a result of this motion of the cage 764, the cage pushes the bone stock disposed against panel 770 against the shaving tube window 728. Thus at the end of the sweep phase the bone stock is again pressed by the press block 772 against the window of the shaving tube.

The completion of the sweep phase concludes the movement of the cleaning module components through a single cleaning cycle. The assembly then causes the cleaning module to advance through the press phase of the subsequent cleaning cycle.

In some versions of the invention, a single cleaning cycle lasts between 3 and 20 seconds. The press phase lasts between 25 and 50% of the cycle. Ideally, during a single press phase, the fluted screw should engage in at least four 360° rotations if not at least six rotations. The tumble phase occupies between 10 and 40% of a single cleaning cycle. In a single tumble phase, the shave tube should engage in at least two complete rotations if not three or more complete rotations. The clear and gather phase typically occupies between 5 and 20% of a single cleaning cycle. The shift and sweep phases each occupy between 5 and 15% of a single cleaning cycle. In some versions of the invention once the assembly is actuated to clean the bone stock, the assembly remains actuated for a period between 3 and 20 minutes. Often the assembly 100 is actuated for a period between 5 and 20 minutes. In many versions of the invention, the assembly is actuated for a period of between 8 and 15 minutes.

After the motor controller 596 deactivates the motor 140, the cleaning module 602 is removed from the base. This activity is accomplished by moving the latch assembly 540 to the unlatched state. This is accomplished by depressing to the finger grips 562 towards each other. Finger force it is understood is sufficient to overcome the force that the spring 566 places on the plates 542 and 544 to hold the latch assembly in the latched state. The movement of the finger grips results in the like movement of plates 542 and 544. The movement of plates 542 and 546, pivots plates 546 and tabs 548 pivoted inwardly. The pivotal movement of the tabs 548 retracts the tabs from slots 612 so as to place the latch assembly 540 in the unlatched state. At this time, the cleaning module 602 can be removed from the assembly base 102.

Figure 78:
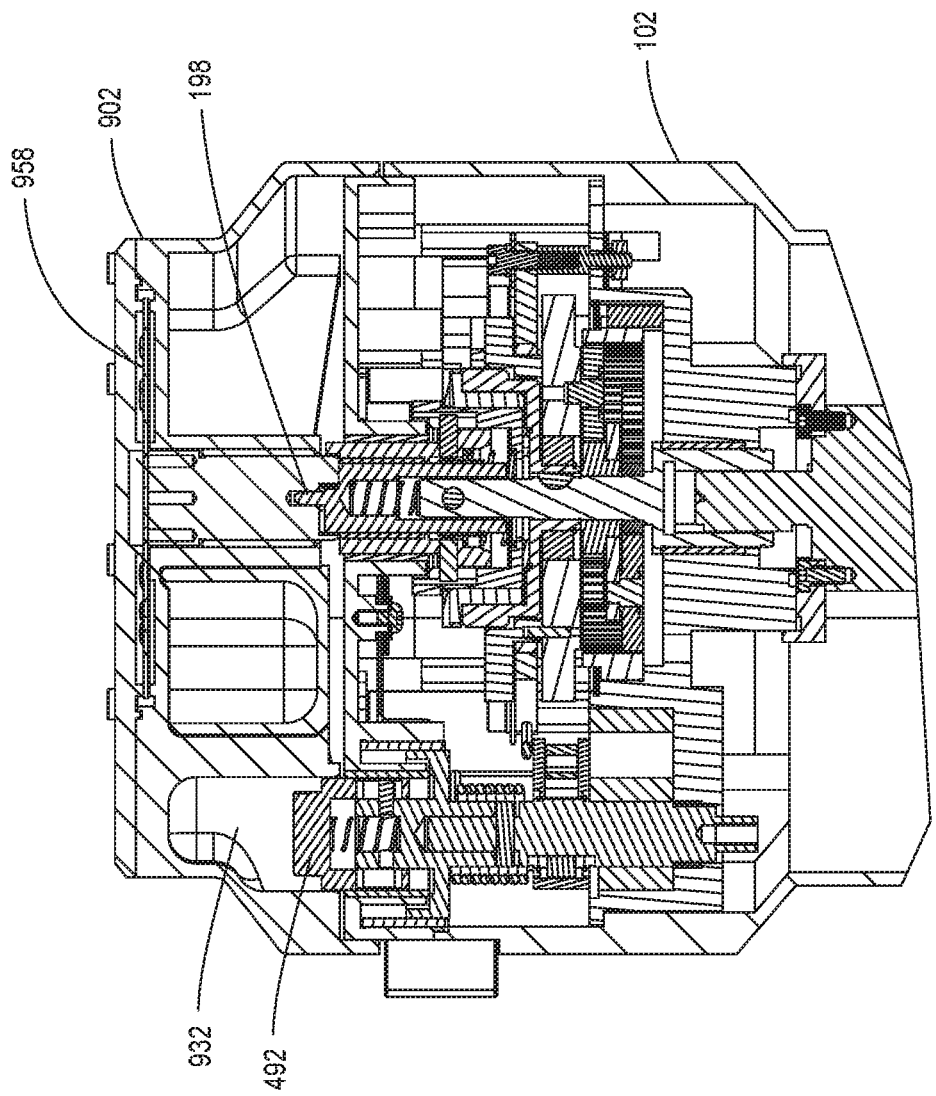
FIG. 78 is a cross sectional view of the milling module mounted to the assembly base.
Figure 79:
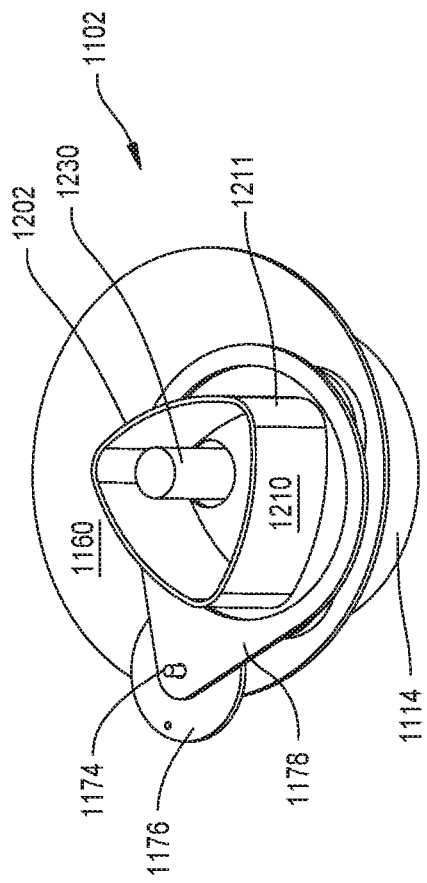
FIG. 79 depicts how the cage of an alternative cleaning module may be disposed around the fluted screw and shaving tube according to this invention.
Figure 82:
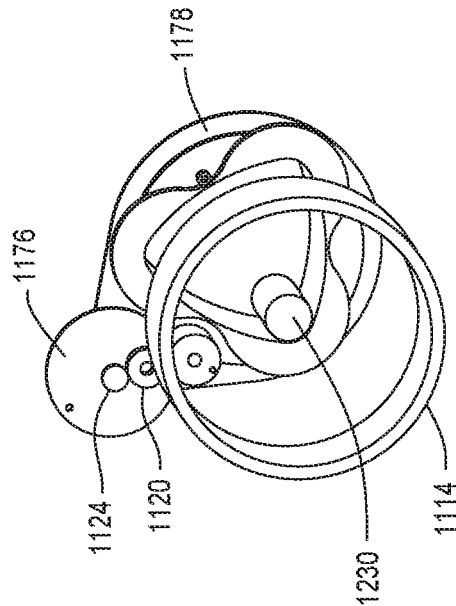
FIG. 82 is a perspective of the drive components of the module of FIG. 79.
Figure 81:
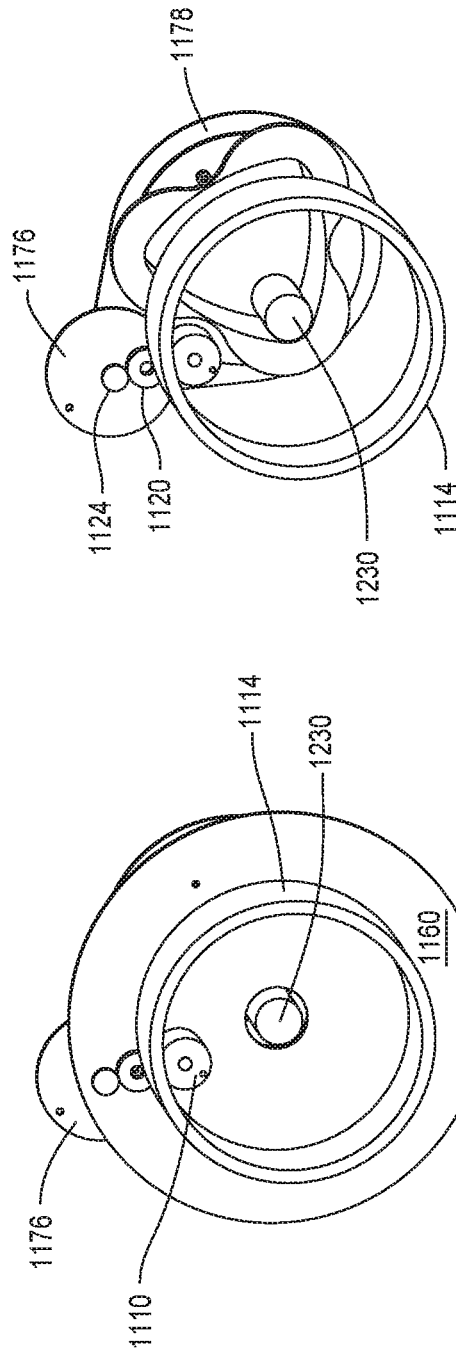
FIG. 81 is a perspective view of the underside of the module of FIG. 82.
Figure 84:
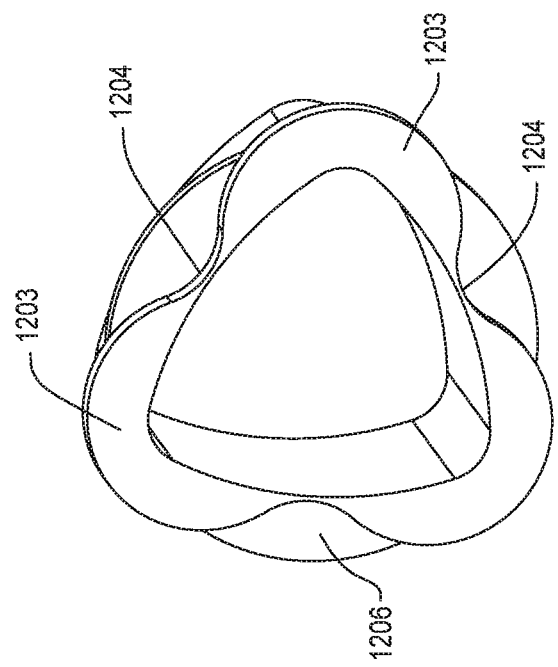
FIG. 84 is a perspective view of the undersurface of the cage.
Figure 83:
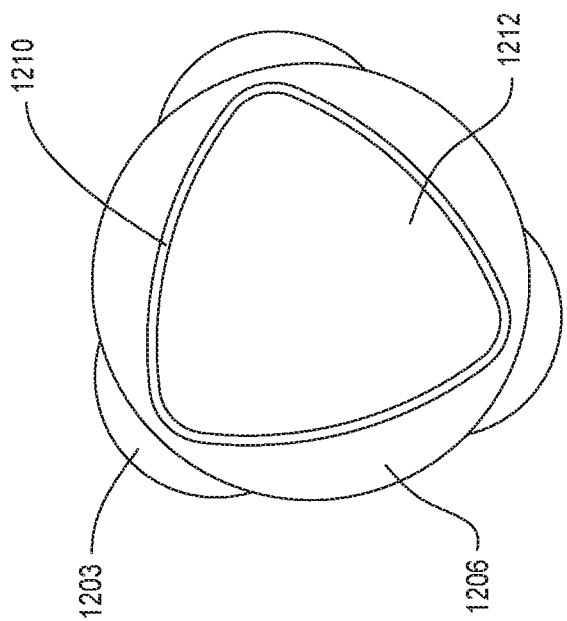
FIG. 83 is a top plan view of the alternative cage.

Milling module 902 is then seated over the assembly base 102. The latch assembly 540 is used to hold the milling module 902 to the assembly base 102 the same way the assembly 540 is used to hold the cleaning module 602 in position. Latch assembly tabs 548 extend through the openings 908 in the bottom shell 904 of the milling module 902. When the milling module is so secured to the assembly base 102, the underside of the assembly stem 966 is disposed above the primary coupler. At a minimum, coupler pin 198 seats in stem bore 974. The bottom end of sleeve 926 is disposed over the tube coupler 348. The arm coupler 486 seats in opening 932 in the underside of the bottom shell as seen in FIG. 78.

Figure 73:
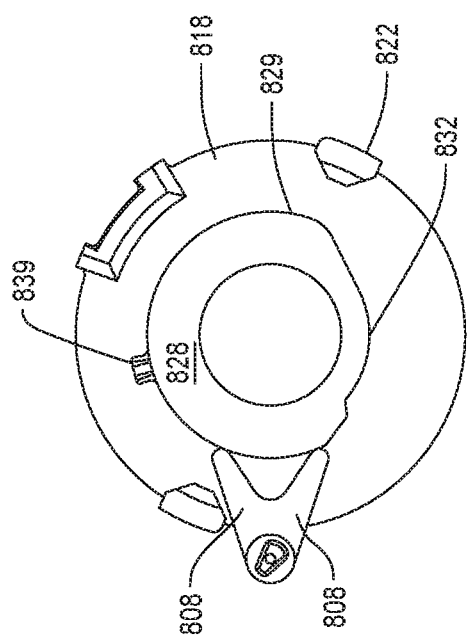
FIG. 73 depicts the relationship of the lock plate to the drive pin when the lock plate is in the locked state.

The cleaned bone stock is then transferred to the miller hopper 952. This process starts with the unlatching of shell 660 from the rest of the cleaning module 602. As a result of the rotation of latch 880, the lock disc 818 returns to the rotational position of FIG. 73. The movement of the lock disc results in the pivoting of the drive pin 802. The pivoting of the drive pin result in the like pivoting of arm 750 and cage 764. The cage 764 is pivoted to the orientation as seen in FIG. 77D. Here the cage 764 is located so the press block is located more to the perimeter of the tumble plate 710 and spaced away from the fluted screw 690.

When cage 764 is in this orientation, the cleaning module 602 is brought to the open end of the hopper 952 and the end of the cage adjacent tab 792 is directed to the hopper. With the assistance of gravity, the cleaned hone stock is then transferred into the hopper 952. Once the transfer is complete, the plunger 953 is placed in the hopper.

When the milling module 902 is seated over the assembly base top plate 122, and the catch tray 980 is latched in module opening 924, magnet 1010 is disposed over sensor 587. The sensor 587 therefore outputs a signal to the motor controller 596 indicating that this field is sensed. Motor controller 596 interprets the presence of this signal as indicating the milling module 902, including the catch tray 990, in the correct position for the milling process to proceed. Motor controller then actuates the LED 591 associated with switch 590.

To mill the bone, switch 590 is depressed. When assembly 100 is so configured to mill hone, the motor controller 596 actuates the motor for as long as the switch 590 is depressed. The resultant rotation of the primary coupler 194 results in the rotation of a milling component such as the cutting disc 958. While the cutting disc 5958 is rotated, the person performing the milling process presses down on the plunger 953. The bone stock is pushed against the rotating cutting disc. The cutting elements urge the hone stock against the impingement plate 984 so as to result in the hone stock being sheared into hone chips. The bone chips fall through the openings 963 in the cutting disc and into the catch tray 988.

At the completion of the milling process the catch tray 988 is removed from the milling module 902. The bone chips are available for use in the procedure in which the use of the chips is required.

As a result of the removal of the catch tray 988 from the milling module 902, the magnet 1010 is withdrawn away from the complementary sensor 587. The sensor 587 therefore stops asserting the signal to the motor controller 596 that a milling module 902 with latched catch tray 988 is attached to the assembly base 102. As a result of the change in signal from sensor 587, the motor controller 596 no longer actuates the motor 140 upon the depression of switch 590.

Assembly 100 of this invention thus provides a means to first clean and then mill freshly harvested bone stock that requires only minimal human contact with the bone stock. The bone cleaning module 602 is designed to remove the soft tissue that is often attached to this bone stock. Module 602 is designed so that if during the cleaning process, the bone stock gets hung up between the fluted screw and the shaving tube the components of the module cooperate to shear the bone stock from these components. Bone cleaning module 602 is further configured to, between the pressing phases in which cleaning typically occurs, tumble the bone stock. This appreciably increases the likelihood that the exposed surfaces of each piece of bone stock will be pressed against the fluted screw and the shaving tube. Increasing the likelihood that each piece of bone stock is so positioned results a like increase in the thorough cleaning of each piece of bone stock.

To ensure the bone stock is so cleaned, the presence of indention 769 in the cage provides the cage with a void space 765 such that there is significant space adjacent the press block 772. The advantage of the large amount of space adjacent the press block facilitates the dislodgement of the bone away from the fluted screw and the shaving tube during the tumble phase. Then, during the sweep phase, the presence of indention 769 means that the distance between panels 768 and 770 of the cage is smaller than it would be if indentation 769 was not present. This means that the tumbled bone is contained in small space. This increases the extent to which the bone, during the sweep phase, is gathered and directed towards the fluted screw for the next press phase.

Still a further feature of the cleaning module of this invention is that tissue excised from the bone is augered into the catch space 682 associated with the module shell 650. This means that person performing the cleaning process does not have to be concerned with collecting and disposing of this waste material.

The bone cleaning module 602 of this invention is further designed, so that after the cleaning process, upon removal of the shell 650, the cage is held a specific position relative to the fluted screw 690 and shaving tube 724. More particularly, the cage 764 is positioned so as to facilitate the gravity assisted transfer of the cleaned bone stock into the milling module 902.

VI. Alternative Cleaning Module Features

Figure 86:
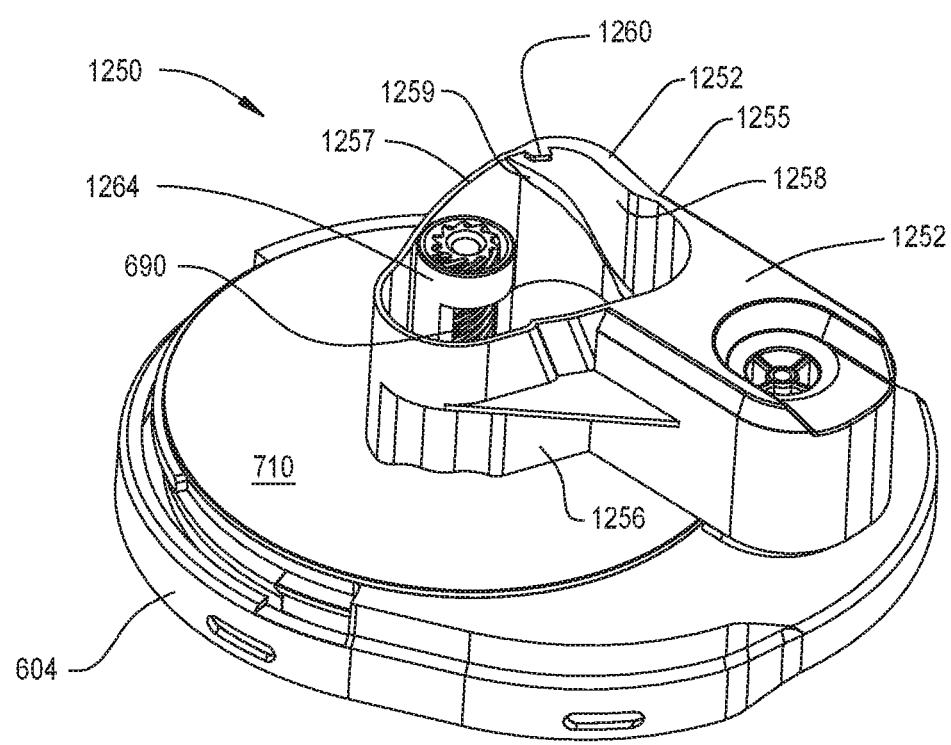
FIG. 86 is a perspective view of the inside of an alternative cleaning module of this invention.

FIG. 86 depicts the inside features of an alternative cleaning module 1250 of this invention. Module 1250 includes many of the same basic components as the cleaning module 602. Accordingly, these components are not redescribed. One difference between the two modules is the structure of the arms. Module 1250 includes an arm 1252 and a cage 1254. Arm 1252 is substantially identical in shape and function to arm 750. Cage 1254 extends from arm 1250. A difference between the two assemblies is that in the comparison of the assemblies of FIGS. 54 and 86, cage 764 extends outwardly to the right of arm 750; cage 1254 extends to the left of arm 1252. Cage 1254 includes panels 1255, 1256 and 1257. Panels 1255, 1256 and 1257 are analogues to, respectively, panels 766, 768 and 770 of cage 764. Not seen in the press block between the corner formed by where panels 1256 and 1257 meet.

Cage 1254 is further formed to have a ramp 1258. The ramp 1258 protrudes inwardly from panel 1255. Ramp 1258 includes an inclined surface 1259 analogues to surface 782 of rib 780, ramp surface not identified. Surface 1259 extends upwardly from panel 1255 to the corner between panels 1255 and 1257. Module 1252 includes cage 1254. As rib 1258 extends upwardly, the width across the base of the rib decreases. Cage 1254 is further formed to have a tab 1260 that projects inwardly from top of panel 1257. Tab 1260 is located over a section of the panel 1257 from which rib 1258 extends downwardly. The tab 1260 extends inwardly beyond the apex of rib 1258.

Figures 87, 88:
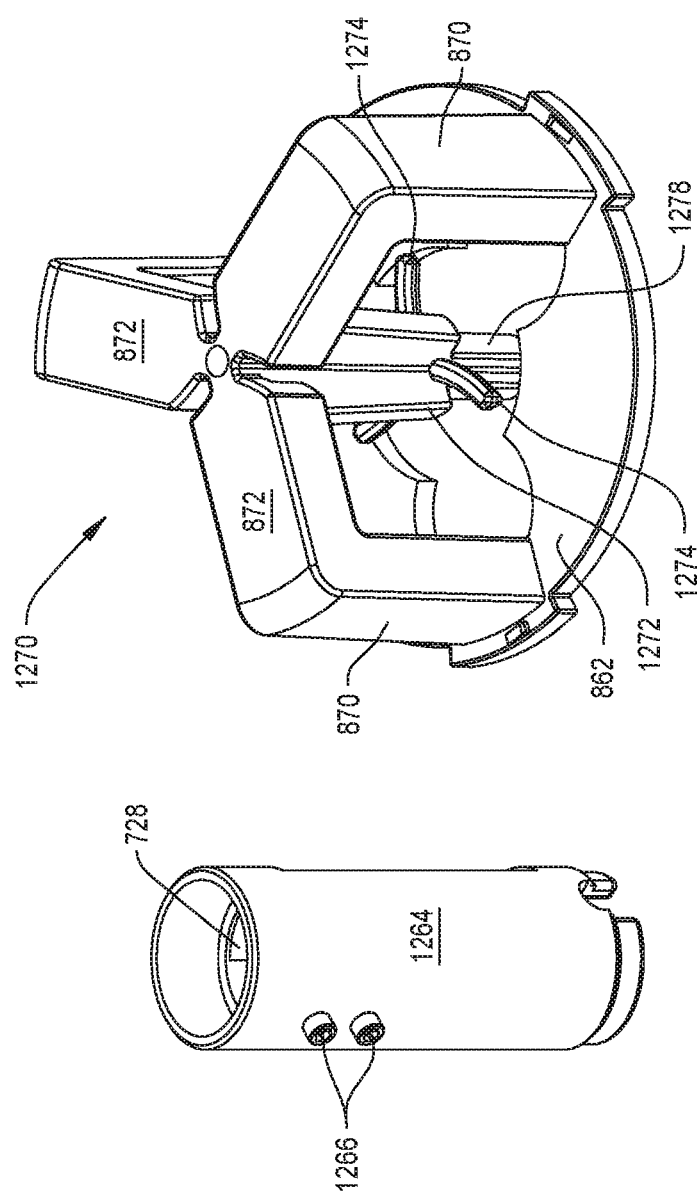
FIG. 87 is a perspective view of an alternative shaving tube internal to a cleaning module of FIG. 86.
FIG. 88 is a perspective view of an alternative hub internal to the catchment of the cleaning module of this invention.

Module 1252 also includes the shaving tube 1264 seen best in FIG. 87. Shaving tube 1264 includes the features of the previously described shaving tube 724 of FIG. 46. Shaving tube 1264 is also formed to have at least one pin 1266, two pins 1266 shown. The pins 1266 extend radially outwardly from the outer surface of the shaving tube 1266. Not seen are the bores in which the pin 1266. The shaving tube 1264 is constructed so the pins 1266 extend outwardly from a location more towards the top than the bottom of the shaving tube. The pins 1266 extend outwardly from a section of the shaving tube opposite the section of the tube in which the window 722 is formed. The pins 1266 are positioned to rotate through an area above the press block and that is adjacent the ramp 1258.

FIG. 88 illustrates the hub 1270 of cleaning module 1262. While there some aesthetic differences, hub 1270 includes the base 862, stanchions 870 and webs 872 of hub 860. A pin 1272 extend downwardly from where webs 872 meet. A foot 1278 extend downwardly from the free end of pin 1278. Pin 1272 and foot 1278 are not cylindrical in shape. Instead both the pin 1272 and foot 1278 are formed with longitudinally extending indentations. The pin 1272 and foot 1278 perform the same generally function as, respectively, pin 874 and foot 878 of hub 860.

The hub 1270 is further formed to have plural fins 1274 that extend radially outwardly from the pin 1272. In the illustrated version of the invention, the hub 1270 is formed with three equangularly spaced apart fins 1274, two fins identified. In the depicted version of the invention, each fin 1274 is in the shape of elongated tubularly shaped rod. The fins 1274 extend outwardly from the portion of the pin 1272 above the hub base 862. While the fins 1274 extend radially outwardly from pin 1272, the fins are not linear in shape. Instead the fins 1274 are curved. As each fin 1274 extends radially outwardly, the fin tines curve to the adjacent tine. Each fin 1274 curves in the same direction. The cleaning module 12672 is configured so that the curve of the fins 1274 is in a direction that is opposite the direction in which the fluted screw 690 rotates during the cleaning process.

When cleaning module 1262 is assembled, hub 1270 substitutes for the first described hub 860. Foot 1278 seats in bore 704 formed in the fluted screw 690. Since the fins 1274 are located above the base 862 of the hub 1270, the tines are located above the shaving tube and the fluted screw. The components forming the cleaning module 1274 are shaped so that fins 1274 are located above the shaving tube 724.

Bone stock is cleaned using module 1262 in the same generally way in which the bone stock is cleaned using module 602. In versions of the invention that employ cleaning module 1262 the complementary base is configured to rotate the shaving tube 1264 clockwise from the perspective of the tube seen in FIG. 86. One difference between the two cleaning processes occurs during the clear and gather phase. When module 1262 is employed to clean bone, the movement of the cage 1254 towards the shaving tube 1264 during the shift phase is limited by the abutment of tab 1260 against the shaving tube 1264. This ensures that during the subsequent clear and gather phase there will be a clearance between the cage 1254 and the shaving tube 1264 that will allow the pins 1266 integral with the shaving tube to rotate between the shaving tube and rib 1254. During the clear and gather phase, bone stock trapped by the fluted screw is rotated against the inclined surface 1259 of ramp 1258. Once the movement of the bone stock is blocked by the abutment of the bone stock against the ramp, the shaving tube cuts the bone stock from the fluted screw.

During the cleaning process, bone stock may become stuck above the press block. The rotating pins 1266 function as wipers against this bone stock. The pins thus wipe the bone stock away from the press block. Gravity causes the bone stock to fall to plate 710. Pins 1266 also wipe away bone that may be adhering to the ramp 1258. During a subsequent sweep phase this bone stock is forced against the press block so the bone will again be pressed against the fluted screw 690.

The soft tissue cut away from the bone stock is augered upwardly between the fluted screw 690 and the shaving tube 1264. The strands of soft tissue rotate against the fins 1274 integral with pin 1272. The fins 1274 thus direct the strands of soft tissue radially outwardly from pin 1272. This facilitates the movement of the soft tissue away from the hub 1270 and towards the outer perimeter of the catch space 682.

Upon removal of the shell 660 with hub 1270 from the rest of the cleaning module 1262, some soft tissue is typically disposed above the fluted screw and shaving tube. Fins 1274 supports these strands of tissue to prevent them from falling out of the catch space 682 and into void space in which the cleaned bone stock is located.

VII. Alternative Cleaning Module

FIGS. 79-84 illustrate an alternative arrangement for components of a cleaning module 1102 of this invention. Specifically, in this version of the invention the cleaning module 1102 has a cage 1202. The cage 1202 has three outwardly bowed side walls 1210, one side wall identified that are connected together to form a triangle. The corners 1211 between the side walls 1210 are rounded, one corner identified. The interior space between the side walls 1210 is the void space 1212 in which the bone stock to be cleaned is deposited. The cage 1210 is open at the bottom. The cage 1210 is further formed so as to have three curved lobes 1203, two lobes identified in FIG. 84. Each lobe 1202 extends outwardly from one of the corners 1210. A concave shaped transition surface 1204 extends between each pair of adjacent lobes 1202, two surfaces identified in FIG. 84. Each transition surface 1204 is closest to the adjacent side wall 1210 at the mid-point location of the side wall between the adjacent corners 121.

The cage 1202 is further formed so that above the lobes 1203 a ring 1206 extends radially outwardly from the side walls 1210 and corners 1211. Ring 1206 has a diameter so that the ring is located radially inwardly from the lobes 1203 and extends radially outwardly from the sections of the transition surfaces 12-4 closest to the side walls 1210. The ring is formed so to have teeth, not illustrated, that extend around the outer circumferential surface of the ring.

While not seen, it should be understood that the cage may be formed with a features analogues to press block 772 and rib 780. The feature analogues to the press block functions as the press component of the cage that pushes bone against the fluted screw and shaving tube. The feature analogues to rib 780 clears trapped bone tissue from the fluted screw and shaving tube.

Cage 1202 seats on a circularly shaped disk 1160. Disk 1160 is formed with a center located through hole 1162. The disk 1160 has three holes 1164, 1166 and 1168 that are linearly aligned along a line that extends radially outwardly from the center of the disk 1160. Hole 1164 is located closest to the center of the disk 1160. Hole 1168 is located furthest from the center of the disk 1166. Disk 1160 is further formed with a hole 1170. Hole 1170 is spaced arcuately away from holes 1164-1168. Disk 1160 is formed so that hole 1170 is located approximately the same distance from the center of the disc as hole 1166.

The cage 1202 is held over the disc 1160 by an arm 1178. Arm 1178 is approximately teardrop in shape. The widest portion of the arm has a through hole 1180. Hole 1180 is dimensioned to receive the cage 1202 such that the side panels 1210 and corners 1211 of the cage can rotate within the hole. Hole 1180 has a diameter that is less than the diameter of the ring 1206 integral with cage 1202.

A pin 1174 extends from disk 1160 to the arm 1178 to hold the arm to the disk. One end of pin 1174 is mounted in hole 1168 formed in the disk 1160. The opposed end of the pin 1174 extends through an opening 1182 formed in the narrow width portion of the arm 1178. The components forming this bone cleaner are shaped so that the arm 1178 is able to pivot freely around pin 1174.

Given that arm 1178 rests on ring 1206 it should be appreciated that the arm is spaced above disk 1160. A gear 1176 is sandwiched between the disk 1160 and the arm. More particularly, pin 1174 holds the gear 1176 to the disk 1160. The gear 1176 is held to the pin 1174 so the pin and gear rotate as a single unit. Teeth, not illustrated, extend outwardly from the outer circular side wall of the gear 1176. The gear 1176 is dimensioned so that teeth of the gear 1176 mesh with the teeth integral with the ring 1206 that is part of the cage 1202.

This version of the cleaning module of the present invention also includes a roller 1222 that functions as a cam. Roller 1222 is mounted by a pin 1220 to the top surface of disk 1160. Pin 1220 is mounted in hole 1170 internal to the disk. Not illustrated is a spring that urges the cage 1202 towards roller 1222. This spring presses the cage 1202 towards the roller so that lobes 1202 and transition surfaces 1204 bear against the roller 1202.

Cleaning module 1102 includes the fluted screw encased with a shaving tube of the previously described cleaning module 602. In FIGS. 79-82 and 85A through 85G the fluted screw and shaving tube are depicted as a cylinder 1230. The fluted screw and shaving tube extend through the center hole 1162 in the disk. When cleaning module 1102 is assembled, cage 1202 is positioned over the disk so the fluted screw and shaving tube are seated in cage void space 1212.

Disk 1160 and the components mounted to the disc are disposed above a static cylindrical ring gear 1114, also part of the cleaning module of this invention. The disk 1160 it should be understood is disposed above the ring gear 1114. Not illustrated are the structural components that hold disk 1160 for rotation above the ring gear 1114. Also not illustrated are the teeth that are formed on the inner surface of the ring gear. A drive gear 1108 seen on only in FIG. 80 is disposed in the ring gear below disk 1160. The drive gear 1108 may be similar to gear 190. Thus, this drive gear 1108 rotates with the spindle that rotates the fluted screw. The drive gear 1108 is formed to have a diameter less than the diameter of the inner surface of the ring gear 1114.

A planet gear 1110 is rotatingly mounted to the underside of disk 1160 adjacent the drive gear 1108. A pin 1112 one end of which is seated in disk hole 1164, rotatingly holds planet gear 1110 to disk 1160. The components forming cleaning module 1102 are further arranged so that the teeth of the planet gear engage both the teeth of the drive gear 1108 and the teeth located around the inside of the static ring gear 1106. Planet gear 1110 is shaped so that the teeth of the gear extend into the void space between the top of ring gear 1114 and the underside of disk 1160.

Gears 1120 and 1124 are also rotatingly mounted to the underside of the disk 1160. Gear 1120 is mounted to the disk by a pin 1122 that extends downwardly from hole 1160. The components of the cleaning module 1102 are arranged so that extends radially inwardly and radially outwardly of the top of the ring gear 1114. The portion of gear 1120 disposed within the ring gear 1114 engages the teeth of the adjacent planet gear 1110. Gear 1124 is mounted to pin 1174 to rotate with the pin 1174. Gears 1124 and 1176 and pin 1174 rotate as a single unit. Gear 1124 is positioned to be driven by gear 1120.

When cleaning module 1102 is actuated, a drive component rotates the fluted screw. An assembly that includes a clutch similar to clutch 278 may be employed to periodically rotate the shaving tube. Drive gear 1108 is continuously rotated. The drive gear 1108 functions as a sun gear of a planetary gear assembly. Plane gear 1110 is the single planet gear of this assembly. Disk 1160 is the carrier and ring gear 1106 the static ring gear. Thus, as a result of the rotation of drive gear 1108, the planet gear 1110 rotates around the ring gear 1106. The rotation of the planet gear 1110 rotates disk 1160 around the center axis of the disk.

Since disk 1160 rotates it should be understood that pin 1174 likewise rotates. This means that the arm or more particularly the outer portion of the arm engages in a rotational motion as seen in FIGS. 85A through 85G. By extension this means that the cage 1202 rotates around fluted screw and shaving tube.

The rotation of planet gear 1110 results in a like rotation of gear 1120 and, by extension, gear 1124. The rotation of gear 1124 and therefore pin 1174 rotates gear 1176. Since gear 1176 engages the teeth of ring 1206, ring 1206 likewise rotates. Since ring 1206 is part of cage 1202 this means that when cleaning module 1106 is actuated, simultaneously with disk 1106, cage 1202 rotates within hole 1180 internal to the arm 1178.

The biasing member urges lobes 1203 and transition surfaces 1204 against the roller 1222. This means that, as the cage 1202 is rotated in the arm 1178, lobes 1203 and transition surfaces 1204 are alternatingly urged against the roller. When the lobes 1203 are abut roller 1222, the cage is in the position as depicted in FIGS. 85C, and 85DE, the cage is approximately centered over the fluted screw and having tube. When the transition surfaces 1204 abut roller 1222, the cage is positioned as depicted in FIGS. 85A, 85F and 85G; the cage is positioned so the fluted screw and shaving tube are located adjacent the inside of one of the side walls 1210 or corners 1211 of the cage. FIGS. 85B and 85F depict intermediate positions of the cage relative to the fluted screw and side walls between when one of the outwardly directed lobes 103 or an adjacent or inwardly directed transition surface 1204 is abutting the roller.

Thus in this version of the cleaning module of this invention, the plural movements of the components serve to sequentially cycle the cage so, the corner 1211 of the cage is located adjacent fluted screw and shaving tube as seen in FIGS. 85A and 85G. At this time, the cleaning module is in a press phase of a cleaning cycle. Then, as depicted by FIG. 85B, the cage rotates so the inner surface of a side wall 1210 is located adjacent the fluted screw and shaving tube. The simultaneous rotation of the disk 1160, the rotation of the cage around its own axis and the orbiting of the cage around the center of the disk in FIGS. 85C through 85F can be considered the sweeping of the bone stock for the press phase of the next cleaning cycle.

VIII. Alternative System Embodiments

The above is directed to specific versions of the invention. The invention may have features different from what has been described. For example, the features of the different cleaning modules 602, 1102 and 1262 may be combined. For example, components similar to press block 772 and ribs 768 and 780 may be found internal to cage 1202.

Also, there is no requirement the cleaning modules of this invention always be used with the described milling module. Likewise, other assemblies may be used to clean the bone stock before the milling module of this invention is used to convert the bone stock into bone chips.

The features of the different embodiments of the invention may be combined.

Alternative cleaning modules of this invention may have cleaning elements other than the disclosed fluted screw and shaving tube assembly for removing the soft tissue from the bone stock. Thus, it is within the scope of this invention that the cleaning element consist of one or more brushes. Typically these brushes rotate. In these versions of the invention, the cage is formed with features that facilitate the pressing of the bone stock against the brushes.

The number of and sequence of the phases of a single cleaning cycle may also vary from what has been described above. Thus, it is within the scope of this invention that the clear phase, the phase in which the bone stock that is hung up on the cleaning elements is cleared from the cleaning elements may occur between the press phase and the tumble phase. A benefit of this construction of the invention is that all the bone stock, including the bone stock just cleared from the cleaning elements is subjected to tumbling in the tumble phase.

Likewise, in versions of the invention in which the clear phase occurs after the execution of the press phase and the tumble phase, owing to the construction of the components forming the cleaning module, the following phase may be one in which the bone stock is simultaneously cleared from the cleaning elements and swept into a section of the module for the execution of the next press phase. Thus, in this version of the invention, a cleaning cycle would not have a distinct sweep phase. Similarly, in some versions of the invention, all that occurs in the clearing phase is the removal of the bone stock from the cleaning elements. In these versions of the invention, the system may be configured to prior to the execution of a press phase, execute a distinct sweep phase in which the tumbled bone stock is gathered into a section of the module so, in the press phase the bone stock will be pressed against the cleaning elements.

Similarly, in some versions of the invention, owing to how the components of the cleaning module move, simultaneously with the clearing of the bone stock from the cleaning elements, the bone stock may be tumbled. Thus, in these versions of the invention, a single cleaning cycle may consist of: a press phase; a clear and tumble phase; and a sweep phase in which the bone stock is gathered for the next press phase.

Also there is no requirement that in each version of the invention each cleaning cycle consist of the same sequence of phase phases. Thus, in some versions of the invention the sequential cleaning may include different phases. For example a first cleaning cycle may consist of a press phase and a tumble phase. A second cleaning cycle may consist of a press phase followed by a clear phase. In another alternative construction of the invention, the first cleaning cycle may consist of a press phase and a tumble phase. The second cleaning cycle may consist of a press phase followed by a clear phase followed by a tumble phase.

The stated dimensions and ratios, unless present in the claims, are understood not to be limiting but merely examples.

It may not be necessary for all versions of the invention to have all of the described components. For example, it is anticipated that in some versions of the invention the motor internal to the assembly base that rotates the primary spindle, the arm cam and tube cam may be directly connected to the primary spindle 170. In these versions of the invention, there is no gear train between the motor shaft 145 and the primary spindle 170.

In some versions of the invention, the pin that holds the fluted screw steady may be formed integrally with the cap that extends over the opening in the shell through which the excised soft tissue is augered in to the catch space. Thus, in these versions of the invention, it is not necessary to provide a hub for holding this pin static relative to the rest of the cleaning module.

In alternative versions of the invention, assemblies other than the described clutch cam and arm cam may be employed to ensure that, during a cleaning cycle, the components of the cleaning module move in the proper sequence to ensure the bone stock is subjected to each of the cleaning phases. Thus, in one alternative construction of the invention, gear trains are incorporated to the base 102 to drive the order to ensure that during a cleaning cycle, the couplers 194, 348, 486 in the appropriate sequence. In these versions of the invention, one or more cams may be integral to the gear trains. These cam may rotate around axes that are no concentric with the axis around which the primary spindle 170 rotates.

Still other versions of the invention may not include cams and associated followers that employed to ensure the correct sequence of movements of the components internal to the bone cleaning module. In some versions of the invention, internal to the base there may be one or more electrically displaced components. For example solenoids may be used to selectively engage/disengage gears used to drive one or more of the couplers 194, 348 and 486.

Likewise, the directions of rotation of the components are understood to not be limiting but examples. Thus components that move in one direction to accomplish a task, such as the arm cam, the tube cam and rocker arm may move in the opposite directions in other versions of the invention. Likewise, there is no requirement that in all versions of the invention, the components that rotate, rotate in the same direction for each phase of a cleaning cycle. For example, in some versions of the invention, during the clear phase of a cleaning cycle, the fluted screw and shaving tube may rotate in opposite directions. Further, it is within the scope of this invention that the sequence of movements of the components may be different from what has been described. For example, in some versions of the invention, during the clear phase of a cleaning cycle, the fluted screw may be static while the shaving tube rotates.

Similarly the drive assembly that moves the press component and the clearing component may not always be configured to displace these components in a curved path. In some versions of the invention, the drive assembly may be configured to reciprocate the press component and the clearing component on a path of travel that instead of being curved, is linear. In these and other versions of the invention the cage that defines the press component and clearing component may not completely circumferentially surround the cleaning elements.

Similarly, the orientation of the components may be different from what has been described. In some versions of the invention, the fluted screw may have an orientation other than, relative to the brevity plane, vertical. Thus it is within the scope of this invention that the fluted screw may have, relative to the gravity plane, an orientation that is either diagonal or horizontal. In a version of the invention in which the fluted screw an, by extension the shaving tube, have this orientation, a cage similar to cage 1202 may rotate around these components.

It should thus be appreciated that in alternative cleaning modules of this invention the soft tissue that is cut from the bone stock may be transported from the void space in which the cutting occurred to the catch space along a path of travel other than an upwardly directed horizontal path. In some versions of the invention, the bone cleaning module is constructed so that the soft tissue engages in a path of travel that relative to the plane of gravity is downward, sideways or diagonal. If in the gravity plane the catch space is located below the void space in which the bone stock is cleaned gravity may at least partially assist in the transfer of the cut tissue into the catch space.

Likewise it should be understood that there is no requirement the cleaning module of this invention with the features that facilitate the transport of the removed soft tissue away from the module components that remove the tissue to the catch space always be used with module components that cycle the bone stock through each of the above described press, tumble, shift, clear and gather and sweep phases.

Thus in one alternative construction of this invention, the cleaning element consists of a brush. During a press phase a device performs the function of the cage and presses the bone stock against the brush as the brush rotates. In another phase, a ring is forced over the brush. The ring clears entrained bone from the brush and pushes the debris, the soft tissue, trapped in the bristles of the brush to the catch space. The ring thus functions as the transfer component that moves the excised soft tissue into the catch space.

In versions of the invention wherein the cleaning element consists of a first cutter with a first cutting edge and a second cutter with a second cutting edge the first and second cutters may be components other than a fluted screw and a shaving tube. In this version of the invention one or both cutters may be blades, each blade having a cutting edge. The drive assembly is configured to move one of the cutters relative to the other cutter so soft tissue is caught and cut between the cutting edges. A plunger adjacent the cutting edges functions as the transfer component that moves the cut tissue from the void space in which the bone stock and cutters are located to the catch space.

In the described version of the invention, the cages that defines the space in which the bone stock is contained and that pushes the bone stock against the cleaning elements are shown as being shaped so as to fully enclosed the bone stock. This is likewise understood to be exemplary and not limiting.

In alternative versions of the invention sensors other than sensors that measure the presence/absence of a magnetic field may be employed to determine whether or not the cleaning module is in the locked state or a catch tray is fitted to the milling module. For example, in alternative versions of the invention, contact sensors may perform this function. A benefit of this version of the invention is that it the expense of providing the cleaning module and milling module with magnets.

In some of the invention some, but not all, of the functions performed by the motor controller are located in the assembly base. Other functions performed by the motor controller are contained in the power console to which the assembly base is attached.

It is therefore the object of the below claims to cover all such variations and modifications that come within the true spirit and scope of this invention.

What is claimed is:

1. An assembly for milling bone, said assembly including:
    a shell with an inlet opening configured for depositing of bone stock and an outlet opening configured for discharging of bone chips;
    a milling component moveably disposed in said shell between the inlet opening and the outlet opening, the milling component configured to, when actuated convert bone stock introduced through the inlet opening into bone chips discharged through the outlet opening;
    a catch tray that is removably attached to the shell adjacent the outlet opening to receive the bone chips; and
    a base to which said shell is removably attached, the base including a drive assembly configured to actuate the milling component;
    a sensor is attached to the base, said sensor being adapted to monitor the shell for the presence/absence of the catch tray and generate a sensor signal that varies as a function of the presence/absence of the catch tray; and
    a controller configured to regulate the actuation of the drive assembly based on the sensor signal.
2. The assembly for milling bone of claim 1, wherein when the sensor signal indicates that the catch tray is absent, the controller inhibits actuation of the milling component.
3. The assembly for milling bone of claim 1 or 2, wherein said sensor is configured to monitor the presence of a magnetic field and a magnet is mounted to said catch tray.
4. The assembly for milling bone of claim 3, wherein when the catch tray is positioned in the shell and the shell is seated on the base, the magnet is located above said sensor.
5. The assembly for milling bone of claim 1, wherein said sensor is a Hall-effect sensor.
6. The assembly for milling bone of claim 1, wherein said base includes a motor and wherein actuation of said motor results in like actuation of the milling component.
7. The assembly for milling bone of claim 6, wherein said base includes a control button comprising a contact switch that is connected to said controller.
8. The assembly for milling bone of claim 7, wherein said switch is adjacent to a light emitting diode (LED) that is configured to illuminate said switch.
9. The assembly for milling bone of claim 8, wherein said controller, on receipt of said sensor signal, is configured to actuate said light emitting diode (LED) associated with said switch to provide a visual indication that said switch can be depressed to start milling.
10. The assembly for milling bone of claim 1, wherein said base includes a base shell having a top plate.
11. The assembly for milling bone of claim 10, wherein said top plate is formed from material that does not attenuate passage of localized magnetic fields.
12. The assembly for milling bone of claim 10, wherein a circuit board is mounted to an underside of said top plate and said sensor is mounted to said circuit board.
13. The assembly for milling bone of claim 10, wherein a latch assembly is mounted to an underside of said top plate and releasably holds said base shell to said base.
14. The assembly for milling bone of claim 1, wherein said milling component is a cutting disc.
15. The assembly for milling bone of claim 7, further comprising a cleaning module that can be attached to said base when said shell is not attached thereto.
16. The assembly for milling bone of claim 15, wherein said sensor is also configured to generate a sensor signal for said controller when said cleaning module is attached to said base to allow actuation of said motor.
17. The assembly for milling bone of claim 16, wherein said sensor signal further activates a light emitting diode (LED) adjacent said switch to provide a visual indication that said switch can be depressed to start cleaning.
18. A system for bone preparation, said system including:
    a milling module comprising:
        a milling module shell with an inlet opening configured for depositing of bone stock and an outlet opening configured for discharging of bone chips,
        a cutting disc moveably disposed in the milling module shell between the inlet opening and the outlet opening, the cutting disc configured to, when actuated, convert bone stock introduced through the inlet opening into bone chips discharged through the outlet opening, and
        a catch tray that is removably attached to the shell adjacent the outlet opening to receive the bone chips;
    a cleaning module comprising:
        a cleaning module shell including a void space in which bone stock to be cleaned is deposited, and
        at least one cleaning element disposed in the void space and configured to, when actuated, remove soft tissue from the bone stock; and
    a base to which the milling module or cleaning module is configured to be removably attached, the base including a drive assembly configured to actuate the cutting disc or the at least one cleaning element;
a sensor is attached to the base, the sensor configured to monitor the milling module for the presence/absence of the catch tray when the milling module is attached to the base and generate a sensor signal that varies as a function of the presence/absence of the catch tray; and
a controller configured to regulate the actuation of the drive assembly, wherein the controller is configured to receive the sensor signal and to, when the milling module is attached to the base and when the sensor signal indicates that the catch tray is absent, inhibit actuation of the cutting disc.

19. The system of claim 18, wherein the sensor is also configured to generate a sensor signal when the cleaning module is attached to the base and allow actuation of a motor of the drive assembly.

20. A method of bone preparation with a system for bone preparation including: a milling module having a milling component and a catch tray; and a base unit having a sensor, a controller, and a motor, said method comprising the steps of:
attaching the milling module to the base;
generating a sensor signal from the sensor to the controller when the milling module is attached to the base unit and the catch tray is present in the milling module; and
regulating actuation of the motor based on the sensor signal.

21. The method of claim 20 further comprising the step of providing a visual indication on the base that the milling module with the catch tray present therein is attached and milling can be started.

22. The method of claim 20 further comprising the steps of:
attaching a cleaning module to the base;
generating a sensor signal from the sensor to the controller when a cleaning module is attached to the base;
regulating the actuation of the motor based on the sensor signal; and
removing the cleaning module from the base.

23. The method of claim 22 further comprising the step of providing a visual indication on the base that the cleaning module is attached and that cleaning can be started.

* * * * *